US007407663B2

(12) United States Patent
Cham et al.

(10) Patent No.: US 7,407,663 B2
(45) Date of Patent: Aug. 5, 2008

(54) MODIFIED IMMUNODEFICIENCY VIRUS PARTICLES

(75) Inventors: Bill E. Cham, Sheldon (AU); Jo-Ann B. Maltais, San Ramon, CA (US)

(73) Assignee: Lipid Sciences, Inc., Pleasanton, CA (US)

(*) Notice: Subject to any disclaimer, the term of this patent is extended or adjusted under 35 U.S.C. 154(b) by 0 days.

(21) Appl. No.: 10/601,656

(22) Filed: Jun. 20, 2003

(65) Prior Publication Data

US 2004/0170649 A1 Sep. 2, 2004

Related U.S. Application Data

(63) Continuation-in-part of application No. 10/311,679, filed as application No. PCT/IB01/01099 on Jun. 21, 2001, now abandoned.

(60) Provisional application No. 60/390,066, filed on Jun. 20, 2002.

(30) Foreign Application Priority Data

Jun. 29, 2000 (AU) .................................... PQ8469
Dec. 28, 2000 (WO) .................... PCT/AU00/01603

(51) Int. Cl.
*A61K 39/21* (2006.01)

(52) U.S. Cl. ................................ 424/208.1; 435/235.1

(58) Field of Classification Search ............. 424/184.1, 424/204.1
See application file for complete search history.

(56) References Cited

U.S. PATENT DOCUMENTS 3,647,624 A 3/1972 Evenson
3,958,939 A 5/1976 Jones
3,983,008 A 9/1976 Shinozaki et al.
3,989,466 A 11/1976 Pan
4,025,423 A 5/1977 Stonner et al.
4,103,685 A 8/1978 Lupien et al.
4,124,509 A 11/1978 Iijima et al.
4,234,317 A 11/1980 Lucas et al.
4,235,602 A 11/1980 Meyer et al.
4,258,010 A 3/1981 Rozsa et al.
4,350,156 A 9/1982 Malchesky et al.
4,391,711 A 7/1983 Jackson et al.
4,399,217 A 8/1983 Holmquist et al.
4,402,940 A 9/1983 Nose et al.
4,431,633 A 2/1984 Machlowitz et al.
4,435,289 A 3/1984 Breslau
4,463,988 A 8/1984 Bouck et al.
4,481,189 A 11/1984 Prince
4,522,809 A 6/1985 Adamowicz et al.
4,540,401 A 9/1985 Marten
4,540,573 A 9/1985 Neurath et al.
4,591,505 A 5/1986 Prince
4,613,501 A 9/1986 Horowitz
4,615,886 A 10/1986 Purcell et al.
4,643,718 A 2/1987 Marten
4,645,512 A 2/1987 Johns
4,647,280 A 3/1987 Maaskant et al.
4,648,974 A 3/1987 Rosskopf et al.
4,668,398 A 5/1987 Silvis
4,671,909 A 6/1987 Torobin
4,676,905 A 6/1987 Nagao et al.
4,677,057 A 6/1987 Curtiss et al.
4,680,320 A 7/1987 Uku et al.
4,696,670 A 9/1987 Ohnishi et al.
4,775,483 A 10/1988 Mookerjea et al.
4,832,034 A 5/1989 Pizziconi et al.
4,836,928 A 6/1989 Aoyagi et al.
4,879,037 A 11/1989 Utzinger
4,895,558 A 1/1990 Cham
4,908,354 A 3/1990 Seidel et al.
4,909,940 A 3/1990 Horowitz et al.
4,909,942 A 3/1990 Sato et al.
4,923,439 A 5/1990 Seidel et al.
4,935,204 A 6/1990 Seidel et al.
4,966,709 A 10/1990 Nose et al.
4,970,144 A 11/1990 Fareed et al.
5,026,479 A 6/1991 Bikson et al.

(Continued)

FOREIGN PATENT DOCUMENTS

CA 1271708 7/1990

(Continued)

OTHER PUBLICATIONS

Desrosiers, R.C. Prospects for an AIDS vaccine, Nature Medicine, Mar. 2004, 10(3):221-223.*

(Continued)

*Primary Examiner*—Stacy B Chen
(74) *Attorney, Agent, or Firm*—Kilpatrick Stockton LLP

(57) ABSTRACT

The present invention relates to a method for reducing the occurrence and severity of infectious diseases, especially infectious diseases in which lipid-containing infectious organisms are found in biological fluids, such as blood. The present invention employs solvents useful for extracting lipids from the lipid-containing infectious organism, thereby reducing the infectivity of the infectious organism. The present invention uses optimal solvent systems such that the lipid envelope around the viral particle is dissolved while the viral particle remains intact, resulting in a modified viral particle. The present invention also provides an autologous vaccine composition, comprising a lipid-containing infectious organism, treated with solvents to reduce the lipid content of the infectious organism, combined with a pharmaceutically acceptable carrier. The vaccine composition is administered to an animal or a human to provide protection against the lipid-containing infectious organism. The present invention further provides a simple, inexpensive and easy to use kit for delipidating fluids and for delipidation of lipid-containing organisms in a fluid.

24 Claims, 4 Drawing Sheets

U.S. PATENT DOCUMENTS

| | | |
|---|---|---|
| 5,080,796 A | 1/1992 | Nose et al. |
| 5,089,602 A | 2/1992 | Isliker et al. |
| 5,112,956 A | 5/1992 | Tang et al. |
| 5,116,307 A | 5/1992 | Collins |
| 5,126,240 A | 6/1992 | Curtiss |
| 5,128,318 A | 7/1992 | Levine et al. |
| 5,152,743 A | 10/1992 | Gorsuch et al. |
| 5,187,010 A | 2/1993 | Parham et al. |
| 5,203,778 A | 4/1993 | Boehringer |
| 5,211,850 A | 5/1993 | Shettigar et al. |
| 5,236,644 A | 8/1993 | Parham et al. |
| 5,256,767 A | 10/1993 | Salk et al. |
| 5,258,149 A | 11/1993 | Parham et al. |
| 5,279,540 A | 1/1994 | Davidson |
| 5,301,694 A | 4/1994 | Raymond et al. |
| 5,354,262 A | 10/1994 | Boehringer et al. |
| 5,391,143 A | 2/1995 | Kensey |
| 5,393,429 A | 2/1995 | Nakayama et al. |
| 5,401,415 A | 3/1995 | Rauh et al. |
| 5,401,466 A | 3/1995 | Foltz et al. |
| 5,418,061 A | 5/1995 | Parham et al. |
| 5,419,759 A | 5/1995 | Naficy |
| 5,424,068 A | 6/1995 | Filip |
| 5,476,715 A | 12/1995 | Otto |
| 5,484,396 A | 1/1996 | Naficy |
| 5,496,637 A | 3/1996 | Parham et al. |
| 5,523,096 A | 6/1996 | Okarma et al. |
| 5,565,203 A | 10/1996 | Gluck et al. |
| 5,634,893 A | 6/1997 | Rishton |
| 5,637,224 A | 6/1997 | Sirkar et al. |
| 5,652,339 A | 7/1997 | Lerch et al. |
| 5,679,260 A | 10/1997 | Boos et al. |
| 5,698,432 A * | 12/1997 | Oxford .................... 435/236 |
| 5,707,673 A | 1/1998 | Prevost et al. |
| 5,719,194 A | 2/1998 | Mann et al. |
| 5,744,038 A | 4/1998 | Cham |
| 5,753,227 A | 5/1998 | Strahilevitz |
| 5,834,015 A | 11/1998 | Oleske et al. |
| 5,853,725 A | 12/1998 | Salk et al. |
| 5,855,782 A | 1/1999 | Falkenhagen et al. |
| 5,858,238 A | 1/1999 | McRea et al. |
| 5,877,005 A | 3/1999 | Castor |
| 5,879,685 A | 3/1999 | Gluck et al. |
| 5,885,578 A | 3/1999 | Salk et al. |
| 5,891,432 A | 4/1999 | Hoo |
| 5,895,650 A | 4/1999 | Salk et al. |
| 5,911,698 A | 6/1999 | Cham |
| 5,916,806 A | 6/1999 | Salk et al. |
| 5,919,369 A | 7/1999 | Ash |
| 5,928,930 A | 7/1999 | Salk et al. |
| 5,948,441 A | 9/1999 | Lenk et al. |
| 5,962,322 A | 10/1999 | Kozarsky et al. |
| 5,980,478 A | 11/1999 | Gorsuch et al. |
| 6,004,925 A | 12/1999 | Dasseux et al. |
| 6,017,543 A | 1/2000 | Salk et al. |
| 6,022,333 A | 2/2000 | Kensev |
| 6,037,323 A | 3/2000 | Dasseux et al. |
| 6,037,458 A | 3/2000 | Hirai et al. |
| 6,039,946 A | 3/2000 | Strahilevitz |
| 6,046,166 A | 4/2000 | Dasseux et al. |
| 6,080,778 A | 6/2000 | Yankner et al. |
| 6,127,370 A | 10/2000 | Smith et al. |
| 6,136,321 A * | 10/2000 | Barrett et al. ............ 424/208.1 |
| 6,139,746 A | 10/2000 | Kopf |
| 6,156,727 A | 12/2000 | Garber et al. |
| 6,165,502 A | 12/2000 | Oleske et al. |
| 6,171,373 B1 | 1/2001 | Park et al. |
| 6,193,891 B1 | 2/2001 | Kent et al. |
| 6,264,623 B1 | 7/2001 | Strahilevitz |
| 6,309,550 B1 | 10/2001 | Iverson et al. |
| 6,337,368 B1 | 1/2002 | Kobayashi et al. |
| 6,369,048 B1 | 4/2002 | Budowsky et al. |
| 6,440,387 B1 | 8/2002 | Yankner et al. |
| 6,472,421 B1 | 10/2002 | Wolozin |
| 6,605,588 B1 | 8/2003 | Lees et al. |
| 6,706,008 B2 | 3/2004 | Vishnoi et al. |
| 6,737,066 B1 | 5/2004 | Moss |
| 2001/0028895 A1 | 10/2001 | Bisgaier et al. |
| 2002/0055529 A1 | 5/2002 | Bisgaier et al. |
| 2002/0081263 A1 | 6/2002 | Yankner et al. |
| 2002/0107173 A1 | 8/2002 | Friedhoff et al. |
| 2002/0128227 A1 | 9/2002 | Hildreth |
| 2002/0183379 A1 | 12/2002 | Yankner et al. |
| 2002/0188012 A1 | 12/2002 | Bisgaier et al. |
| 2003/0018013 A1 | 1/2003 | Dasseux et al. |
| 2003/0044428 A1 | 3/2003 | Moss |
| 2003/0119782 A1 | 6/2003 | Cham et al. |
| 2005/0032222 A1 | 2/2005 | Cham et al. |

FOREIGN PATENT DOCUMENTS

| | | |
|---|---|---|
| CN | 1189378 | 8/1998 |
| DE | 2944138 A1 | 6/1981 |
| DE | 3118072 | 11/1982 |
| DE | 32 13 390 A1 | 10/1983 |
| DE | 3310263 | 9/1984 |
| EP | 1183506 | 3/1970 |
| EP | 0 036 283 A2 | 9/1981 |
| EP | 0 267 471 A1 | 5/1988 |
| FR | 2 571 971 A1 | 4/1986 |
| JP | 127104 | 1/1980 |
| JP | 277303 | 10/1993 |
| SU | 1116396 A | 9/1984 |
| SU | 1204224 A | 1/1986 |
| SU | 1752187 A3 | 7/1992 |
| WO | WO 88/09345 A1 | 12/1988 |
| WO | WO 95/03840 A1 | 2/1995 |
| WO | WO 99/38498 A1 | 8/1999 |
| WO | WO 01/45718 | 6/2001 |
| WO | WO 01/56579 A1 | 8/2001 |
| WO | WO 02/10768 A3 | 2/2002 |
| WO | WO 02/30863 A2 | 4/2002 |
| WO | WO 02/062824 A2 | 8/2002 |

OTHER PUBLICATIONS

Feinberg et al, AIDS vaccine models: Challenging challenge viruses, Nature Medicine, Mar. 2002, 8(3):207-210.*

Albouz, et al., Ann. Biol. Clin., Extraction of Plasma Lipids Preserving Antigenic Properties of Proteins and Allowing Quantitation of Gangliosides by Neuraminic Acid Determination, 37, 287-290. (abstract only) (1979).

Andre et al., Journal of Virology, Characterization of Low- and Very-Low-Density Hepatitis C Virus RNA-Containing Particles, 76 (14), 6919-6928. (Jul. 2002).

Asztalos et al., Arterioscler. Thromb. Vasc. Biol., Distribution of Apo A-I-Containing HDL Subpopulations in Patients with Coronary Heart Disease, 2670-2676. (Dec. 1, 2000).

Asztalos et al., Arterioscler. Thromb. Vasc. Biol., Presence and Formation of 'Free Apolipoprotein A-I-Like' Particles in Human Plasma, 15, 1419-1423. (1995).

Asztalos et al., Arterioscler. Thromb. Vasc. Biol., Role of Free Apolipoprotein A-I in Cholesterol Efflux, 17, 1630-1636. (1997).

Badimon, et al., Laboratory Investigation, High Density Lipoprotein Plasma Fractions Inhibit Aortic Fatty Streaks in Cholesterol-Fed Rabbits, 60, 455-461. (1989).

Badimon, et al., J. Clinical Investigation, Regression of Atherosclerotic Lesions by High Density Lipoprotein Plasma Fraction in the Cholesterol-Fed Rabbit, 85, 1234-1241. (1990).

Barrans et al., Biochimica et Biophysica Acta, Pre-β HDL: Structure and Metabolism, 1300, 73-85. (1996).

Barres et al., Science, Cholesterol—Making or Breaking the Synapse, 294, 1296/1297. (Nov. 9, 2001).

Bloom, et al., Clin. Biochem., Quantitation of lipid profiles from isolated serum lipoproteins using small volumes of human serum, 14, 119-125. (abstract only) (Jun. 1981).

Cham, Clinical Chemistry, Nature of the Interaction Between Low-Density Lipoproteins and Polyanions and Metal Ions, as Exemplified by Heparin and $Ca^{2+}$, 22, 1812-1816. (1976).

Cham, et al., Clinical Chemistry. Changes in Electrophoretic Mobilities of α- and β-Lipoproteins as a Result of Plasma Delipidation, 22, 305-309. (1976).

Cham, et al., Biochemical and Biophysical Research Communications, Heterogeneity of Lipoprotein B, 103, 196-206. (1981).

Cham, et al., Chem. Biol. Interactions, Importance of Apolipoproteins in Lipid Metabolism, 20, 263-277. (1978).

Cham, et al., J. Biol. Chem., In Vitro Partial Relipidation of Apolipoproteins in Plasma, 251, 6367-6371. (abstract only) (1976).

Cham, et al., Pharmacol. (Life Sci. Adv.), Lipid Apheresis in an Animal Model Causes Acute Reduction in plasma Lipid Concentrations and Mobilisation of Lipid from Liver and Aorta, 13, 25-32. (1994).

Cham, et al., J. Clin. Apheresis, Lipid Apheresis in an Animal Model Causes In Vivo Changes in Lipoprotein Electrophoretic Patterns, 11, 61-70. (1996).

Cham, et al., Clinical Chemistry, Phospholipids in EDTA—Treated Plasma and Serum, 39, 2347-2348. (1993).

Cham, et al., 59th Congress European Atherosclerosis Society, Nice, France, Rapid Regression of Atherosclerosis by Cholesterol Apheresis—A Newly Developed Technique, 17-21. (abstract only) (May 1992).

Cham, et al., Clinica Chimica Acta, Rapid, Sensitive Method for the Separation of Free Cholesterol from Ester Cholesterol, 49, 109-113. (1973).

Collet et al., Journal of Biological Chemistry, Differential Effects of Lecithin and Cholesterol on the Immunoreactivity and Confirmation of Apolipoprotein A-I in High Density Lipoproteins, 266 (14), 9145-9152. (May 15, 1991).

Copper, Drugs Aging, Dietary Lipids in the Aetiology of Alzheimer's Disease: Implications for Therapy, 20 (6), 399-418. (abstract only) (2003).

Cruzado et al., Analytical Biochemistry, Characterization and Quantitation of the Apoproteins of High-Density Lipoprotein by Capillary Electrophoresis, 14 (7), 100-109. (1996).

Dwivedy, 18th Australian Atherosclerosis Society Conference, Surfers Paradise, Increase of Reverse Cholesterol Transport by Cholesterol Apheresis Regression of Atherosclerosis, 21. (1992).

Eisenhauer, et al. Klin Wochenschr (KWH), Selective Removal of Low Density Lipoproteins (LDL) by Precipitation at Low pH: First Clinical Application of the HELP System, 65, 161-168. (1987).

Fang, et al., 18th Australian Atherosclerosis Society Conference, Gold Coast, Australia, In Vivo Rapid Mobilization of Adipose Tissue by Lipid Apheresis—A Newly Developed Technique. (1992).

Golde et al., Drug Discovery Today, Cholesterol Modulation as an Emerging Strategy for the Treatment of Alzheimer's Disease, 6 (20), 1049-1055. (abstract only) (Oct. 15, 2001).

Hatch et al., Lipoprotein Analysis, Advances in Lipid Research, Practical Methods for Plasma Lipoprotein Analysis, 6, 1-68. (1968).

Innerarity, et al., Biochemistry, Enhanced Binding by Cultured Human Fibroblast of Apo-E-Containing Lipoproteins as Compared with Low Density Lipoproteins, 17, 1440-1447. (1978).

Jackson et al., Biochimica et Biophysica Acta, Isolation and Characterization of the Major Apolipoprotein from Chicken High Density Lipoproteins, 420, 342-349. (1976).

Koizumi, et al., J. Lipid Research, Behavior of Human Apolipoprotein A-1: Phospho-Lipid and apoHDL: Phospholipid Complexes in Vitro and After Injection into Rabbits, 29, 1405-1415. (1988).

Kostner, et al., XI Internet Symp. on Drugs Affecting Lipid Metabolism, Italy, Increase of APO A1 Concentration in Hypercholesteraemic Chicken after Treatment with a Newly Developed Extracorpreal Lipid Elimination. (May 13, 1992).

Kostner, et al., European Journal of Clinical Investigation, Lecithin-cholesterol acyltransferase actitvity in Normocholesterolaemic and Hypercholesterolaemic Roosters: Modulation by Lipid Apheresis, 27, 212-218. (May 7, 1997).

Koudinov et al., Clin Chim Acta, Alzheimer's Amyloid Beta Interaction with Normal Human Plasma High Density Lipoprotein: Association with Apolipoprotein and Lipids, 270 (2), 75-84. (abstract only) (Feb. 23, 1999).

Koudinov et al., Cell Boil Int., Alzheimer's Soluble Amyloid Beta Protein is Secreted by HepG2 Cells as an Apolipoprotein, 21 (5), 265-71. (abstract only) (May 1997).

Koudinov et al., Biochem Biophys Res Commun, Biochemical Characterization of Alzheimer's Soluble Amyloid Beta Protein in Human Cerebrospinal Fluid: Association with High Density Lipoproteins, 223 (3), 592-7. (abstract only) (Jun. 25, 1999).

Koudinov et al., Science, Cholesterol's Role in Synapse Formation, 294, 2213. (Nov. 9, 2001).

Koudinova et al., Soc. Neuroscience Abstract Viewer and Itinerary Planner, Amyloid Beta, Neural Lipids, Cholesterol and Alzheimer's Disease—Abstract No. 21.10 (2002).

Lipid Sciences, http://www.lipidscience.com/technology.html, Lipid Technology, 1-4. (Aug. 25, 2001).

Lupien, et al., Lancet (LOS), A New Approach to the Management of Familial Hypercholesterolaemia: Removal of Plasma-Cholesterol Based on the Principle of Affinity Chromatography, 1, 1261-1265. (1976).

Mauch et al., Science, CNS Synaptogenesis Promoted by Glia-Derived Cholesterol, 194, 1354-1357. (Nov. 9, 2001).

Moya et al., Arteriosclerosis and Thrombosis, A Cell Culture System for Screening Human Serum for Ability to Promote Cellular Cholesterol Efflux, 14 (7), 1056-1065. (Jul. 1994).

Okazaki et al., Journal of Chromatography, Biomedical Applications, Improved High-Performance Liquid Chromatographic Method for the Determination of Apolopoproteins in Serum High-Density Lipoproteins, 430, 135-142. (1988).

Refolo et al., Soc. Neuroscience Abstract, Cholesterol Metabolism: A Potential Target for Alzheimer's Disease Therapy, 27 (2), 1518. (abstract only) (2001).

Robern et al., Experientia, The Application of Sodium Deoxycholate and Sephacryl-200 for the Delipdation and Separation of High Density Lipoproteins, 38, 437-439. (1982).

Ryan, et al., Clinical Chemistry, An Improved Extraction Procedure for the Determination of Triglycerides and Cholesterol in Plasma or Serum, 13, 769-772. (1967).

Scanu et al., Analytical Biochemistry, Solubility in Aqueous Solutions of Ethanol of the Small Molecular Weight Peptides of the Serum Very Low Density and High Density Lipoproteins: Relevance to the Recovery Problem During Delipidation of Serum Lipoproteins, 44, 576-588. (1971).

Segrest et al., Journal of Biological Chemistry, A Detailed Molecular Belt Model for Apolipoprotein A-I in Discoidal High Density Lipoprotein, 274 (45), 31755-31758. (Nov. 5, 1999).

Slater, et al., J. of Lipid Research, A Comparison of Delipidated Sera Used in Studies of Sterol Synthesis by Human Mononuclear Leukocytes, 20, 413-416. (1979).

Slater, et al., Atherosclerosis, The Effect of Delipidated High Density Lipoprotein on Human Leukocyte Sterol Synthesis, 35, 41-49. (1980).

Thompson, et al., Lancet (LOS), Plasma Exchange in the Management of Homozygous Familial Hypercholesterolaemia, 1, 1208-1211. (1975).

Williams, et al., Proc. Natl. Acad. Sci. USA, Low Denisty Lipoprotein Receptor-Independent Hepatic Uptake of a Synthetic, Cholesterol-Scavenging Lipoprotein: Implication for the Treatment of Receptor-Deficient Atherosclerosis, 85, 242-246. (1988).

Williams et al., Biochim. Biophys. Act., Uptake of Endogenous Cholesterol by a Synthetic Lipoprotein, 875 (2), 183-194. (Feb. 12, 1986).

Wong, et al, Journal of Lipid Research, Retention of gangliosides in serum delipidated by diisopropyl ether-1-butanol extraction, 24, 666-669. (1983).

Wormser, Henry, PSC3110—Fall Semester 2002, Lipids.

Yokoyama, et al., Arteriosclerosis, Selective Removal of Density Lipoprotein by Plasmapheresis in Familial Hypercholesterolemia, 5, 613-622. (1985).

Yoshidome et al., Artif Organs, Serum Amyloid A and P Protein Levels are Lowered by Dextran Sulfate Cellulose Low-Density Lipoprotein Apheresis, 22 (2), 144-148. (1998).

Zhang et al., Journal of Lipid Research, Characterization of phospholipids in a pre-alpha HDL: Selective Phospholipid Efflux with Apolipoprotein A-I , 39, 1601-1607. (1998).

Agnese, S.T., et al., "Evaluation of Four Reagents for Dilipidation of Serum," Clin Biochem., (1983) Apr., vol. 16, No. 2, pp. 98-100.

Cham, Bill E., et al., "Lipid Apheresis: An In Vivo Application of Plasma Delipidation with Organic Solvents Resulting in Acute Transient Reduction of Circulating Plasma Lipids in Animals," Journal of Clinical Apheresis, vol. 10, 1995, pp. 61-69.

Cham, Bill E., et al., "A solvent system for delipidation of plasma of serum without protein precipitation," Journal of Lipid Research, vol. 17, 1976, pp. 176-181.

Deva, A.K., et al., "Establishment of an in-use testing method for evaluating disinfection of surgical instruments using the duck hepatitis B model," J. Hosp., Infect (1996) Jun. vol. 22, No. 2, pp. 119-130, Abstract only.

Feinstone, Stephen M., et al., "Inactivation of Hepatitis B Virus and Non-A, Non-B Hepatitis by Chloroform," Infection and Immunity, Aug. 1983, vol. 41, No. 2, pp. 816-821.

Horowitz, B., et al., "Viral safety of solvent/detergent-treated blood products, Blood Coagulation and Fibrinolysis," vol. 5, Suppl. 3, 1994, pp. S21-S28.

Ngu, V.A., "Chronic Infections from the Perspective of Evolution: a Hypothesis", *Medical Hypotheses*, vol. 42, pp. 81-88 (1994).

Ngu, V.A., "Human Cancers and Viruses: A Hypothesis for Immune Destruction of Tumors Caused by Certain Enveloped Viruses Using Modified Viral Antigens", *Medical Hypotheses*, vol. 39, pp. 17-21 (1992).

Ngu, V.A., "The viral envelope in the evolution of HIV: a hypothetical approach to inducing an effective immune response to the virus", *Medical Hypothesis*, vol. 48, pp. 517-521 (1997).

Parker, Thomas S., et al., "Plasma high density lipoprotein is increased in man when low denisty lipoprotein (LDL) is lowered by LDL-pheresis," Proc. Natl. Acad. Sci. USA, vol. 82, pp. 771-781, Feb. 1986.

Neurath, A. R. et al., "Properties of Delipidated Hepatitis B Surface Antigen (HbsAAg) and Preparation of its Proteolytic Cleavage Fragments Carrying HbsAg-Specific Antigenic Determinants," Intervirology, vol. 10, No. 5, 1978, pp. 265-275.

Klimov, A.N. et al., "Extraction of Lipids From Blood Plasma and Subsequent Introduction of Autologous Delipidized Plasma Into the Body as a Possible Means to Treat Atherosclerosis," English Translation From the Russian Journal Kardiologiia, vol. 18, No. 6, 1978, pp. 23-29.

\* cited by examiner

SEQUENCE LISTING

<160> NUMBER OF SEQ ID NOS: 122

<210> SEQ ID NO 1
<211> LENGTH: 22
<212> TYPE: PRT
<213> ORGANISM: Artificial Sequence
<220> FEATURE:
<223> OTHER INFORMATION: Synthetic

<400> SEQUENCE: 1

Met Gly Val Arg Asn Ser Val Leu Ser Gly Lys Lys Ala Asp Glu Leu
1               5                   10                  15

Glu Lys Ile Arg Leu Arg
            20

<210> SEQ ID NO 2
<211> LENGTH: 22
<212> TYPE: PRT
<213> ORGANISM: Artificial Sequence
<220> FEATURE:
<223> OTHER INFORMATION: Synthetic

<400> SEQUENCE: 2

Lys Lys Ala Asp Glu Leu Glu Lys Ile Arg Leu Arg Pro Asn Gly Lys
1               5                   10                  15

Lys Lys Tyr Met Leu Lys
            20

<210> SEQ ID NO 3
<211> LENGTH: 22
<212> TYPE: PRT
<213> ORGANISM: Artificial Sequence
<220> FEATURE:
<223> OTHER INFORMATION: Synthetic

<400> SEQUENCE: 3

Leu Arg Pro Asn Gly Lys Lys Lys Tyr Met Leu Lys His Val Val Trp
1               5                   10                  15

Ala Ala Asn Glu Leu Asp
            20

<210> SEQ ID NO 4
<211> LENGTH: 22
<212> TYPE: PRT
<213> ORGANISM: Artificial Sequence
<220> FEATURE:
<223> OTHER INFORMATION: Synthetic

<400> SEQUENCE: 4

Leu Lys His Val Val Trp Ala Ala Asn Glu Leu Asp Arg Phe Gly Leu
1               5                   10                  15

Ala Glu Ser Leu Leu Glu
            20

<210> SEQ ID NO 5
<211> LENGTH: 22
<212> TYPE: PRT
<213> ORGANISM: Artificial Sequence
<220> FEATURE:
<223> OTHER INFORMATION: Synthetic

<400> SEQUENCE: 5

Leu Asp Arg Phe Gly Leu Ala Glu Ser Leu Leu Glu Asn Lys Glu Gly

```
                1               5                   10                  15
Cys Gln Lys Ile Leu Ser
                20

<210> SEQ ID NO 6
<211> LENGTH: 22
<212> TYPE: PRT
<213> ORGANISM: Artificial Sequence
<220> FEATURE:
<223> OTHER INFORMATION: Synthetic

<400> SEQUENCE: 6

Leu Glu Asn Lys Glu Gly Cys Gln Lys Ile Leu Ser Val Leu Ala Pro
1               5                   10                  15

Leu Val Pro Thr Gly Ser
                20

<210> SEQ ID NO 7
<211> LENGTH: 22
<212> TYPE: PRT
<213> ORGANISM: Artificial Sequence
<220> FEATURE:
<223> OTHER INFORMATION: Synthetic

<400> SEQUENCE: 7

Leu Ser Val Leu Ala Pro Leu Val Pro Thr Gly Ser Glu Asn Leu Lys
1               5                   10                  15

Ser Leu Tyr Asn Thr Val
                20

<210> SEQ ID NO 8
<211> LENGTH: 22
<212> TYPE: PRT
<213> ORGANISM: Artificial Sequence
<220> FEATURE:
<223> OTHER INFORMATION: Synthetic

<400> SEQUENCE: 8

Gly Ser Glu Asn Leu Lys Ser Leu Tyr Asn Thr Val Cys Val Ile Trp
1               5                   10                  15

Cys Ile His Ala Glu Glu
                20

<210> SEQ ID NO 9
<211> LENGTH: 22
<212> TYPE: PRT
<213> ORGANISM: Artificial Sequence
<220> FEATURE:
<223> OTHER INFORMATION: Synthetic

<400> SEQUENCE: 9

Thr Val Cys Val Ile Trp Cys Ile His Ala Glu Glu Lys Val Lys His
1               5                   10                  15

Thr Glu Glu Ala Lys Gln
                20

<210> SEQ ID NO 10
<211> LENGTH: 22
<212> TYPE: PRT
<213> ORGANISM: Artificial Sequence
<220> FEATURE:
<223> OTHER INFORMATION: Synthetic

<400> SEQUENCE: 10
```

Glu Glu Lys Val Lys His Thr Glu Ala Lys Gln Ile Val Gln Arg
1               5                   10                  15

His Leu Val Val Glu Thr
            20

<210> SEQ ID NO 11
<211> LENGTH: 22
<212> TYPE: PRT
<213> ORGANISM: Artificial Sequence
<220> FEATURE:
<223> OTHER INFORMATION: Synthetic

<400> SEQUENCE: 11

Lys Gln Ile Val Gln Arg His Leu Val Val Glu Thr Gly Thr Thr Glu
1               5                   10                  15

Thr Met Pro Lys Thr Ser
            20

<210> SEQ ID NO 12
<211> LENGTH: 22
<212> TYPE: PRT
<213> ORGANISM: Artificial Sequence
<220> FEATURE:
<223> OTHER INFORMATION: Synthetic

<400> SEQUENCE: 12

Glu Thr Gly Thr Thr Glu Thr Met Pro Lys Thr Ser Arg Pro Thr Ala
1               5                   10                  15

Pro Ser Ser Gly Arg Gly
            20

<210> SEQ ID NO 13
<211> LENGTH: 22
<212> TYPE: PRT
<213> ORGANISM: Artificial Sequence
<220> FEATURE:
<223> OTHER INFORMATION: Synthetic

<400> SEQUENCE: 13

Thr Ser Arg Pro Thr Ala Pro Ser Ser Gly Arg Gly Gly Asn Tyr Pro
1               5                   10                  15

Val Gln Gln Ile Gly Gly
            20

<210> SEQ ID NO 14
<211> LENGTH: 22
<212> TYPE: PRT
<213> ORGANISM: Artificial Sequence
<220> FEATURE:
<223> OTHER INFORMATION: Synthetic

<400> SEQUENCE: 14

Arg Gly Gly Asn Tyr Pro Val Gln Gln Ile Gly Gly Asn Tyr Val His
1               5                   10                  15

Leu Pro Leu Ser Pro Arg
            20

<210> SEQ ID NO 15
<211> LENGTH: 22
<212> TYPE: PRT
<213> ORGANISM: Artificial Sequence
<220> FEATURE:
<223> OTHER INFORMATION: Synthetic

<400> SEQUENCE: 15

-continued

```
Gly Gly Asn Tyr Val His Leu Pro Leu Ser Pro Arg Thr Leu Asn Ala
1               5                   10                  15

Trp Val Lys Leu Ile Glu
            20

<210> SEQ ID NO 16
<211> LENGTH: 22
<212> TYPE: PRT
<213> ORGANISM: Artificial Sequence
<220> FEATURE:
<223> OTHER INFORMATION: Synthetic

<400> SEQUENCE: 16

Pro Arg Thr Leu Asn Ala Trp Val Lys Leu Ile Glu Glu Lys Lys Phe
1               5                   10                  15

Gly Ala Glu Val Val Pro
            20

<210> SEQ ID NO 17
<211> LENGTH: 22
<212> TYPE: PRT
<213> ORGANISM: Artificial Sequence
<220> FEATURE:
<223> OTHER INFORMATION: Synthetic

<400> SEQUENCE: 17

Ile Glu Glu Lys Lys Phe Gly Ala Glu Val Val Pro Gly Phe Gln Ala
1               5                   10                  15

Leu Ser Glu Gly Cys Thr
            20

<210> SEQ ID NO 18
<211> LENGTH: 25
<212> TYPE: PRT
<213> ORGANISM: Artificial Sequence
<220> FEATURE:
<223> OTHER INFORMATION: Synthetic

<400> SEQUENCE: 18

Val Pro Gly Phe Gln Ala Leu Ser Glu Gly Cys Thr Pro Tyr Asp Ile
1               5                   10                  15

Asn Gln Met Leu Asn Cys Val Gly Asp
            20                  25

<210> SEQ ID NO 19
<211> LENGTH: 20
<212> TYPE: PRT
<213> ORGANISM: Artificial Sequence
<220> FEATURE:
<223> OTHER INFORMATION: Synthetic

<400> SEQUENCE: 19

Gly Cys Thr Pro Tyr Asp Ile Asn Gln Met Leu Asn Cys Val Gly Asp
1               5                   10                  15

His Gln Ala Ala
            20

<210> SEQ ID NO 20
<211> LENGTH: 23
<212> TYPE: PRT
<213> ORGANISM: Artificial Sequence
<220> FEATURE:
<223> OTHER INFORMATION: Synthetic
```

```
<400> SEQUENCE: 20

Asn Cys Val Gly Asp His Gln Ala Ala Met Gln Ile Ile Arg Asp Ile
1               5                   10                  15

Ile Asn Glu Glu Ala Ala Asp
            20

<210> SEQ ID NO 21
<211> LENGTH: 22
<212> TYPE: PRT
<213> ORGANISM: Artificial Sequence
<220> FEATURE:
<223> OTHER INFORMATION: Synthetic

<400> SEQUENCE: 21

Ile Ile Arg Asp Ile Ile Asn Glu Glu Ala Ala Asp Trp Asp Leu Gln
1               5                   10                  15

His Pro Gln Pro Ala Pro
            20

<210> SEQ ID NO 22
<211> LENGTH: 22
<212> TYPE: PRT
<213> ORGANISM: Artificial Sequence
<220> FEATURE:
<223> OTHER INFORMATION: Synthetic

<400> SEQUENCE: 22

Ala Asp Trp Asp Leu Gln His Pro Gln Pro Ala Pro Gln Gln Gly Gln
1               5                   10                  15

Leu Arg Glu Pro Ser Gly
            20

<210> SEQ ID NO 23
<211> LENGTH: 22
<212> TYPE: PRT
<213> ORGANISM: Artificial Sequence
<220> FEATURE:
<223> OTHER INFORMATION: Synthetic

<400> SEQUENCE: 23

Ala Pro Gln Gln Gly Gln Leu Arg Glu Pro Ser Gly Ser Asp Ile Ala
1               5                   10                  15

Gly Thr Thr Ser Ser Val
            20

<210> SEQ ID NO 24
<211> LENGTH: 22
<212> TYPE: PRT
<213> ORGANISM: Artificial Sequence
<220> FEATURE:
<223> OTHER INFORMATION: Synthetic

<400> SEQUENCE: 24

Ser Gly Ser Asp Ile Ala Gly Thr Thr Ser Ser Val Asp Glu Gln Ile
1               5                   10                  15

Gln Trp Met Tyr Arg Gln
            20

<210> SEQ ID NO 25
<211> LENGTH: 22
<212> TYPE: PRT
<213> ORGANISM: Artificial Sequence
<220> FEATURE:
<223> OTHER INFORMATION: Synthetic
```

```
<400> SEQUENCE: 25

Ser Val Asp Glu Gln Ile Gln Trp Met Tyr Arg Gln Gln Asn Pro Ile
1               5                   10                  15

Pro Val Gly Asn Ile Tyr
            20

<210> SEQ ID NO 26
<211> LENGTH: 22
<212> TYPE: PRT
<213> ORGANISM: Artificial Sequence
<220> FEATURE:
<223> OTHER INFORMATION: Synthetic

<400> SEQUENCE: 26

Arg Gln Gln Asn Pro Ile Pro Val Gly Asn Ile Tyr Arg Arg Trp Ile
1               5                   10                  15

Gln Leu Gly Leu Gln Lys
            20

<210> SEQ ID NO 27
<211> LENGTH: 23
<212> TYPE: PRT
<213> ORGANISM: Artificial Sequence
<220> FEATURE:
<223> OTHER INFORMATION: Synthetic

<400> SEQUENCE: 27

Ile Tyr Arg Arg Trp Ile Gln Leu Gly Leu Gln Lys Cys Val Arg Met
1               5                   10                  15

Tyr Asn Pro Thr Asn Ile Leu
            20

<210> SEQ ID NO 28
<211> LENGTH: 22
<212> TYPE: PRT
<213> ORGANISM: Artificial Sequence
<220> FEATURE:
<223> OTHER INFORMATION: Synthetic

<400> SEQUENCE: 28

Lys Cys Val Arg Met Tyr Asn Pro Thr Asn Ile Leu Asp Val Lys Gln
1               5                   10                  15

Gly Pro Lys Glu Pro Phe
            20

<210> SEQ ID NO 29
<211> LENGTH: 22
<212> TYPE: PRT
<213> ORGANISM: Artificial Sequence
<220> FEATURE:
<223> OTHER INFORMATION: Synthetic

<400> SEQUENCE: 29

Ile Leu Asp Val Lys Gln Gly Pro Lys Glu Pro Phe Gln Ser Tyr Val
1               5                   10                  15

Asp Arg Phe Tyr Lys Ser
            20

<210> SEQ ID NO 30
<211> LENGTH: 22
<212> TYPE: PRT
<213> ORGANISM: Artificial Sequence
<220> FEATURE:
```

-continued

<223> OTHER INFORMATION: Synthetic

<400> SEQUENCE: 30

Pro Phe Gln Ser Tyr Val Asp Arg Phe Tyr Lys Ser Leu Arg Ala Glu
1               5                   10                  15

Gln Thr Asp Ala Ala Val
            20

<210> SEQ ID NO 31
<211> LENGTH: 22
<212> TYPE: PRT
<213> ORGANISM: Artificial Sequence
<220> FEATURE:
<223> OTHER INFORMATION: Synthetic

<400> SEQUENCE: 31

Lys Ser Leu Arg Ala Glu Gln Thr Asp Ala Ala Val Lys Asn Trp Met
1               5                   10                  15

Thr Gln Thr Leu Leu Ile
            20

<210> SEQ ID NO 32
<211> LENGTH: 22
<212> TYPE: PRT
<213> ORGANISM: Artificial Sequence
<220> FEATURE:
<223> OTHER INFORMATION: Synthetic

<400> SEQUENCE: 32

Ala Val Lys Asn Trp Met Thr Gln Thr Leu Leu Ile Gln Asn Ala Asn
1               5                   10                  15

Pro Asp Cys Lys Leu Val
            20

<210> SEQ ID NO 33
<211> LENGTH: 22
<212> TYPE: PRT
<213> ORGANISM: Artificial Sequence
<220> FEATURE:
<223> OTHER INFORMATION: Synthetic

<400> SEQUENCE: 33

Leu Ile Gln Asn Ala Asn Pro Asp Cys Lys Leu Val Leu Lys Gly Leu
1               5                   10                  15

Gly Val Asn Pro Thr Leu
            20

<210> SEQ ID NO 34
<211> LENGTH: 22
<212> TYPE: PRT
<213> ORGANISM: Artificial Sequence
<220> FEATURE:
<223> OTHER INFORMATION: Synthetic

<400> SEQUENCE: 34

Leu Val Leu Lys Gly Leu Gly Val Asn Pro Thr Leu Glu Glu Met Leu
1               5                   10                  15

Thr Ala Cys Gln Gly Val
            20

<210> SEQ ID NO 35
<211> LENGTH: 22
<212> TYPE: PRT
<213> ORGANISM: Artificial Sequence

```
<220> FEATURE:
<223> OTHER INFORMATION: Synthetic

<400> SEQUENCE: 35

Thr Leu Glu Glu Met Leu Thr Ala Cys Gln Gly Val Gly Gly Pro Gly
1               5                   10                  15

Gln Lys Ala Arg Leu Met
            20

<210> SEQ ID NO 36
<211> LENGTH: 22
<212> TYPE: PRT
<213> ORGANISM: Artificial Sequence
<220> FEATURE:
<223> OTHER INFORMATION: Synthetic

<400> SEQUENCE: 36

Gly Val Gly Gly Pro Gly Gln Lys Ala Arg Leu Met Ala Glu Ala Leu
1               5                   10                  15

Lys Glu Ala Leu Ala Pro
            20

<210> SEQ ID NO 37
<211> LENGTH: 22
<212> TYPE: PRT
<213> ORGANISM: Artificial Sequence
<220> FEATURE:
<223> OTHER INFORMATION: Synthetic

<400> SEQUENCE: 37

Leu Met Ala Glu Ala Leu Lys Glu Ala Leu Ala Pro Val Pro Ile Pro
1               5                   10                  15

Phe Ala Ala Ala Gln Gln
            20

<210> SEQ ID NO 38
<211> LENGTH: 22
<212> TYPE: PRT
<213> ORGANISM: Artificial Sequence
<220> FEATURE:
<223> OTHER INFORMATION: Synthetic

<400> SEQUENCE: 38

Ala Pro Val Pro Ile Pro Phe Ala Ala Ala Gln Gln Arg Gly Pro Arg
1               5                   10                  15

Lys Pro Ile Lys Cys Trp
            20

<210> SEQ ID NO 39
<211> LENGTH: 22
<212> TYPE: PRT
<213> ORGANISM: Artificial Sequence
<220> FEATURE:
<223> OTHER INFORMATION: Synthetic

<400> SEQUENCE: 39

Ala Gln Gln Arg Gly Pro Arg Lys Pro Ile Lys Cys Trp Asn Cys Gly
1               5                   10                  15

Lys Glu Gly His Ser Ala
            20

<210> SEQ ID NO 40
<211> LENGTH: 22
<212> TYPE: PRT
```

```
<213> ORGANISM: Artificial Sequence
<220> FEATURE:
<223> OTHER INFORMATION: Synthetic

<400> SEQUENCE: 40

Lys Cys Trp Asn Cys Gly Lys Glu Gly His Ser Ala Arg Gln Cys Arg
1               5                   10                  15

Ala Pro Arg Gln Gly
            20

<210> SEQ ID NO 41
<211> LENGTH: 22
<212> TYPE: PRT
<213> ORGANISM: Artificial Sequence
<220> FEATURE:
<223> OTHER INFORMATION: Synthetic

<400> SEQUENCE: 41

Ser Ala Arg Gln Cys Arg Ala Pro Arg Gln Gly Cys Trp Lys Cys
1               5                   10                  15

Gly Lys Met Asp His Val
            20

<210> SEQ ID NO 42
<211> LENGTH: 23
<212> TYPE: PRT
<213> ORGANISM: Artificial Sequence
<220> FEATURE:
<223> OTHER INFORMATION: Synthetic

<400> SEQUENCE: 42

Arg Gln Gly Cys Trp Lys Cys Gly Lys Met Asp His Val Met Ala Lys
1               5                   10                  15

Cys Pro Asp Arg Gln Ala Gly
            20

<210> SEQ ID NO 43
<211> LENGTH: 22
<212> TYPE: PRT
<213> ORGANISM: Artificial Sequence
<220> FEATURE:
<223> OTHER INFORMATION: Synthetic

<400> SEQUENCE: 43

His Val Met Ala Lys Cys Pro Asp Arg Gln Ala Gly Phe Leu Gly Leu
1               5                   10                  15

Gly Pro Trp Gly Lys Lys
            20

<210> SEQ ID NO 44
<211> LENGTH: 22
<212> TYPE: PRT
<213> ORGANISM: Artificial Sequence
<220> FEATURE:
<223> OTHER INFORMATION: Synthetic

<400> SEQUENCE: 44

Ala Gly Phe Leu Gly Leu Gly Pro Trp Gly Lys Lys Pro Arg Asn Phe
1               5                   10                  15

Pro Met Ala Gln Val His
            20

<210> SEQ ID NO 45
<211> LENGTH: 22
```

```
<212> TYPE: PRT
<213> ORGANISM: Artificial Sequence
<220> FEATURE:
<223> OTHER INFORMATION: Synthetic

<400> SEQUENCE: 45

Lys Lys Pro Arg Asn Phe Pro Met Ala Gln Val His Gln Gly Leu Met
1               5                   10                  15

Pro Thr Ala Pro Pro Glu
            20

<210> SEQ ID NO 46
<211> LENGTH: 22
<212> TYPE: PRT
<213> ORGANISM: Artificial Sequence
<220> FEATURE:
<223> OTHER INFORMATION: Synthetic

<400> SEQUENCE: 46

Val His Gln Gly Leu Met Pro Thr Ala Pro Pro Glu Asp Pro Ala Val
1               5                   10                  15

Asp Leu Leu Lys Asn Tyr
            20

<210> SEQ ID NO 47
<211> LENGTH: 22
<212> TYPE: PRT
<213> ORGANISM: Artificial Sequence
<220> FEATURE:
<223> OTHER INFORMATION: Synthetic

<400> SEQUENCE: 47

Pro Glu Asp Pro Ala Val Asp Leu Leu Lys Asn Tyr Met Gln Leu Gly
1               5                   10                  15

Lys Gln Gln Arg Glu Lys
            20

<210> SEQ ID NO 48
<211> LENGTH: 22
<212> TYPE: PRT
<213> ORGANISM: Artificial Sequence
<220> FEATURE:
<223> OTHER INFORMATION: Synthetic

<400> SEQUENCE: 48

Asn Tyr Met Gln Leu Gly Lys Gln Gln Arg Glu Lys Gln Arg Glu Ser
1               5                   10                  15

Arg Glu Lys Pro Tyr Lys
            20

<210> SEQ ID NO 49
<211> LENGTH: 22
<212> TYPE: PRT
<213> ORGANISM: Artificial Sequence
<220> FEATURE:
<223> OTHER INFORMATION: Synthetic

<400> SEQUENCE: 49

Glu Lys Gln Arg Glu Ser Arg Glu Lys Pro Tyr Lys Glu Val Thr Glu
1               5                   10                  15

Asp Leu Leu His Leu Asn
            20

<210> SEQ ID NO 50
```

```
<211> LENGTH: 19
<212> TYPE: PRT
<213> ORGANISM: Artificial Sequence
<220> FEATURE:
<223> OTHER INFORMATION: Synthetic

<400> SEQUENCE: 50

Tyr Lys Glu Val Thr Glu Asp Leu Leu His Leu Asn Ser Leu Phe Gly
1               5                   10                  15

Gly Asp Gln

<210> SEQ ID NO 51
<211> LENGTH: 25
<212> TYPE: PRT
<213> ORGANISM: Artificial Sequence
<220> FEATURE:
<223> OTHER INFORMATION: Synthetic

<400> SEQUENCE: 51

Met Gly Cys Leu Gly Asn Gln Leu Leu Ile Ala Ile Leu Leu Leu Ser
1               5                   10                  15

Val Tyr Gly Ile Tyr Cys Thr Leu Tyr
            20                  25

<210> SEQ ID NO 52
<211> LENGTH: 25
<212> TYPE: PRT
<213> ORGANISM: Artificial Sequence
<220> FEATURE:
<223> OTHER INFORMATION: Synthetic

<400> SEQUENCE: 52

Leu Leu Leu Ser Val Tyr Gly Ile Tyr Cys Thr Leu Tyr Val Thr Val
1               5                   10                  15

Phe Tyr Gly Val Pro Ala Trp Arg Asn
            20                  25

<210> SEQ ID NO 53
<211> LENGTH: 25
<212> TYPE: PRT
<213> ORGANISM: Artificial Sequence
<220> FEATURE:
<223> OTHER INFORMATION: Synthetic

<400> SEQUENCE: 53

Tyr Val Thr Val Phe Tyr Gly Val Pro Ala Trp Arg Asn Ala Thr Ile
1               5                   10                  15

Pro Leu Phe Cys Ala Thr Lys Asn Arg
            20                  25

<210> SEQ ID NO 54
<211> LENGTH: 25
<212> TYPE: PRT
<213> ORGANISM: Artificial Sequence
<220> FEATURE:
<223> OTHER INFORMATION: Synthetic

<400> SEQUENCE: 54

Asn Ala Thr Ile Pro Leu Phe Cys Ala Thr Lys Asn Arg Asp Thr Trp
1               5                   10                  15

Gly Thr Thr Gln Cys Leu Pro Asp Asn
            20                  25

<210> SEQ ID NO 55
```

<211> LENGTH: 25
<212> TYPE: PRT
<213> ORGANISM: Artificial Sequence
<220> FEATURE:
<223> OTHER INFORMATION: Synthetic

<400> SEQUENCE: 55

Arg Asp Thr Trp Gly Thr Thr Gln Cys Leu Pro Asp Asn Gly Asp Tyr
1               5                   10                  15
Ser Glu Val Ala Leu Asn Val Thr Glu
            20                  25

<210> SEQ ID NO 56
<211> LENGTH: 25
<212> TYPE: PRT
<213> ORGANISM: Artificial Sequence
<220> FEATURE:
<223> OTHER INFORMATION: Synthetic

<400> SEQUENCE: 56

Asn Gly Asp Tyr Ser Glu Val Ala Leu Asn Val Thr Glu Ser Phe Asp
1               5                   10                  15
Ala Trp Asn Asn Thr Val Thr Glu Gln
            20                  25

<210> SEQ ID NO 57
<211> LENGTH: 25
<212> TYPE: PRT
<213> ORGANISM: Artificial Sequence
<220> FEATURE:
<223> OTHER INFORMATION: Synthetic

<400> SEQUENCE: 57

Glu Ser Phe Asp Ala Trp Asn Asn Thr Val Thr Glu Gln Ala Ile Glu
1               5                   10                  15
Asp Val Trp Gln Leu Phe Glu Thr Ser
            20                  25

<210> SEQ ID NO 58
<211> LENGTH: 25
<212> TYPE: PRT
<213> ORGANISM: Artificial Sequence
<220> FEATURE:
<223> OTHER INFORMATION: Synthetic

<400> SEQUENCE: 58

Gln Ala Ile Glu Asp Val Trp Gln Leu Phe Glu Thr Ser Ile Lys Pro
1               5                   10                  15
Cys Val Lys Leu Ser Pro Leu Cys Ile
            20                  25

<210> SEQ ID NO 59
<211> LENGTH: 25
<212> TYPE: PRT
<213> ORGANISM: Artificial Sequence
<220> FEATURE:
<223> OTHER INFORMATION: Synthetic

<400> SEQUENCE: 59

Ser Ile Lys Pro Cys Val Lys Leu Ser Pro Leu Cys Ile Thr Met Arg
1               5                   10                  15
Cys Asn Lys Ser Glu Thr Asp Arg Trp
            20                  25

```
<210> SEQ ID NO 60
<211> LENGTH: 24
<212> TYPE: PRT
<213> ORGANISM: Artificial Sequence
<220> FEATURE:
<223> OTHER INFORMATION: Synthetic

<400> SEQUENCE: 60

Thr Met Arg Cys Asn Lys Ser Glu Thr Asp Arg Trp Gly Leu Thr Lys
1               5                   10                  15

Ser Ile Thr Thr Thr Ala Ser Thr
            20

<210> SEQ ID NO 61
<211> LENGTH: 25
<212> TYPE: PRT
<213> ORGANISM: Artificial Sequence
<220> FEATURE:
<223> OTHER INFORMATION: Synthetic

<400> SEQUENCE: 61

Trp Gly Leu Thr Lys Ser Ile Thr Thr Thr Ala Ser Thr Thr Ser Thr
1               5                   10                  15

Thr Ala Ser Ala Lys Val Asp Met Val
            20                  25

<210> SEQ ID NO 62
<211> LENGTH: 25
<212> TYPE: PRT
<213> ORGANISM: Artificial Sequence
<220> FEATURE:
<223> OTHER INFORMATION: Synthetic

<400> SEQUENCE: 62

Thr Thr Ser Thr Thr Ala Ser Ala Lys Val Asp Met Val Asn Glu Thr
1               5                   10                  15

Ser Ser Cys Ile Ala Gln Asp Asn Cys
            20                  25

<210> SEQ ID NO 63
<211> LENGTH: 25
<212> TYPE: PRT
<213> ORGANISM: Artificial Sequence
<220> FEATURE:
<223> OTHER INFORMATION: Synthetic

<400> SEQUENCE: 63

Val Asn Glu Thr Ser Ser Cys Ile Ala Gln Asp Asn Cys Thr Gly Leu
1               5                   10                  15

Glu Gln Glu Gln Met Ile Ser Cys Lys
            20                  25

<210> SEQ ID NO 64
<211> LENGTH: 25
<212> TYPE: PRT
<213> ORGANISM: Artificial Sequence
<220> FEATURE:
<223> OTHER INFORMATION: Synthetic

<400> SEQUENCE: 64

Cys Thr Gly Leu Glu Gln Glu Gln Met Ile Ser Cys Lys Phe Asn Met
1               5                   10                  15

Thr Gly Leu Lys Arg Asp Lys Lys
            20                  25
```

```
<210> SEQ ID NO 65
<211> LENGTH: 25
<212> TYPE: PRT
<213> ORGANISM: Artificial Sequence
<220> FEATURE:
<223> OTHER INFORMATION: Synthetic

<400> SEQUENCE: 65

Lys Phe Asn Met Thr Gly Leu Lys Arg Asp Lys Lys Glu Tyr Asn
1               5                   10                  15

Glu Thr Trp Tyr Ser Ala Asp Leu Val
            20                  25

<210> SEQ ID NO 66
<211> LENGTH: 25
<212> TYPE: PRT
<213> ORGANISM: Artificial Sequence
<220> FEATURE:
<223> OTHER INFORMATION: Synthetic

<400> SEQUENCE: 66

Lys Glu Tyr Asn Glu Thr Trp Tyr Ser Ala Asp Leu Val Cys Glu Gln
1               5                   10                  15

Gly Asn Asn Thr Gly Asn Glu Ser Arg
            20                  25

<210> SEQ ID NO 67
<211> LENGTH: 25
<212> TYPE: PRT
<213> ORGANISM: Artificial Sequence
<220> FEATURE:
<223> OTHER INFORMATION: Synthetic

<400> SEQUENCE: 67

Val Cys Glu Gln Gly Asn Asn Thr Gly Asn Glu Ser Arg Cys Tyr Met
1               5                   10                  15

Asn His Cys Asn Thr Ser Val Ile Gln
            20                  25

<210> SEQ ID NO 68
<211> LENGTH: 25
<212> TYPE: PRT
<213> ORGANISM: Artificial Sequence
<220> FEATURE:
<223> OTHER INFORMATION: Synthetic

<400> SEQUENCE: 68

Arg Cys Tyr Met Asn His Cys Asn Thr Ser Val Ile Gln Glu Ser Cys
1               5                   10                  15

Asp Lys His Tyr Trp Asp Ala Ile Arg
            20                  25

<210> SEQ ID NO 69
<211> LENGTH: 25
<212> TYPE: PRT
<213> ORGANISM: Artificial Sequence
<220> FEATURE:
<223> OTHER INFORMATION: Synthetic

<400> SEQUENCE: 69

Gln Glu Ser Cys Asp Lys His Tyr Trp Asp Ala Ile Arg Phe Arg Tyr
1               5                   10                  15

Cys Ala Pro Pro Gly Tyr Ala Leu Leu
            20                  25
```

<210> SEQ ID NO 70
<211> LENGTH: 25
<212> TYPE: PRT
<213> ORGANISM: Artificial Sequence
<220> FEATURE:
<223> OTHER INFORMATION: Synthetic

<400> SEQUENCE: 70

Arg Phe Arg Tyr Cys Ala Pro Pro Gly Tyr Ala Leu Leu Arg Cys Asn
1               5                   10                  15

Asp Thr Asn Tyr Ser Gly Phe Met Pro
            20                  25

<210> SEQ ID NO 71
<211> LENGTH: 25
<212> TYPE: PRT
<213> ORGANISM: Artificial Sequence
<220> FEATURE:
<223> OTHER INFORMATION: Synthetic

<400> SEQUENCE: 71

Leu Arg Cys Asn Asp Thr Asn Tyr Ser Gly Phe Met Pro Lys Cys Ser
1               5                   10                  15

Lys Val Val Ser Ser Cys Thr Arg
            20                  25

<210> SEQ ID NO 72
<211> LENGTH: 25
<212> TYPE: PRT
<213> ORGANISM: Artificial Sequence
<220> FEATURE:
<223> OTHER INFORMATION: Synthetic

<400> SEQUENCE: 72

Pro Lys Cys Ser Lys Val Val Val Ser Ser Cys Thr Arg Met Met Glu
1               5                   10                  15

Thr Gln Thr Ser Thr Trp Phe Gly Phe
            20                  25

<210> SEQ ID NO 73
<211> LENGTH: 25
<212> TYPE: PRT
<213> ORGANISM: Artificial Sequence
<220> FEATURE:
<223> OTHER INFORMATION: Synthetic

<400> SEQUENCE: 73

Arg Met Met Glu Thr Gln Thr Ser Thr Trp Phe Gly Phe Asn Gly Thr
1               5                   10                  15

Arg Ala Glu Asn Arg Thr Tyr Ile Tyr
            20                  25

<210> SEQ ID NO 74
<211> LENGTH: 25
<212> TYPE: PRT
<213> ORGANISM: Artificial Sequence
<220> FEATURE:
<223> OTHER INFORMATION: Synthetic

<400> SEQUENCE: 74

Phe Asn Gly Thr Arg Ala Glu Asn Arg Thr Tyr Ile Tyr Trp His Gly
1               5                   10                  15

Arg Asp Asn Arg Thr Ile Ile Ser Leu

<210> SEQ ID NO 75
<211> LENGTH: 25
<212> TYPE: PRT
<213> ORGANISM: Artificial Sequence
<220> FEATURE:
<223> OTHER INFORMATION: Synthetic

<400> SEQUENCE: 75

Tyr Trp His Gly Arg Asp Asn Arg Thr Ile Ile Ser Leu Asn Lys Tyr
1               5                   10                  15

Tyr Asn Leu Thr Met Lys Cys Arg Arg
            20                  25

<210> SEQ ID NO 76
<211> LENGTH: 25
<212> TYPE: PRT
<213> ORGANISM: Artificial Sequence
<220> FEATURE:
<223> OTHER INFORMATION: Synthetic

<400> SEQUENCE: 76

Leu Asn Lys Tyr Tyr Asn Leu Thr Met Lys Cys Arg Arg Pro Gly Asn
1               5                   10                  15

Lys Thr Val Leu Pro Val Thr Ile Met
            20                  25

<210> SEQ ID NO 77
<211> LENGTH: 25
<212> TYPE: PRT
<213> ORGANISM: Artificial Sequence
<220> FEATURE:
<223> OTHER INFORMATION: Synthetic

<400> SEQUENCE: 77

Arg Pro Gly Asn Lys Thr Val Leu Pro Val Thr Ile Met Ser Gly Leu
1               5                   10                  15

Val Phe His Ser Gln Pro Ile Asn Asp
            20                  25

<210> SEQ ID NO 78
<211> LENGTH: 25
<212> TYPE: PRT
<213> ORGANISM: Artificial Sequence
<220> FEATURE:
<223> OTHER INFORMATION: Synthetic

<400> SEQUENCE: 78

Met Ser Gly Leu Val Phe His Ser Gln Pro Ile Asn Asp Arg Pro Lys
1               5                   10                  15

Gln Ala Trp Cys Trp Phe Gly Gly Lys
            20                  25

<210> SEQ ID NO 79
<211> LENGTH: 25
<212> TYPE: PRT
<213> ORGANISM: Artificial Sequence
<220> FEATURE:
<223> OTHER INFORMATION: Synthetic

<400> SEQUENCE: 79

Asp Arg Pro Lys Gln Ala Trp Cys Trp Phe Gly Gly Lys Trp Lys Asp
1               5                   10                  15

```
Ala Ile Lys Glu Val Lys Gln Thr Ile
            20              25

<210> SEQ ID NO 80
<211> LENGTH: 25
<212> TYPE: PRT
<213> ORGANISM: Artificial Sequence
<220> FEATURE:
<223> OTHER INFORMATION: Synthetic

<400> SEQUENCE: 80

Lys Trp Lys Asp Ala Ile Lys Glu Val Lys Gln Thr Ile Val Lys His
1               5                   10                  15

Pro Arg Tyr Thr Gly Thr Asn Asn Thr
            20              25

<210> SEQ ID NO 81
<211> LENGTH: 25
<212> TYPE: PRT
<213> ORGANISM: Artificial Sequence
<220> FEATURE:
<223> OTHER INFORMATION: Synthetic

<400> SEQUENCE: 81

Ile Val Lys His Pro Arg Tyr Thr Gly Thr Asn Asn Thr Asp Lys Ile
1               5                   10                  15

Asn Leu Thr Ala Pro Gly Gly Gly Asp
            20              25

<210> SEQ ID NO 82
<211> LENGTH: 25
<212> TYPE: PRT
<213> ORGANISM: Artificial Sequence
<220> FEATURE:
<223> OTHER INFORMATION: Synthetic

<400> SEQUENCE: 82

Thr Asp Lys Ile Asn Leu Thr Ala Pro Gly Gly Gly Asp Pro Glu Val
1               5                   10                  15

Thr Phe Met Trp Thr Asn Cys Arg Gly
            20              25

<210> SEQ ID NO 83
<211> LENGTH: 25
<212> TYPE: PRT
<213> ORGANISM: Artificial Sequence
<220> FEATURE:
<223> OTHER INFORMATION: Synthetic

<400> SEQUENCE: 83

Asp Pro Glu Val Thr Phe Met Trp Thr Asn Cys Arg Gly Glu Phe Leu
1               5                   10                  15

Tyr Cys Lys Met Asn Trp Phe Leu Asn
            20              25

<210> SEQ ID NO 84
<211> LENGTH: 25
<212> TYPE: PRT
<213> ORGANISM: Artificial Sequence
<220> FEATURE:
<223> OTHER INFORMATION: Synthetic

<400> SEQUENCE: 84

Gly Glu Phe Leu Tyr Cys Lys Met Asn Trp Phe Leu Asn Trp Val Glu
1               5                   10                  15
```

```
Asp Arg Asn Thr Ala Asn Gln Lys Pro
            20                  25

<210> SEQ ID NO 85
<211> LENGTH: 25
<212> TYPE: PRT
<213> ORGANISM: Artificial Sequence
<220> FEATURE:
<223> OTHER INFORMATION: Synthetic

<400> SEQUENCE: 85

Asn Trp Val Glu Asp Arg Asn Thr Ala Asn Gln Lys Pro Lys Glu Gln
1               5                   10                  15

His Lys Arg Asn Tyr Val Pro Cys His
            20                  25

<210> SEQ ID NO 86
<211> LENGTH: 25
<212> TYPE: PRT
<213> ORGANISM: Artificial Sequence
<220> FEATURE:
<223> OTHER INFORMATION: Synthetic

<400> SEQUENCE: 86

Pro Lys Glu Gln His Lys Arg Asn Tyr Val Pro Cys His Ile Arg Gln
1               5                   10                  15

Ile Ile Asn Thr Trp His Lys Val Gly
            20                  25

<210> SEQ ID NO 87
<211> LENGTH: 25
<212> TYPE: PRT
<213> ORGANISM: Artificial Sequence
<220> FEATURE:
<223> OTHER INFORMATION: Synthetic

<400> SEQUENCE: 87

His Ile Arg Gln Ile Ile Asn Thr Trp His Lys Val Gly Lys Asn Val
1               5                   10                  15

Tyr Leu Pro Pro Arg Glu Gly Asp Leu
            20                  25

<210> SEQ ID NO 88
<211> LENGTH: 25
<212> TYPE: PRT
<213> ORGANISM: Artificial Sequence
<220> FEATURE:
<223> OTHER INFORMATION: Synthetic

<400> SEQUENCE: 88

Gly Lys Asn Val Tyr Leu Pro Pro Arg Glu Gly Asp Leu Thr Cys Asn
1               5                   10                  15

Ser Thr Val Thr Ser Leu Ile Ala Asn
            20                  25

<210> SEQ ID NO 89
<211> LENGTH: 25
<212> TYPE: PRT
<213> ORGANISM: Artificial Sequence
<220> FEATURE:
<223> OTHER INFORMATION: Synthetic

<400> SEQUENCE: 89

Leu Thr Cys Asn Ser Thr Val Thr Ser Leu Ile Ala Asn Ile Asp Trp
```

```
Ile Asp Gly Asn Gln Thr Asn Ile Thr
            20                  25
```

<210> SEQ ID NO 90
<211> LENGTH: 25
<212> TYPE: PRT
<213> ORGANISM: Artificial Sequence
<220> FEATURE:
<223> OTHER INFORMATION: Synthetic
<400> SEQUENCE: 90

```
Asn Ile Asp Trp Ile Asp Gly Asn Gln Thr Asn Ile Thr Met Ser Ala
1               5                   10                  15
Glu Val Ala Glu Leu Tyr Arg Leu Glu
            20                  25
```

<210> SEQ ID NO 91
<211> LENGTH: 25
<212> TYPE: PRT
<213> ORGANISM: Artificial Sequence
<220> FEATURE:
<223> OTHER INFORMATION: Synthetic
<400> SEQUENCE: 91

```
Thr Met Ser Ala Glu Val Ala Glu Leu Tyr Arg Leu Glu Leu Gly Asp
1               5                   10                  15
Tyr Lys Leu Val Glu Ile Thr Pro Ile
            20                  25
```

<210> SEQ ID NO 92
<211> LENGTH: 25
<212> TYPE: PRT
<213> ORGANISM: Artificial Sequence
<220> FEATURE:
<223> OTHER INFORMATION: Synthetic
<400> SEQUENCE: 92

```
Glu Leu Gly Asp Tyr Lys Leu Val Glu Ile Thr Pro Ile Gly Leu Ala
1               5                   10                  15
Pro Thr Asp Val Lys Arg Tyr Thr Thr
            20                  25
```

<210> SEQ ID NO 93
<211> LENGTH: 25
<212> TYPE: PRT
<213> ORGANISM: Artificial Sequence
<220> FEATURE:
<223> OTHER INFORMATION: Synthetic
<400> SEQUENCE: 93

```
Ile Gly Leu Ala Pro Thr Asp Val Lys Arg Tyr Thr Thr Gly Gly Thr
1               5                   10                  15
Ser Arg Asn Lys Arg Gly Val Phe Val
            20                  25
```

<210> SEQ ID NO 94
<211> LENGTH: 25
<212> TYPE: PRT
<213> ORGANISM: Artificial Sequence
<220> FEATURE:
<223> OTHER INFORMATION: Synthetic
<400> SEQUENCE: 94

```
Thr Gly Gly Thr Ser Arg Asn Lys Arg Gly Val Phe Val Leu Gly Phe
1               5                   10                  15

Leu Gly Phe Leu Ala Thr Ala Gly Ser
            20                  25

<210> SEQ ID NO 95
<211> LENGTH: 25
<212> TYPE: PRT
<213> ORGANISM: Artificial Sequence
<220> FEATURE:
<223> OTHER INFORMATION: Synthetic

<400> SEQUENCE: 95

Val Leu Gly Phe Leu Gly Phe Leu Ala Thr Ala Gly Ser Ala Met Gly
1               5                   10                  15

Ala Ala Ser Leu Thr Leu Thr Ala Gln
            20                  25

<210> SEQ ID NO 96
<211> LENGTH: 25
<212> TYPE: PRT
<213> ORGANISM: Artificial Sequence
<220> FEATURE:
<223> OTHER INFORMATION: Synthetic

<400> SEQUENCE: 96

Ser Ala Met Gly Ala Ala Ser Leu Thr Leu Thr Ala Gln Ser Arg Thr
1               5                   10                  15

Leu Leu Ala Gly Ile Val Gln Gln Gln
            20                  25

<210> SEQ ID NO 97
<211> LENGTH: 25
<212> TYPE: PRT
<213> ORGANISM: Artificial Sequence
<220> FEATURE:
<223> OTHER INFORMATION: Synthetic

<400> SEQUENCE: 97

Gln Ser Arg Thr Leu Leu Ala Gly Ile Val Gln Gln Gln Gln Gln Leu
1               5                   10                  15

Leu Asp Val Val Lys Arg Gln Gln Glu
            20                  25

<210> SEQ ID NO 98
<211> LENGTH: 25
<212> TYPE: PRT
<213> ORGANISM: Artificial Sequence
<220> FEATURE:
<223> OTHER INFORMATION: Synthetic

<400> SEQUENCE: 98

Gln Gln Gln Leu Leu Asp Val Val Lys Arg Gln Gln Glu Leu Leu Arg
1               5                   10                  15

Leu Thr Val Trp Gly Thr Lys Asn Leu
            20                  25

<210> SEQ ID NO 99
<211> LENGTH: 25
<212> TYPE: PRT
<213> ORGANISM: Artificial Sequence
<220> FEATURE:
<223> OTHER INFORMATION: Synthetic

<400> SEQUENCE: 99
```

```
Glu Leu Leu Arg Leu Thr Val Trp Gly Thr Lys Asn Leu Gln Thr Arg
 1               5                  10                  15

Val Thr Ala Ile Glu Lys Tyr Leu Lys
             20                  25

<210> SEQ ID NO 100
<211> LENGTH: 25
<212> TYPE: PRT
<213> ORGANISM: Artificial Sequence
<220> FEATURE:
<223> OTHER INFORMATION: Synthetic

<400> SEQUENCE: 100

Leu Gln Thr Arg Val Thr Ala Ile Glu Lys Tyr Leu Lys Asp Gln Ala
 1               5                  10                  15

Gln Leu Asn Ala Trp Gly Cys Ala Phe
             20                  25

<210> SEQ ID NO 101
<211> LENGTH: 25
<212> TYPE: PRT
<213> ORGANISM: Artificial Sequence
<220> FEATURE:
<223> OTHER INFORMATION: Synthetic

<400> SEQUENCE: 101

Lys Asp Gln Ala Gln Leu Asn Ala Trp Gly Cys Ala Phe Arg Gln Val
 1               5                  10                  15

Cys His Thr Thr Val Pro Trp Pro Asn
             20                  25

<210> SEQ ID NO 102
<211> LENGTH: 25
<212> TYPE: PRT
<213> ORGANISM: Artificial Sequence
<220> FEATURE:
<223> OTHER INFORMATION: Synthetic

<400> SEQUENCE: 102

Phe Arg Gln Val Cys His Thr Thr Val Pro Trp Pro Asn Ala Ser Leu
 1               5                  10                  15

Thr Pro Lys Trp Asn Asn Glu Thr Trp
             20                  25

<210> SEQ ID NO 103
<211> LENGTH: 25
<212> TYPE: PRT
<213> ORGANISM: Artificial Sequence
<220> FEATURE:
<223> OTHER INFORMATION: Synthetic

<400> SEQUENCE: 103

Asn Ala Ser Leu Thr Pro Lys Trp Asn Asn Glu Thr Trp Gln Glu Trp
 1               5                  10                  15

Glu Arg Lys Val Asp Phe Leu Glu Glu
             20                  25

<210> SEQ ID NO 104
<211> LENGTH: 25
<212> TYPE: PRT
<213> ORGANISM: Artificial Sequence
<220> FEATURE:
<223> OTHER INFORMATION: Synthetic
```

```
<400> SEQUENCE: 104

Trp Gln Glu Trp Glu Arg Lys Val Asp Phe Leu Glu Glu Asn Ile Thr
1               5                   10                  15

Ala Leu Leu Glu Glu Ala Gln Ile Gln
            20                  25

<210> SEQ ID NO 105
<211> LENGTH: 25
<212> TYPE: PRT
<213> ORGANISM: Artificial Sequence
<220> FEATURE:
<223> OTHER INFORMATION: Synthetic

<400> SEQUENCE: 105

Glu Asn Ile Thr Ala Leu Leu Glu Glu Ala Gln Ile Gln Gln Glu Lys
1               5                   10                  15

Asn Met Tyr Glu Leu Gln Lys Leu Asn
            20                  25

<210> SEQ ID NO 106
<211> LENGTH: 25
<212> TYPE: PRT
<213> ORGANISM: Artificial Sequence
<220> FEATURE:
<223> OTHER INFORMATION: Synthetic

<400> SEQUENCE: 106

Gln Gln Glu Lys Asn Met Tyr Glu Leu Gln Lys Leu Asn Ser Trp Asp
1               5                   10                  15

Val Phe Gly Asn Trp Phe Asp Leu Ala
            20                  25

<210> SEQ ID NO 107
<211> LENGTH: 25
<212> TYPE: PRT
<213> ORGANISM: Artificial Sequence
<220> FEATURE:
<223> OTHER INFORMATION: Synthetic

<400> SEQUENCE: 107

Asn Ser Trp Asp Val Phe Gly Asn Trp Phe Asp Leu Ala Ser Trp Ile
1               5                   10                  15

Lys Tyr Ile Gln Tyr Gly Val Tyr Ile
            20                  25

<210> SEQ ID NO 108
<211> LENGTH: 25
<212> TYPE: PRT
<213> ORGANISM: Artificial Sequence
<220> FEATURE:
<223> OTHER INFORMATION: Synthetic

<400> SEQUENCE: 108

Ala Ser Trp Ile Lys Tyr Ile Gln Tyr Gly Val Tyr Ile Val Val Gly
1               5                   10                  15

Val Ile Leu Leu Arg Ile Val Ile Tyr
            20                  25

<210> SEQ ID NO 109
<211> LENGTH: 25
<212> TYPE: PRT
<213> ORGANISM: Artificial Sequence
<220> FEATURE:
<223> OTHER INFORMATION: Synthetic
```

-continued

```
<400> SEQUENCE: 109

Ile Val Val Gly Val Ile Leu Leu Arg Ile Val Ile Tyr Ile Val Gln
1               5                   10                  15

Met Leu Ala Lys Leu Arg Gln Gly Tyr
            20                  25

<210> SEQ ID NO 110
<211> LENGTH: 25
<212> TYPE: PRT
<213> ORGANISM: Artificial Sequence
<220> FEATURE:
<223> OTHER INFORMATION: Synthetic

<400> SEQUENCE: 110

Tyr Ile Val Gln Met Leu Ala Lys Leu Arg Gln Gly Tyr Arg Pro Val
1               5                   10                  15

Phe Ser Ser Pro Pro Ser Tyr Phe Gln
            20                  25

<210> SEQ ID NO 111
<211> LENGTH: 25
<212> TYPE: PRT
<213> ORGANISM: Artificial Sequence
<220> FEATURE:
<223> OTHER INFORMATION: Synthetic

<400> SEQUENCE: 111

Tyr Arg Pro Val Phe Ser Ser Pro Pro Ser Tyr Phe Gln Gln Thr His
1               5                   10                  15

Ile Gln Gln Asp Pro Ala Leu Pro Thr
            20                  25

<210> SEQ ID NO 112
<211> LENGTH: 25
<212> TYPE: PRT
<213> ORGANISM: Artificial Sequence
<220> FEATURE:
<223> OTHER INFORMATION: Synthetic

<400> SEQUENCE: 112

Gln Gln Thr His Ile Gln Gln Asp Pro Ala Leu Pro Thr Arg Glu Gly
1               5                   10                  15

Lys Glu Arg Asp Gly Gly Glu Gly Gly
            20                  25

<210> SEQ ID NO 113
<211> LENGTH: 25
<212> TYPE: PRT
<213> ORGANISM: Artificial Sequence
<220> FEATURE:
<223> OTHER INFORMATION: Synthetic

<400> SEQUENCE: 113

Thr Arg Glu Gly Lys Glu Arg Asp Gly Gly Glu Gly Gly Asn Ser
1               5                   10                  15

Ser Trp Pro Trp Gln Ile Glu Tyr Ile
            20                  25

<210> SEQ ID NO 114
<211> LENGTH: 25
<212> TYPE: PRT
<213> ORGANISM: Artificial Sequence
<220> FEATURE:
```

<223> OTHER INFORMATION: Synthetic

<400> SEQUENCE: 114

Gly Gly Asn Ser Ser Trp Pro Trp Gln Ile Glu Tyr Ile His Phe Leu
1               5                   10                  15

Ile Arg Gln Leu Ile Arg Leu Leu Thr
            20                  25

<210> SEQ ID NO 115
<211> LENGTH: 25
<212> TYPE: PRT
<213> ORGANISM: Artificial Sequence
<220> FEATURE:
<223> OTHER INFORMATION: Synthetic

<400> SEQUENCE: 115

Ile His Phe Leu Ile Arg Gln Leu Ile Arg Leu Leu Thr Trp Leu Phe
1               5                   10                  15

Ser Asn Cys Arg Thr Leu Leu Ser Arg
            20                  25

<210> SEQ ID NO 116
<211> LENGTH: 25
<212> TYPE: PRT
<213> ORGANISM: Artificial Sequence
<220> FEATURE:
<223> OTHER INFORMATION: Synthetic

<400> SEQUENCE: 116

Thr Trp Leu Phe Ser Asn Cys Arg Thr Leu Leu Ser Arg Val Tyr Gln
1               5                   10                  15

Ile Leu Gln Pro Ile Leu Gln Arg Leu
            20                  25

<210> SEQ ID NO 117
<211> LENGTH: 25
<212> TYPE: PRT
<213> ORGANISM: Artificial Sequence
<220> FEATURE:
<223> OTHER INFORMATION: Synthetic

<400> SEQUENCE: 117

Arg Val Tyr Gln Ile Leu Gln Pro Ile Leu Gln Arg Leu Ser Ala Thr
1               5                   10                  15

Leu Gln Arg Ile Arg Glu Val Leu Arg
            20                  25

<210> SEQ ID NO 118
<211> LENGTH: 25
<212> TYPE: PRT
<213> ORGANISM: Artificial Sequence
<220> FEATURE:
<223> OTHER INFORMATION: Synthetic

<400> SEQUENCE: 118

Leu Ser Ala Thr Leu Gln Arg Ile Arg Glu Val Leu Arg Thr Glu Leu
1               5                   10                  15

Thr Tyr Leu Gln Tyr Gly Trp Ser Tyr
            20                  25

<210> SEQ ID NO 119
<211> LENGTH: 25
<212> TYPE: PRT
<213> ORGANISM: Artificial Sequence

```
<220> FEATURE:
<223> OTHER INFORMATION: Synthetic

<400> SEQUENCE: 119

Arg Thr Glu Leu Thr Tyr Leu Gln Tyr Gly Trp Ser Tyr Phe His Glu
1               5                   10                  15

Ala Val Gln Ala Val Trp Arg Ser Ala
            20                  25

<210> SEQ ID NO 120
<211> LENGTH: 25
<212> TYPE: PRT
<213> ORGANISM: Artificial Sequence
<220> FEATURE:
<223> OTHER INFORMATION: Synthetic

<400> SEQUENCE: 120

Tyr Phe His Glu Ala Val Gln Ala Val Trp Arg Ser Ala Thr Glu Thr
1               5                   10                  15

Leu Ala Gly Ala Trp Gly Asp Leu Trp
            20                  25

<210> SEQ ID NO 121
<211> LENGTH: 25
<212> TYPE: PRT
<213> ORGANISM: Artificial Sequence
<220> FEATURE:
<223> OTHER INFORMATION: Synthetic

<400> SEQUENCE: 121

Ala Thr Glu Thr Leu Ala Gly Ala Trp Gly Asp Leu Trp Glu Thr Leu
1               5                   10                  15

Arg Arg Gly Gly Arg Trp Ile Leu Ala
            20                  25

<210> SEQ ID NO 122
<211> LENGTH: 27
<212> TYPE: PRT
<213> ORGANISM: Artificial Sequence
<220> FEATURE:
<223> OTHER INFORMATION: Synthetic

<400> SEQUENCE: 122

Trp Glu Thr Leu Arg Arg Gly Gly Arg Trp Ile Leu Ala Ile Pro Arg
1               5                   10                  15

Arg Ile Arg Gln Gly Leu Glu Leu Thr Leu Leu
            20                  25
```

MODIFIED IMMUNODEFICIENCY VIRUS PARTICLES

RELATED APPLICATIONS

This application is a continuation-in-part of U.S. non-provisional patent application Ser. No. 10/311,679 filed Dec. 18, 2002, now abandoned, which is a U.S. national phase from PCT patent application No. PCT/IB01/01099 filed Jun. 21, 2001, which claims the benefit of Australian patent application PQ8469 filed Jun. 29, 2000 and PCT patent application No. PCT/AU00/01603 filed Dec. 28, 2000. The present application also claims the benefit of U.S. provisional patent application Ser. No. 60/390,066 filed Jun. 20, 2002.

FIELD OF THE INVENTION

The present invention relates to a delipidation method employing a solvent system useful for extracting lipids from a virus, thereby creating a modified viral particle. The solvent system of the present invention is optimally designed such that upon delipidation of the virus, the viral particle remains substantially intact. By dissolving the lipid envelope surrounding the viral particle using the method of the present invention, the resultant modified viral particle has exposed antigens (or epitopes), which foster and promote antibody production. The resulting modified viral particle of the present invention initiates a positive immunogenic response in the species into which it is re-introduced. The present invention can be applied to delipidating viruses from a specific patient for future reintroduction into the patient, to delipidating stock viruses, or non-patient specific viruses, for use as a vaccine, or to delipidating and combining both non-patient specific viruses and patient specific viruses to create a therapeutic cocktail.

BACKGROUND OF THE INVENTION

Introduction

Viruses, of varied etiology, affect billions of animals and humans each year and inflict an enormous economic burden on society. Many viruses contain lipid as a major component of the membrane that surrounds them. Viruses affect animals and humans causing extreme suffering, morbidity, and mortality. These viruses travel throughout the body in biological fluids such as blood, peritoneal fluid, lymphatic fluid, pleural fluid, pericardial fluid, cerebrospinal fluid, and in various fluids of the reproductive system. Fluid contact at any site promotes transmission of disease. Other viruses reside primarily in different organ systems and in specific tissues, proliferate and then enter the circulatory system to gain access to other tissues and organs at remote sites. If the body does not exhibit a positive immune response against these pathogens, they infect many cell types within the body, inhibiting these cells from performing their normal functions.

The human immune system is composed of various cell types that collectively protect the body from different viruses. The immune system provides multiple means for targeting and eliminating foreign elements, including humoral and cellular immune responses, participating primarily in antigen recognition and elimination. An immune response to foreign elements requires the presence of B-lymphocytes (B cells) or T-lymphocytes (T cells) in combination with antigen-presenting cells (APC), which are usually macrophage or dendrite cells. The APCs are specialized immune cells that capture antigens. Once inside an APC, antigens are broken down into smaller fragments called epitopes—the unique markers carried by the antigen surface. These epitopes are subsequently displayed on the surface of the APCs and are responsible for triggering an antibody response in defense of the infection.

In a humoral immune response, when an APC displaying antigens (in the form of unique epitope markers) foreign to the body are recognized, B cells are activated, proliferating and producing antibodies. These antibodies specifically bind to the antigens present on the APC and block their ability to further infect cells. After the antibody attaches, the APC engulfs the entire antigen and kills it. This type of antibody immune response is primarily involved in the prevention of viral infection.

In a cellular immune response, on recognizing the APC displaying a foreign antigen, the T cells are activated. There are two steps in the cellular immune response. The first step involves activation of cytotoxic T cells (CTL) or CD8+ T killer cells that proliferate and kill target cells that specifically present antigens presented by APC. The second involves helper T cells (HTL) or CD4+ T cells that regulate the production of antibodies and the activity of CD8+ cells. The CD4+ T cells provide growth factors to CD8+ T cells that allow them to proliferate and function efficiently.

Certain infective pathogens are deemed "chronic" due to their structure. For example, some viruses are able to evade an immune response because of their ability to hide some of their antigens from the immune system. Viruses contain an outer envelope made up of lipids and fats derived from the host cell membrane during the budding process. Viruses are comprised of virions, non-cellular infectious agents consisting of a single type of nucleic acid (either RNA or DNA), surrounded by a protein coat. The outer protein covering of viruses is called a capsid, made up of repeating subunits called capsomeres.

Since viruses are non-metabolic, they only reproduce within living host cells. The virus codes the proteins of the viral envelope while the host cell codes the lipids and carbohydrates. Therefore, the lipid and carbohydrate content within a given viral envelope is dependent on the particular host. The enveloped viral particles therefore partially adopt the identity of the host cell, via lipid and carbohydrate content, and are able to conceal antigens associated with them, which would normally have initiated an immune response. Instead, the viral particle confuses the host immune system by presenting it with an antigenic complex that contains components of host tissues, and is perceived by the host immune system as partly "self" and partly "foreign". An immune response that destroys the antigenic complex containing host tissue elements can end up destroying host cells leading to severe autoimmune disease. The immune system is forced to produce the "compromise", ineffective antibodies which do not destroy the viral particles, allowing them to proliferate and slowly cause severe damage to the body, while destroying host cells.

Recent epidemics affecting the immune system include acquired immune deficiency syndrome (AIDS), believed to be caused by the human immunodeficiency virus (HIV). Related viruses affect animal species, for example, simians and felines (SIV and FIV, respectively). Other major viral infections include, but are not limited to, meningitis, cytomegalovirus, and hepatitis in its various forms.

Current Methods of Treatment

One prior art method of treating viruses of varied etiology is via drug therapy. Most anti-viral drug therapies are directed to preventing or inhibiting viral replication and appear to focus on the initial attachment of the virus to the T4 lymphocyte or macrophage, the transcription of viral RNA to viral DNA and the assembly of new virus during reproduction. The high mutation rate of the virus, especially in the case of HIV, is a major difficulty with existing treatments because the various strains become resistant to anti-viral drug therapy. Furthermore, anti-viral drug therapy treatment may cause the evolution of resistant strains of the virus. Other drawbacks to drug therapies are the undesirable side effects and patient compliance requirements. In addition, many individuals are afflicted with multiple viral infections such as a combination of HIV and hepatitis. Such individuals require even more aggressive and expensive drug regimens to counteract disease progression, which in turn cause greater side effects and a greater likelihood of multiple drug resistance.

Also known in the prior art is prevention of disease via the use of vaccinations. Vaccines have been singularly responsible for conferring immune response against several human pathogens. They are designed to stimulate the immune system to protect against various viral infections. In general, a vaccine is produced from an antigen, isolated or produced from the disease-causing microorganism, which can elicit an immune response. When a vaccine is injected into the blood stream as a preventive measure to create an effective immune response, the B cells in the blood stream perceive the antigens contained by the vaccine as foreign or 'non-self' and respond by producing antibodies, which bind to the antigens and inactivate them. Memory cells are thereby produced and remain ready to mount a quick protective immune response against subsequent infection with the same disease-causing agent. Thus when an infective pathogen containing similar antigens as the vaccine enters the body, the immune system will recognize the protein and instigate an effective defense against infection.

The current methods of vaccination do have drawbacks, making them less than optimally desirable for immunizing individuals against particular pathogens, especially HIV. The existing vaccine strategies aim to expose the body to the antigens associated with infective pathogens so that the body builds an immune response against these pathogens. For example, hepatitis B and HIV pathogens are able to survive and proliferate in the human body despite having an effective immune response. One explanation offered in the prior art is that the antigens of these microorganisms change constantly so the antibodies produced in response to a particular antigen are no longer effective when the antigen mutates. The AIDS virus is believed to undergo this antigenic variation. Although antigenic variation has been addressed via the attempted use of combination drugs or antigens, no prior art vaccine has succeeded in addressing chronic infections such as HIV.

Another approach to treating viruses of varied etiology is to inactivate the virus. Prior art methods of inactivating viruses using chemical agents have relied on organic solvents such as chloroform or glutaraldehyde. Although viral inactivation is effective in reducing viral load of a patient and treating contaminated blood to be used in blood transfusions, it does have problems. For example, inactivation of a virus does not provide a protective immune response against viral infection. In addition, it is largely geared towards denaturing viral proteins, thereby destroying the structure of the viral particle.

Drug therapy, as described above only provides a temporary solution to viral infectivity and works only to decrease the viral load of a patient. Chemical inactivation of the virus works to temporarily decrease viral infectivity; however, once cells replicate the level of infectivity will increase again. Moreover, these destruction-type processes lead to total cell death and do not initiate or promote a positive immunogenic response in the patient. In sum, prior art methods have largely focused on destroying, yet not suitably modifying, viral particles.

Current Methods of Manufacture of Viral Treatments and Medicaments Viral Inactivation (or Chemical Kill)

Described in the prior art are methods of treating viral particles with organic solvents and high temperatures thus dissolving the lipid envelopes and subsequently inactivating the virus. In those methods, blood is withdrawn from the patient and separated into two phases—the first phase including red cells and platelets and the second phase containing plasma, white cells, and cell-free virus (virion). The second phase is treated with an organic solvent, thereby killing the infected cells and virions, and subsequently reintroduced into the patient. In addition to dissolving the lipid envelope of the virus, the high organic solvent concentrations cause cell death and damage to the antigens. Essentially, this method results in a "chemical kill" of the cell.

Glutaraldehyde is one such solvent whereby cell inactivation is achieved as known by those of ordinary skill in the art by fixation with a dilute solution of glutaraldehyde at about 1:250. Although treating the virus with glutaraldehyde effectively delipidates the virus, it also destroys the core. Destruction of the core is not desirable for producing a modified viral particle useful for inducing an immune response in a recipient.

Chloroform is another such solvent. Chloroform, however, denatures many plasma proteins and is not suitable for use with biological fluids, which will be reintroduced into the animal or human. These plasma proteins deleteriously affected by chloroform serve important biological functions including coagulation, hormonal response, and immune response. These functions are essential to life and thus damage to these proteins may have an adverse effect on a patient's health, possibly leading to death.

Other solvents or detergents such as B-propiolactone, TWEEN-80, and dialkyl or trialkyl phosphates have been used, either alone or in combination. Many of these methods, especially those involving detergents, require tedious procedures to ensure removal of the detergent before reintroduction of the treated plasma sample into the animal or human. Further, many of the methods described in the prior art involve extensive exposure to elevated temperature in order to kill free virus and infected cells. Elevated temperatures have deleterious effects on the proteins contained in biological fluids, such as plasma.

Current Methods of Manufacturing Vaccines

To date, several manufacturing methods have been employed in search for safe and effective vaccines for immunizing individuals against infective pathogenic agents. To protect an individual from a specific pathogenic infection, a target protein or antigen associated with the infective pathogen is administered to the individual. This includes presenting the protein as part of a non-infective (inactivated) or less infective (attenuated) agent or as a discreet protein composition. Known to one of ordinary skill in the art are the following different types of vaccines: live attenuated vaccines, whole inactivated vaccines, DNA vaccines, combination vaccines, recombinant vaccines, live recombinant vector vaccines, virus like particles and synthetic peptide vaccines.

In live attenuated vaccines, the viruses are rendered less pathogenic to the host, either by specific genetic manipulation of the virus genome or by passage in some type of tissue culture system. In order to achieve genetic manipulation, an inessential gene is deleted or one or more essential genes in the virus are partially damaged. Upon genetic manipulation, the viral particles become less virulent yet retain antigenic features. Live attenuated vaccines can also be used as "vaccine vectors" for other genes, wherein they act as carriers of genes from a second virus (or other pathogen) against which protection is required. Attenuated vaccines (less infective and not inactivated), however, pose several problems. First, it is difficult to ascertain when the attenuated vaccine is no longer pathogenic. The risk of viral infection from the vaccine is too great to properly test for effective attenuation. In addition, attenuated vaccines carry the risk of reverting into a virulent form of the pathogen.

Whole inactivated vaccines are known in the art for immunizing against infection by introducing killed or inactivated viruses to introduce pathogen proteins to an individual's immune system. The administration of killed or inactivated pathogen, via heat or chemical means, into an individual introduces the pathogen to the individual's immune system in a non-infective form thereby instigating an immune response defense. Wholly inactivated vaccines provide protection by directly generating cellular and humoral immune responses against the pathogenic immunogens. There is little threat of infection, because the viral pathogen is killed or otherwise inactivated.

Subunit vaccines are yet another form of vaccination well known to one of ordinary skill in the art. These consist of one or more isolated proteins derived from the pathogen. These proteins act as target antigens against which an immune response is exhibited. The proteins selected for the subunit vaccine are displayed by the pathogen so that upon infection of an individual by the pathogen, the individual's immune system recognizes the pathogen and instigates an immune response. Subunit vaccines are not whole infective agents and are therefore incapable of becoming infective. Subunit vaccines are the basic of AIDSVAX, the first vaccine for HIV being tested for effectiveness in humans and which contains a portion of HIV's outer surface (envelope) protein, called gp120.

DNA vaccine is another type known in the art and uses actual genetic material of pathogens. In addition, synthetic peptide vaccines are made up of parts of synthetic, chemically engineered HIV proteins called peptides. They comprise portions of HIV proteins chosen specifically to achieve an anti-HIV immune response. Also mentioned in the prior art are combination vaccines that, when used in conjunction with one another, generate a broad spectrum of immune responses. One example of a combination vaccine is SHIV, which is a synthetic vaccine made from the HIV envelope and SIV core.

What is needed is a therapeutic method and system for providing patients with patient-specific antigens capable of initiating a protective immune response. Accordingly, what is needed is a simple, effective method that does not appreciably denature or extract plasma proteins from the biological sample being treated. What is also needed is an effective delipidation process via which a viral particle is modified, rather than destroyed, thereby both reducing and/or eliminating infectivity of the viral particle and invoking a patient specific, autologous immune response to reduce viral infection and prevent further infection.

What is also needed is an effective means to immunize individuals against viral pathogen infection that is unique to the individual due to viral mutations. Preferably the means would elicit a broad, biologically active protective immune response with minimized risk of infecting the individual.

SUMMARY OF THE INVENTION

The present invention solves the problems described above by providing a simple, effective and efficient method for treating and preventing viral infection. The method of the present invention affects the lipid envelope of a virus by utilizing an efficient solvent system, which does not denature or destroy the virus. The present invention employs an optimal solvent and energy system to create, via delipidation, a non-synthetic, host-derived modified viral particle that has its lipid envelope at least partially removed, generating a positive immunologic response in a patient, thereby providing that patient with some degree of protection against the virus.

The present invention is also effective in producing an autologous, patient-specific therapeutic vaccine against the virus, by treating a biological fluid containing the virus such that the virus is present in a modified form, but no longer infectious and such that an immune response is initiated upon reintroduction of the fluid into the patient. To create the vaccine, a biological fluid (for example, blood) is removed from the patient, the plasma is separated from the blood and treated to isolate the virus, and the virus is delipidated using an optimal solvent system. A lipid-containing virus, treated in this manner in order to reduce its infectivity and create a modified viral particle, is administered to a recipient, such as an animal or a human, together with a pharmaceutically acceptable carrier in order to initiate an immune response in the animal or human and create antibodies that bind the exposed epitopes of the modified viral particle. Adjuvants may also be administered with the modified viral particle in the pharmaceutically acceptable carrier.

Thus an effective method is presented, by which new vaccines can be developed out of lipid containing viruses by removing lipid from the lipid envelope and exposing antigens hidden within the lipid envelope or beneath the surface of the lipid envelope, in turn generating a positive immune response when re-introduced into the patient.

The present invention provides a modified viral particle comprising at least a partially delipidated viral particle, wherein the partially delipidated viral particle initiates a positive immune response in an animal or human patient and incites protection against an infectious organism in the animal or the human patient.

The present invention provides a method for creating a modified viral particle comprising the steps of: receiving a plurality of viral particles, each having a viral envelope, in a fluid; exposing the viral particles to a delipidation process; and, partially delipidating the viral particles wherein the delipidation process at least partially removes the viral envelopes to create the modified viral particle and wherein the modified viral particle is capable of provoking a positive immune response in a patient.

The present invention also provides an antigen delivery vehicle and a method for creating an antigen delivery vehicle comprising the steps of: receiving a plurality of viral particles, each having a viral envelope, in a fluid; exposing the viral particles to a delipidation process; and, partially delipidating the viral particles to create modified viral particles that act as antigen delivery vehicles, wherein the delipidation process at least partially removes the viral envelopes to expose at least one antigen and wherein the at least one antigen is capable of provoking a positive immune response in a patient.

The modified viral particles of the present invention comprise at least a partially delipidated viral particle, wherein the partially delipidated viral particle is produced by exposing a non-delipidated viral particle to a delipidation process and wherein the partially delipidated viral particle comprises at least one exposed patient specific antigen that was not exposed in the non-delipidated viral particle.

The present invention also provides a vaccine composition, comprising at least a partially delipidated viral particle having patient-specific antigens and a pharmaceutically acceptable carrier, wherein the partially delipidated viral particle is capable of provoking a positive immune response when the composition is administered to a patient.

The present invention also provides a method for making a vaccine comprising: contacting a lipid-containing viral particle in a fluid with a first organic solvent capable of extracting lipid from the lipid-containing viral particle; mixing the fluid and the first organic solvent for a time sufficient to extract lipid from the lipid-containing viral particle; permitting organic and aqueous phases to separate; and collecting the aqueous phase containing a modified viral particle with reduced lipid content wherein the modified viral particle is capable of provoking a positive immune response when administered to a patient.

The present invention also provides a method to protect an animal or a human against an infectious viral particle comprising administering to the animal or the human an effective amount of a composition comprising a modified viral particle, wherein the modification comprises at least partial removal of a lipid envelope of the infectious viral particle, and a pharmaceutically acceptable carrier, wherein the amount is effective to provide a protective effect against infection by the infectious viral particle in the animal or the human.

The present invention also provides a method for provoking a positive immune response in an animal or human having a plurality of lipid-containing viral particles, comprising the steps of: obtaining a fluid containing the lipid-containing viral particles from the animal or the human; contacting the fluid containing the lipid-containing viral particles with a first organic solvent capable of extracting lipid from the lipid-containing viral particles; mixing the fluid and the first organic solvent: permitting organic and aqueous phases to separate; collecting the aqueous phase containing modified viral particles with reduced lipid content; and introducing the aqueous phase containing the modified viral particles with reduced lipid content into the animal or the human wherein the modified viral particles with reduced lipid content provoke a positive immune response in the animal or the human.

The present invention also provides a method for treating a viral infection in an animal or human patient comprising: removing blood containing a plurality of lipid-containing infectious viral particles from the animal or the human; obtaining plasma from the blood, the plasma containing the lipid-containing infectious viral particles; contacting the plasma containing the lipid-containing infectious viral particles with a first organic solvent capable of extracting lipid from the lipid-containing infectious viral particles to produce modified viral particles having reduced lipid content; mixing the plasma and the first organic solvent; permitting organic and aqueous phases to separate; collecting the aqueous phase containing the modified viral particles; and introducing the aqueous phase containing the modified viral particles into the animal or the human wherein the modified viral particles have at least one exposed patient-specific antigen that was not exposed in the plurality of lipid-containing infectious viral particles.

As shown below, the characteristics of the modified viral particle are exhibited in experimental data, showing mice having a positive immunogenic response when vaccinated as compared with a wholly inactivated vaccine. In addition, data exhibiting protein recovery indicate retention of the structural integrity of the viral particle, removing only its lipid-containing envelope.

Fluids which may be treated with the method of the present invention include but are not limited to the following: plasma; serum; lymphatic fluid; cerebrospinal fluid; peritoneal fluid; pleural fluid; pericardial fluid; various fluids of the reproductive system including but not limited to semen, ejaculatory fluids, follicular fluid and amniotic fluid; cell culture reagents such as normal sera, fetal calf serum or serum derived from any other animal or human; and immunological reagents such as various preparations of antibodies and cytokines.

The method of the present invention may be used to treat viruses containing lipid in the viral envelope. Preferred viruses to be treated with the method of the present invention include the various immunodeficiency viruses including but not limited to human (HIV) and subtypes such as HIV-1 and HIV-2, simian (SIV), feline (FIV), as well as any other form of immunodeficiency virus. Other preferred viruses to be treated with the method of the present invention include but are not limited to hepatitis in its various forms. Another preferred virus treated with the method of the present invention is the bovine pestivirus. It is to be understood that the present invention is not limited to the viruses provided in the list above. Additional specific viruses are described in the detailed description of this application. All viruses containing lipid, especially in their viral envelope, are included within the scope of the present invention.

The present invention also provides a simple, inexpensive and easy to use kit for delipidating fluids and lipid-containing viruses within fluids and to create modified viral particles. This kit may be used in various situations, such as in the field, in a clinic, by a physician in an emergency situation, in a laboratory or elsewhere. Preferred fluids include biological fluids and culture medium. A preferred biological fluid is plasma.

The kits of the present invention may be used to process plasma from a patient. In a preferred embodiment, the plasma contains lipid-containing virus. This delipidated plasma containing modified viral particles may be stored in a blood bank for subsequent autologous or heterologous administration. The kits of the present invention may be used to process plasma from a patient and then administer the delipidated plasma, containing modified viral particles, to the patient. The kits of the present invention may be used to process other fluids containing lipids or lipid-containing viruses, such as culture media and cells cultured in media. The modified viral particles produced with these kits may be combined with a pharmaceutically acceptable carrier, and optionally an adjuvant, and used as vaccines by administration to an animal or human to cause an immune response to epitopes on or in the modified viral particles.

The kits of the present invention generally comprise containers used for different purposes. A first container generally contains one or more first extraction solvents. This first container contains means for removing the first extraction solvent from the container. Such means may be a component of the first container or a separate component adapted to function with the first container. Such means include, but are not limited to, any type of cap, spout, funnel, penetrable seal, penetrable diaphragm, tube, pipette, or other means known to one skilled in the art for removing the one or more first extraction solvents or for introducing a fluid containing lipid or lipid-containing virus into the first container. A second container contains the fluid containing lipids or lipid-containing virus to be delipidated.

In one embodiment, a third container is used for contacting or mixing the fluid containing lipids or lipid-containing virus to be delipidated and the first extraction solvent. Mixing can occur through agitation, inversion, shaking, or other means to agitate the third container to a degree sufficient to mix the fluid and the first extraction solvent. After the mixing step, the first extraction solvent containing the dissolved lipids from the fluid or from the lipid-containing organisms separates from the fluid. At this point, the delipidated fluid may be removed through any means such as pouring, decanting, pipetting, applying a vacuum connected to a tube or pipette, or any other means known to one of ordinary skill in the art of removing separated fluids.

A fourth container optionally receives the delipidated fluid and modified viral particles from the third container. Alternatively, the delipidated fluid and modified viral particles are administered to the patient through a tube, catheter, an intravenous line, an intraarterial line or other means without introduction into a fourth container.

In one embodiment the first container contains sufficient volume within it to receive the fluid containing lipids or lipid-containing virus to be delipidated. In this embodiment, mixing of the first extraction solvent and the fluid containing lipids or lipid-containing virus to be delipidated occurs within the first container. In this embodiment, a separate container for mixing the fluid and the first extraction solvent, referred to as the third container above, is not required. After mixing occurs, the first extraction solvent containing the dissolved lipids separates from the delipidated fluid. At this point, the delipidated fluid may be introduced into another container, analogous to the fourth container described above for subsequent introduction into a patient or for optional additional extraction of the first extraction solvent with a second extraction solvent.

In another embodiment, when a second extraction solvent is optionally employed to assist in removal of the first extraction solvent, a fifth container is included which contains the second extraction solvent. This second extraction solvent may be added to the mixture described above in the third container, mixed and then permitted to separate from the delipidated fluid. Alternatively, the second extraction solvent may be added to the fourth container described above, mixed and then permitted to separate from the delipidated fluid if additional removal of residual first extraction solvent is desired. In yet another alternative embodiment, the second extraction solvent may be added to the first container described above containing the mixture of the fluid and the first extraction solvent, mixed and then permitted to separate from the delipidated fluid, if mixing of the fluid and the first extraction solvent, separation and additional extraction of the first extraction solvent using a second extraction solvent are all performed in the first container. The containers described above may be graduated for easy determination of volume within a container.

Accordingly, it is an object of the present invention to provide a method for treating lipid containing virus in order to create modified viral particles.

It is another object of the present invention to provide a method for treating or preventing viral disease by administering modified viral particles to a patient.

Another object of the present invention is to provide a method for treating a biological fluid in order to reduce or eliminate the infectivity of infectious viral organisms contained therein.

It is further an object of the present invention to provide a method for treatment of lipid-containing viruses within a fluid, which minimizes deleterious effects on proteins contained within the fluid, thereby creating a modified viral particle with properties that are capable of initiating a positive immune response in a patient.

It is a further object of the present invention to provide a method for treatment of lipid-containing viruses within a fluid, which minimizes deleterious effects on proteins contained within the fluid, thereby creating a modified viral particle with patient-specific antigens.

It is another object of the present invention to provide a method for reducing the infectivity of viruses, wherein the method does not employ elevated temperatures, chloroform, detergents, or trialkyl phosphates.

It is another object of the present invention to provide a method for reducing the infectivity of viruses, wherein the method exposes antigenic determinants on the modified viral particle.

It is a further object of the present invention to completely or partially delipidate the viral particle, wherein the viral particles comprise immunodeficiency virus, hepatitis in its various forms, or any other lipid-containing virus, thereby creating a modified viral particle.

It is a further object of the present invention to completely or partially delipidate the viral particle, wherein the viral particles comprise immunodeficiency virus, hepatitis in its various forms, or any other lipid-containing virus, while retaining the structural protein core of the virus.

It is another object of the present invention to provide a method for reducing the infectivity of viruses, wherein the newly formed viral particle can be used as an antigen delivery vehicle.

Yet another object of the present invention is to treat infectious organisms with the method of the present invention in order to reduce their infectivity and provide a vaccine comprising a delipidated, modified viral particle which may be administered to an animal or a human together with a pharmaceutically acceptable carrier and optionally an immunostimulant compound, to prevent or minimize clinical manifestation of disease in a patient following exposure to the virus.

Yet another object of the present invention is to treat infectious organisms with the method of the present invention in order to reduce their infectivity and provide a vaccine comprising a delipidated, modified viral particle which may be administered to an animal or a human together with a pharmaceutically acceptable carrier and optionally an immunostimulant compound, to initiate a positive immunogenic response in the animal or human.

It is another specific object of the present invention to provide an antiviral vaccine.

It is a further specific object of the present invention to lessen the severity of a disease caused by a lipid-containing virus in an animal or human receiving a vaccine comprising a composition comprising a virus treated with the method of the present invention in a pharmaceutically acceptable carrier.

It is another object of the present invention to combine delipidated viral particles having patient specific antigens with delipidated stock viral particles to create a therapeutic cocktail for the treatment of diseases.

Accordingly it is an object of the present invention to provide an inexpensive and easy to use kit for removal of lipids from fluids and infectious organisms, preferably biological fluids, plasma, or culture medium.

Another object of the present invention is to provide an inexpensive and easy to use kit for removal of lipids from lipid-containing viruses to create modified viral particles.

These and other features and advantages of the present invention will become apparent after review of the following drawings and detailed description of the disclosed embodiments. Various modifications to the stated embodiments will be readily apparent to those of ordinary skill in the art, and the disclosure set forth herein may be applicable to other embodiments and applications without departing from the spirit and scope of the present invention.

BRIEF DESCRIPTION OF THE DRAWINGS

The accompanying drawings, which are incorporated in and form a part of the specification, illustrate preferred embodiments of the present invention.

DETAILED DESCRIPTION OF THE INVENTION

Definitions

Figure 1:
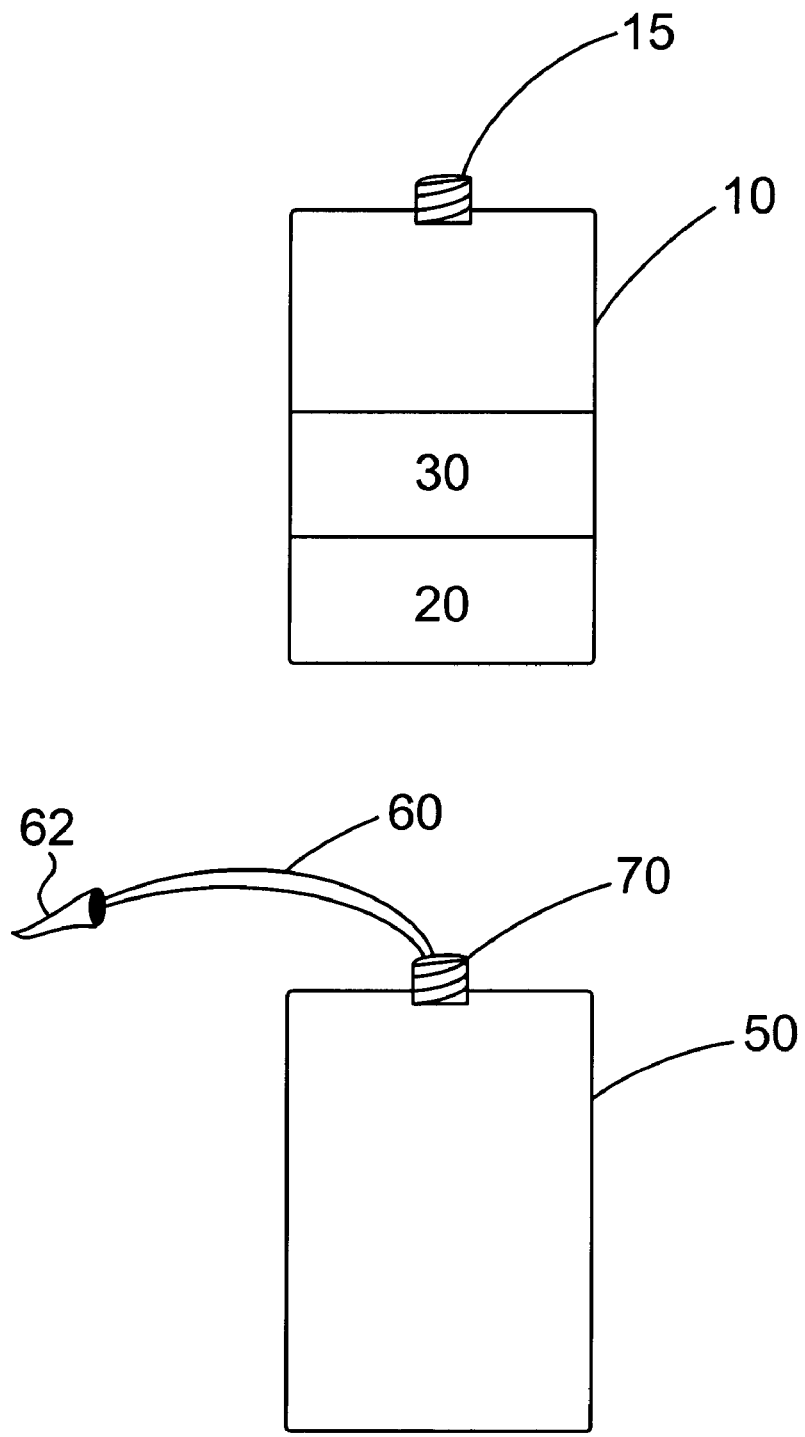
FIG. 1 is a schematic diagram of an embodiment of a kit of the present invention containing a first container 10 with a screw cap 15, containing first extraction solvent 20, and plasma 30, and a second container 50 with a tube 60 leading from an opening 70, the tube 60 being connected to a needle 62.

By the term "fluid" is meant any fluid containing an infectious organism, including but not limited to, a biological fluid obtained from an organism such as an animal or human. Preferred infectious organisms treated with the method of the present invention are viruses. Such biological fluids obtained from an organism include but are not limited to plasma, serum, cerebrospinal fluid, lymphatic fluid, peritoneal fluid, follicular fluid, amniotic fluid, pleural fluid, pericardial fluid, reproductive fluids and any other fluid contained within the organism. Other fluids may include laboratory samples containing infectious organisms suspended in any chosen fluid. Other fluids include cell culture reagents, many of which include biological compounds such as fluids obtained from living organisms, including but not limited to "normal serum" obtained from various animals and used as growth medium in cell and tissue culture applications.

By the terms "first solvent" or "first organic solvent" "or first extraction solvent" are meant a solvent, comprising one or more solvents, used to facilitate extraction of lipid from a fluid or from a lipid-containing biological organism. This solvent will enter the fluid and remain in the fluid until being removed. Suitable first extraction solvents include solvents that extract or dissolve lipid, including but not limited to alcohols, hydrocarbons, amines, ethers, and combinations thereof. First extraction solvents may be combinations of alcohols and ethers. First extraction solvents include, but are not limited to n-butanol, diisopropyl ether (DIPE), diethyl ether, and combinations thereof The term "second extraction solvent" is defined as one or more solvents that facilitate the removal of a portion of the first extraction solvent. Suitable second extraction solvents include any solvent that facilitates removal of the first extraction solvent from the fluid. Second extraction solvents include any solvent that facilitates removal of the first extraction solvent including but not limited to ethers, alcohols, hydrocarbons, amines, and combinations thereof. Preferred second extraction solvents include diethyl ether and di-isopropyl ether, which facilitate the removal of alcohols, such as n-butanol, from the fluid. The term "de-emulsifying agent" is a second extraction solvent that assists in the removal of the first solvent which may be present in an emulsion in an aqueous layer.

The term "delipidation" refers to the process of removing at least a portion of a total concentration of lipids in a fluid or in a lipid-containing organism. Lipid-containing organisms may be found within fluids which may or may not contain additional lipids.

The terms "pharmaceutically acceptable carrier" or "pharmaceutically acceptable vehicle" are used herein to mean any liquid including but not limited to water or saline, a gel, salve, solvent, diluent, fluid ointment base, liposome, micelle, giant micelle, and the like, which is suitable for use in contact with living animal or human tissue without causing adverse physiological responses, and which does not interact with the other components of the composition in a deleterious manner.

The term "patient" refers to animals and humans in this application.

A Modified Viral Particle

Practice of the method of the present invention to reduce the lipid content of a virus creates a modified viral particle. These modified viral particles are immunogenic. The present methods expose epitopes that are not usually presented to the immune system by untreated virus. A structural change occurs in the modified viral particles, and proteins on, in, or near the surface of the virus are modified such that a conformational change occurs. Some of these proteins may also separate from the modified viral particle. FIG. 4 is a schematic representation of HIV viral particle showing the lipid containing envelope or bilayer derived from a host cell, surface glycoproteins, transmembrane proteins, the capsid, capsid proteins and nuclear material. The delipidation process of the present invention modifies the viral particle. The modified viral particle has a lower lipid content in the envelope, displays modified proteins, loses infectivity and is immunogenic.

Modified Viral Particle Resulting from Removal of Lipid from Lipid-Containing Organisms As described above, methods of treating the viral particles with organic solvents and use of high temperatures, thus dissolving the lipid envelopes and subsequently inactivating the virus are well known in the prior art. In this method, blood is withdrawn from the patient and separated into two phases—the first phase including red cells and platelets and the second phase containing plasma, white cells, and cell-free virus (virion). The second phase is treated with an organic solvent, thereby killing the infected cells and virions, and subsequently reintroduced into the patient. In addition to dissolving the lipid envelope of the virus, however, the high organic solvent concentrations cause cell death and damage to the antigens. This method results in a "chemical kill" of the cell. Another drawback is that elevated temperatures have deleterious effects on the proteins contained in biological fluids such as plasma. Glutaraldehyde is one such solvent whereby cell inactivation is achieved as known by those of ordinary skill in the art by fixation with a dilute solution of glutaraldehyde at about 1:250.

When a viral particle is sent through certain solvent systems, lipids will be removed in the solvent because, when treated appropriately, lipids are soluble in certain solvent systems. Viruses are comprised of virions with the outer covering comprised of a protein coat, or capsid, as described above. Since viruses are non-metabolic, they only reproduce within living host cells. The virus codes the proteins of the viral envelope while the host cell codes the lipids and carbohydrates. Therefore, the lipid and carbohydrate within a given viral envelope is dependent on the particular host. The enveloped viral particles therefore partially adopt the identity of the host cell and are able to conceal some antigens associated with the virus, which normally would have initiated an immune response.

Instead, the viral particle confuses the host immune system by presenting it with an antigenic complex that contains components of host tissues, and is perceived by the host immune system as partly "self" and partly "foreign". An immune response that destroys the antigenic complex containing host tissue elements can destroy host cells leading to severe autoimmune disease. The immune system is forced to produce the "compromise", ineffective antibodies which do not destroy the viral particles, allowing them to proliferate and slowly cause severe damage to the body, while the host cells are destroyed.

Methods of the present invention can be used to solve this problem because, by removing the lipid envelope of the virus, and keeping the viral particle intact, the method of the present invention exposes additional antigens. The host immune system is forced to recognize the viral particle as wholly "foreign". Using the method of the present invention, what is created is a modified viral particle in which the antigenic core remains intact, thereby using the epitopes of the actual viral particle to initiate a positive immunogenic response in the patient into which it is reintroduced. In addition, the method of the present invention reduces the deleterious effect on the other plasma proteins, measured by protein recovery, such that the plasma can be reintroduced into the patient.

In creating this modified viral particle what is also created is a patient-specific antigen that induces protection against the viral particle in the species in which it is introduced. The method of the present invention creates an effective means to immunize individuals against viral pathogen infection and elicit a broad, biologically active protective immune response without risk of infecting the individual. New vaccines may be developed from certain lipid containing viruses by removing the lipid envelope and exposing antigens hidden beneath the envelope, in turn generating a positive immune response. These "autologous vaccines" can be created by the at least partial removal of the lipid envelope using suitable solvent systems (one which would not damage the antigens contained in the particle) exposing antigens and/or forcing a structural modification in the viral protein structures, which when introduced into the body, would provoke an effective immune response.

Infectious Organisms Treated with the Present Invention

Viruses are the preferred infectious organism treated with the method of the present invention. Viral infectious organisms which may be delipidated by the present invention to form modified viral particles include, but are not limited to the lipid-containing viruses of the following genuses: Alphavirus (alphaviruses), Rubivurus (rubella virus), Flavivirus (Flaviviruses), Pestivirus (mucosal disease viruses), (unnamed, hepatitis C virus), Coronavirus, (Coronaviruses) severe acute respiratory syndrome (SARS), Torovirus, (toroviruses), Arteivirus, (arteriviruses), Paramyxovirus, (Paramyxoviruses), Rubulavirus (rubulavriuses), Morbillivirus (morbillivuruses), Pneumovirinae (the pneumoviruses), Pneumovirus (pneumoviruses), Vesiculovirus (vesiculoviruses), Lyssavirus (lyssaviruses), Ephemerovirus (ephemeroviruses), Cytorhabdovirus (plant rhabdovirus group A), Nucleorhabdovirus (plant rhabdovirus group B), Filovirus (filoviruses), Influenzavirus A, B (influenza A and B viruses), Influenza virus C (influenza C virus), (unnamed, Thogoto-like viruses), Bunyavirus (bunyaviruses), Phlebovirus (phleboviruses), Nairovirus (nairoviruses), Hantavirus (hantaviruses), Tospovirus (tospoviruses), Arenavirus (arenaviruses), unnamed mammalian type B retroviruses, unnamed, mammalian and reptilian type C retroviruses, unnamed, type D retroviruses, Lentivirus (lentiviruses), Spumavirus (spumaviruses), Orthohepadnavirus (hepadnaviruses of mammals), Avihepadnavirus (hepadnaviruses of birds), Simplexvirus (simplexviruses), Varicellovirus (varicelloviruses), Betaherpesvirinae (the cytomegaloviruses), Cytomegalovirus (cytomegaloviruses), Muromegalovirus (murine cytomegaloviruses), Roseolovirus (human herpes virus 6, 7, 8), Gammaherpesvirinae (the lymphocyte-associated herpes viruses), Lymphocryptovirus (Epstein-Bar-like viruses), Rhadinovirus (saimiri-ateles-like herpes viruses), Orthopoxvirus (orthopoxviruses), Parapoxvirus (parapoxviruses), Avipoxvirus (fowlpox viruses), Capripoxvirus (sheeppoxlike viruses), Leporipoxvirus (myxomaviruses), Suipoxvirus (swine-pox viruses), Molluscipoxvirus (molluscum contagiosum viruses), Yatapoxvirus (yabapox and tanapox viruses), Unnamed, African swine fever-like viruses, Iridovirus (small iridescent insect viruses), Ranavirus (front iridoviruses), Lymphocystivirus (lymphocystis viruses of fish), Togaviridae, Flaviviridae, Coronaviridae, Enabdoviridae, Filoviridae, Paramyxoviridae, Orthomyxoviridae, Bunyaviridae, Arenaviridae, Retroviridae, Hepadnaviridae, Herpesviridae, Poxviridae, and any other lipid-containing virus.

These viruses include the following human and animal pathogens: Ross River virus, fever virus, dengue viruses, Murray Valley encephalitis virus, tick-borne encephalitis viruses (including European and far eastern tick-borne encephalitis viruses, California encephalitis virus, St. Louis encephalitis virus, sandfly fever virus, human coronaviruses 229-E and OC43 and others causing the common cold, upper respiratory tract infection, probably pneumonia and possibly gastroenteritis), human parainfluenza viruses 1 and 3, mumps virus, human parainfluenza viruses 2, 4a and 4b, measles virus, human respiratory syncytial virus, rabies virus, Marburg virus, Ebola virus, influenza A viruses and influenza B viruses, Arenaviruss: lymphocytic choriomeningitis (LCM) virus; Lassa virus, human immunodeficiency viruses 1 and 2, or any other immunodeficiency virus, hepatitis B virus, hepatitis C virus, hepatitis G virus, Subfamily: human herpes viruses 1 and 2, herpes virus B, Epstein-Barr virus), (smallpox) virus, cowpox virus, monkeypox virus, molluscum contagiosum virus, yellow fever virus, poliovirus, Norwalk virus, orf virus, and any other lipid-containing virus.

Methods of Manufacture of the Modified Viral Particle

One of ordinary skill in the art would appreciate that there may be multiple delipidation processes employed under the scope of this invention. In a preferred embodiment, a solvent system together applied energy, for example a mechanical mixing system, is used to substantially delipidate the viral particle. The delipidation process is dependent upon the total amount of solvent and energy input into a system. Various solvent levels and mixing methods, as described below, may be used depending upon the overall framework of the process. Although a single solvent or multiple solvents may be used for delipidation of virus, it is to be understood that a single solvent is preferred since there is less probability of destroying and denaturing the viral particle.

Exemplary Solvent Systems for use in Removal of Lipid from Viruses and Effective in Maintaining Integrity of the Viral Particle The solvent or combinations of solvents to be employed in the process of partially or completely delipidating lipid-containing organisms may be any solvent or combination thereof effective in solubilizing lipids in the viral envelope while retaining the structural integrity of the modified viral particle, which can be measured, in one embodiment, via protein recovery. A delipidation process falling within the scope of the present invention uses an optimal combination of energy input and solvent to delipidate the viral particle, while still keeping it intact. Suitable solvents comprise hydrocarbons, ethers, alcohols, phenols, esters, halohydrocarbons, halocarbons, amines, and mixtures thereof. Aromatic, aliphatic, or alicyclic hydrocarbons may also be used. Other suitable solvents, which may be used with the present invention, include amines and mixtures of amines. One solvent system is DIPE, either concentrated or diluted in water or a buffer such as a physiologically acceptable buffer. One solvent combination comprises alcohols and ethers. Another solvent comprises ether or combinations of ethers, either in the form of symmetrical ethers, asymmetrical ethers or halogenated ethers.

The optimal solvent systems are those that accomplish two objectives: first, at least partially delipidating the infectious organism or viral particle and second, employing a set of conditions such that there are few or no deleterious effects on the other plasma proteins. In addition, the solvent system should maintain the integrity of the viral particle such that it can be used to initiate an immune response in the patient. It should therefore be noted that certain solvents, solvent combinations, and solvent concentrations may be too harsh to use in the present invention because they result in a chemical kill.

It is preferred that the solvent or combination of solvents has a relatively low boiling point to facilitate removal through a vacuum and possibly heat without destroying the antigenic core of the viral particle. It is also preferred that the solvent or combination of solvents be employed at a low temperature because heat has deleterious effects on the proteins contained in biological fluids such as plasma. It is also preferred that the solvent or combination of solvents at least partially delipidate the viral particle.

Liquid hydrocarbons dissolve compounds of low polarity such as the lipids found in the viral envelopes of the infectious organisms. Particularly effective in disrupting the lipid membrane of a viral particle are hydrocarbons which are substantially water immiscible and liquid at about 37° C. Suitable hydrocarbons include, but are not limited to the following: $C_5$ to $C_{20}$ aliphatic hydrocarbons such as petroleum ether, hexane, heptane, octane; haloaliphatic hydrocarbons such as chloroform, 1,1,2-trichloro-1,2,2-trifluoroethane, 1,1,1-trichloroethane, trichloroethylene, tetrachloroethylene, dichloromethane and carbon tetrachloride; thioaliphatic hydrocarbons each of which may be linear, branched or cyclic, saturated or unsaturated; aromatic hydrocarbons such as benzene; alkylarenes such as toluene; haloarenes; haloalkylarenes; and thioarenes. Other suitable solvents may also include saturated or unsaturated heterocyclic compounds such as pyridine and aliphatic, thio- or halo-derivatives thereof.

Suitable esters for use in the present invention include, but are not limited to, ethyl acetate, propylacetate, butylacetate and ethylpropionate. Suitable detergents/surfactants that may be used include but are not limited to the following: sulfates, sulfonates, phosphates (including phospholipids), carboxylates, and sulfosuccinates. Some anionic amphiphilic materials useful with the present invention include but are not limited to the following: sodium dodecyl sulfate (SDS), sodium decyl sulfate, bis-(2-ethylhexyl) sodium sulfosuccinate (AOT), cholesterol sulfate and sodium laurate.

Solvents may be removed from delipidated viral mixtures through the use of additional solvents. For example, demulsifying agents such as ethers may be used to remove a first solvent such as an alcohol from an emulsion. Removal of solvents may also be accomplished through other methods, which do not employ additional solvents, including but not limited to the use of charcoal. Charcoal may be used in a slurry or alternatively, in a column to which a mixture is applied. Pervaporation may also be employed to remove one or more solvents from delipidated viral mixtures.

Examples of suitable amines for use in removal of lipid from lipid-containing organisms in the present invention are those which are substantially immiscible in water. Typical amines are aliphatic amines—those having a carbon chain of at least 6 carbon atoms. A non-limiting example of such an amine is $C_6H_{13}NH_2$.

Ether is a preferred solvent for use in the method of the present invention. Particularly preferred are the $C_4$-$C_8$ containing-ethers, including but not limited to ethyl ether, diethyl ether, and propyl ethers (including but not limited to di-isopropyl ether). Asymmetrical ethers may also be employed. Halogenated symmetrical and asymmetrical ethers may also be employed.

Low concentrations of ethers may be employed to remove lipids when used alone and not in combination with other solvents. For example, a low concentration range of ethers include 0.5% to 30%. Such concentrations of ethers that may be employed include, but are not limited to the following: 0.625%, 1.0% 1.25%, 2.5%, 5.0% and 10% or higher. It has been observed that dilute solutions of ethers are effective. Such solutions may be aqueous solutions or solutions in aqueous buffers, such as phosphate buffered saline (PBS). Other physiological buffers may be used, including but not limited to bicarbonate, citrate, Tris, Tris/EDTA, and Trizma. Preferred ethers are di-isopropyl ether (DIPE) and diethyl ether (DEE).

When used in the present invention, appropriate alcohols are those which are not appreciably miscible with plasma or other biological fluids. Such alcohols include, but are not limited to, straight chain and branched chain alcohols, including pentanols, hexanols, heptanols, octanols and those alcohols containing higher numbers of carbons.

When alcohols are used in combination with another solvent, for example, an ether, a hydrocarbon, an amine, or a combination thereof, $C_1$-$C_8$ containing alcohols may be used. Alcohols for use in combination with another solvent include $C_4$-$C_8$ containing alcohols. Accordingly, alcohols that fall within the scope of the present invention are butanols, pentanols, hexanols, heptanols and octanols, and iso forms thereof, in particular, $C_4$ alcohols or butanols (1-butanol and 2-butanol). The specific alcohol choice is dependent on the second solvent employed.

Ethers and alcohols can be used in combination as a first solvent for treating the fluid containing the lipid-containing virus, or viral particle. Any combination of alcohol and ether may be used provided the combination is effective to at least partially remove lipid from the infectious organism, without having deleterious effects on the plasma proteins. In one embodiment, lipid is removed from the viral envelope of the infectious organism. When alcohols and ether are combined as a first solvent for treating the infectious organism contained in a fluid, ratios of alcohol to ether in this solvent are about 0.01%-60% alcohol to about 40%-99.99% of ether, with a specific ratio of about 10%-50% of alcohol with about 50%-90% of ether, with a more specific ratio of about 20%-45% alcohol and about 55%-80% ether.

One combination of alcohol and ether is the combination of butanol and di-isopropyl ether (DIPE). When butanol and DIPE are combined as a first solvent for treating the infectious organism contained in a fluid, ratios of butanol to DIPE in this solvent are about 0.01%-60% butanol to about 40%-99.99% of DIPE, with a specific ratio of about 10%-50% of butanol with about 50%-90% of DIPE, with a more specific ratio of about 20%-45% butanol and about 55%-80% DIPE.

Another combination of alcohol and ether is the combination of butanol with diethyl ether (DEE). When butanol is used in combination with DEE as a first solvent, ratios of butanol to DEE are about 0.01%-60% butanol to about 40%-99.99% of DEE, with a more specific ratio of about 10%-50% of butanol with about 50%-90% of DEE, with a most specific ratio of about 20%-45% butanol and about 55%-80% DEE. One specific ratio of butanol and DEE in a first solvent is about 40% butanol and about 60% DEE. This combination of about 40% butanol and about 60% DEE (vol:vol) has been shown to have no significant effect on a variety of biochemical and hematological blood parameters, as shown for example in U.S. Pat. No. 4,895,558.

Biological Fluids and Treatment thereof for Reducing Infectivity of Infectious, Lipid-Containing Organisms As stated above, various biological fluids may be treated with the method of the present invention in order to reduce the levels of infectivity of the lipid-containing organism in the biological fluid and to create modified viral particles. In a preferred embodiment, plasma obtained from an animal or human is treated with the method of the present invention in order to reduce the concentration and/or infectivity of lipid-containing infectious organisms within the plasma and to create modified viral particles. In this embodiment, plasma may be obtained from an animal or human patient by withdrawing blood from the patient using well-known methods and treating the blood in order to separate the cellular components of the blood (red and white cells) from the plasma. Such methods for treating the blood are known to one of ordinary skill in the art and include but are not limited to centrifugation and filtration. One of ordinary skill in the art understands the proper centrifugation conditions for separating such lipidcontaining organisms from the red and white cells. Filtration may include diafiltration or filtration through membranes with pore sizes that separate the lipid-containing organism, such as the cell-free virus, from the red and white cells. Use of the present invention permits treatment of lipid-containing organisms, for example those found within plasma, without having deleterious effects on other plasma proteins and maintaining the integrity of the viral core.

Viruses are typically retained in the plasma and are affected by the treatment of the plasma with the method of the present invention. In cases where the lipid-containing organism to be treated is substantially larger, and may pellet with red and white blood cells under typical centrifugation conditions for separating cells from plasma, the lipid-containing organism may be separated from the red and white cells using techniques known to one of ordinary skill in the art.

Treatment of lipid-containing organisms in biological fluids other than blood and plasma does not generally involve separation of the cells from the fluid prior to initiation of the delipidation procedure. For example, follicular fluid and peritoneal fluid may be treated with the present invention to affect the levels and infectivity of lipid-containing organisms without deleterious effects on protein components. The treated fluid may subsequently be reintroduced into the animal or human from which it was obtained. Treatment of these non-blood types of fluids affects the lipid-containing organisms in the fluid, such as the virus.

Once a biological fluid, such as plasma, is obtained either in this manner, or for example, from a storage facility housing bags of plasma, the plasma is contacted with a first organic solvent, as described above, capable of solubilizing lipid in the lipid-containing infectious organism. The first organic solvent is combined with the plasma in a ratio wherein the first solvent is present in an amount effective to substantially solubilize the lipid in the infectious organism, for example, dissolve the lipid envelope that surrounds the virus. Exemplary ratios of first solvent to plasma (expressed as a ratio of first organic solvent to plasma) are described in the following ranges: 0.5-4.0:0.5-4.0; 0.8-3.0:0.8-3.0; and 1-2:0.8-1.5. Various other ratios may be applied, depending on the nature of the biological fluid. For example, in the case of cell culture fluid, the following ranges may be employed of first organic solvent to cell culture fluid: 0.5-4.0:0.5-4.0; 0.8-3.0:0.8-3.0; and 1-2:0.8-1.5.

After contacting the fluid containing the infectious organism with the first solvent as described above, the first solvent and fluid are mixed, using methods including but not limited to one of the following suitable mixing methods: gentle stirring; vigorous stirring; vortexing; swirling; homogenization; and end-over-end rotation.

The amount of time required for adequate mixing of the first solvent with the fluid is related to the mixing method employed. Fluids are mixed for a period of time sufficient to permit intimate contact between the organic and aqueous phases, and for the first solvent to at least partially or completely solubilize the lipid contained in the infectious organism. Typically, mixing will occur for a period of about 10 seconds to about 24 hours, possibly about 10 seconds to about 2 hours, possibly approximately 10 seconds to approximately 10 minutes, or possibly about 30 seconds to about 1 hour, depending on the mixing method employed. Non-limiting examples of mixing durations associated with different methods include 1) gentle stirring and end-over-end rotation for a period of about 10 seconds to about 24 hours, 2) vigorous stirring and vortexing for a period of about 10 seconds to about 30 minutes, 3) swirling for a period of about 10 seconds to about 2 hours, or 4) homogenization for a period of about 10 seconds to about 10 minutes.

Separation of Solvents

After mixing of the first solvent with the fluid, the solvent is separated from the fluid being treated. The organic and aqueous phases may be separated by any suitable manner known to one of ordinary skill in the art. Since the first solvent is typically immiscible in the aqueous fluid, the two layers are permitted to separate and the undesired layer is removed. The undesired layer is the solvent layer containing dissolved lipids and its identification, as known to one of ordinary skill in the art, depends on whether the solvent is more or less dense than the aqueous phase. An advantage of separation in this manner is that dissolved lipids in the solvent layer may be removed.

In addition, separation may be achieved through means, including but not limited to the following: removing the undesired layer via pipetting; centrifugation followed by removal of the layer to be separated; creating a path or hole in the bottom of the tube containing the layers and permitting the lower layer to pass through; utilization of a container with valves or ports located at specific lengths along the long axis of the container to facilitate access to and removal of specific layers; and any other means known to one of ordinary skill in the art. Another method of separating the layers, especially when the solvent layer is volatile, is through distillation under reduced pressure or evaporation at room temperature, optionally combined with mild heating. In one embodiment employing centrifugation, relatively low g forces are employed, such as 900×g for about 5 to 15 minutes to separate the phases.

Another method of separating solvent is through the used of charcoal, preferably activated charcoal. This charcoal is optionally contained in a column. Alternatively the charcoal may be used in slurry form. Various biocompatible forms of charcoal may be used in these columns. Pervaporation methods and use of charcoal to remove solvents are preferred methods for removing solvent.

Following separation of the first solvent from the treated fluid, some of the first solvent may remain entrapped in the aqueous layer as an emulsion. Optionally, a de-emulsifying agent is employed to facilitate removal of the trapped first solvent. The de-emulsifying agent may be any agent effective to facilitate removal of the first solvent. A preferred de-emulsifying agent is ether and a more preferred de-emulsifying agent is diethyl ether. The de-emulsifying agent may be added to the fluid or in the alternative the fluid may be dispersed in the de-emulsifying agent. In vaccine preparation, alkanes in a ratio of about 0.5 to 4.0 to about 1 part of emulsion (vol:vol) may be employed as a de-emulsifying agent, followed by washing to remove the residual alkane from the remaining delipidated organism used for preparing the vaccine. Preferred alkanes include, but are not limited to, pentane, hexane and higher order straight and branched chain alkanes.

The de-emulsifying agent, such as ether, may be removed through means known to one of skill in the art, including such means as described in the previous paragraph. One convenient method to remove the de-emulsifying agent, such as ether, from the system, is to permit the ether to evaporate from the system in a running fume hood or other suitable device for collecting and removing the de-emulsifying agent from the environment. In addition, de-emulsifying agents may be removed through application of higher temperatures, for example from about 24 to 37° C. with or without pressures of about 10 to 20 mbar. Another method to remove the de-emulsifying agent involves separation by centrifugation, followed by removal of organic solvent through aspiration, further followed by evaporation under reduced pressure (for example 50 mbar) or further supply of an inert gas, such as nitrogen, over the meniscus to aid in evaporation. Yet another method of removing a first solvent or a demulsifying agent is through the use of adsorbants, such as charcoal. The charcoal is preferably activated charcoal. This charcoal is optionally contained in a column, as described above. Still another method of removing solvent is the use of hollow fiber contactors. Pervaporation methods and charcoal adsorbant methods of removing solvents are preferred.

Methods of Treating Biological Fluids (Delipidation)

It is to be understood that the method of the present invention may be employed in either a continuous or discontinuous manner. That is, in a continuous manner, a fluid may be fed to a system employing a first solvent which is then mixed with the fluid, separated, and optionally further removed through application of a de-emulsifying agent. The continuous method also facilitates subsequent return of the fluid containing delipidated infectious organism to a desired location. Such locations may be containers for receipt and/or storage of such treated fluid, and may also include the vascular system of a human or animal or some other body compartment of a human or animal, such as the pleural, pericardial, peritoneal, and abdominopelvic spaces.

In one embodiment of the continuous method of the present invention, a biological fluid, for example, blood, is removed from an animal or a human through means known to one of ordinary skill in the art, such as a catheter. Appropriate anti-clotting factors as known to one of ordinary skill in the art are employed, such as heparin, ethylenediaminetetraacetic acid (EDTA) or citrate. This blood is then separated into its cellular and plasma components through the use of a centrifuge. The plasma is then contacted with the first solvent and mixed with the first solvent to effectuate lipid removal from the infectious organism contained within the plasma. Following separation of the first solvent from the treated plasma, a de-emulsifying agent is optionally employed to remove entrapped first solvent. After ensuring that acceptable levels (non-toxic) of first solvent or de-emulsifying agent, if employed, are found within the plasma containing the delipidated infectious organism, the plasma is then optionally combined with the cells previously separated from the blood to form a new blood sample containing at least partially delipidated viral particles, also called modified viral particles herein.

Through the practice of this method, the infectivity of the infectious organism is greatly reduced or eliminated. Following recombination with the cells originally separated from the blood, this sample may be reintroduced into either the vascular system or some other system of the human or animal. The effect of such treatment of plasma removed from the human or animal and return of the sample containing the partially or completely delipidated infectious organism, or modified viral particle, to the human or animal causes a net decrease in the concentration and infectivity of the infectious organism contained within the vascular system of the human or animal. In addition to decreasing the concentration and infectivity of the infectious organism contained within the vascular system, the modified viral particle serves to initiate an autologous immune response in the patient. In this manner, infectious viral load is reduced. In this mode of operation, the method of the present invention is employed to treat body fluids in a continuous manner—while the human or animal is connected to an extracorporeal device for such treatment.

In yet another embodiment, the discontinuous or batch mode, the human or animal is not connected to an extracorporeal device for processing bodily fluids with the method of the present invention. In a discontinuous mode of operation, the present invention employs a fluid previously obtained from a human or animal, which may include, but is not limited to plasma, lymphatic fluid, or follicular fluid. The sample may be contained within a blood bank or in the alternative, drawn from a human or animal prior to application of the method. The sample may be a reproductive fluid or any fluid used in the process of artificial insemination or in vitro fertilization. The sample may also be one not directly obtained from a human or animal but rather any fluid containing a potentially infectious organism, such as cell culture fluid. In this mode of operation, this sample is treated with the method of the present invention to produce a new sample which contains at least partially or completely delipidated infectious organisms, or modified viral particles. One embodiment of this mode of the present invention is to treat plasma samples previously obtained from animals or humans and stored in a blood bank for subsequent transfusion. These samples may be treated with the method of the present invention to minimize or eliminate transmission of infectious disease, such as HIV, hepatitis, cytomegalovirus, from the biological sample.

Delipidation of an infectious organism can be achieved by various means. A batch method can be used for fresh or stored biological fluids, for example, fresh frozen plasma. In this case a variety of the described organic solvents or mixtures thereof can be used for viral inactivation. Extraction time depends on the solvent or mixture thereof and the mixing procedure employed.

Kits

Figure 2:
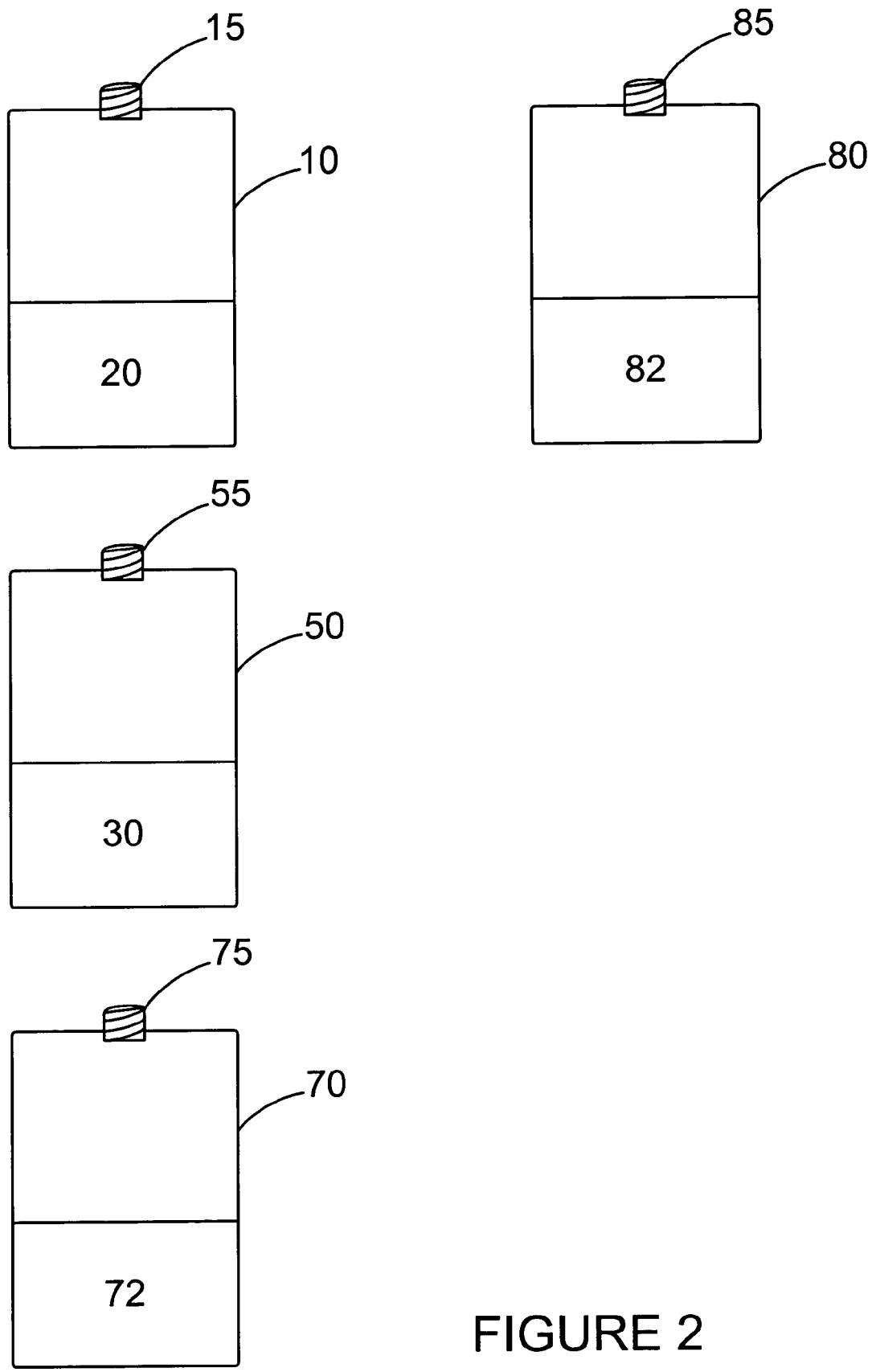
FIG. 2 is a schematic diagram of an embodiment of a kit of the present invention containing a first container 10 with a screw cap 15, containing first extraction solvent 20, a second container 50 with a screw cap 55 and containing plasma 30, a third container 70, with a screw cap 75 for mixing the first extraction solvent 20 and plasma 30 to form mixture 72, and a fourth container 80 with a screw cap 85 for storing delipidated plasma 82.
Figure 3:
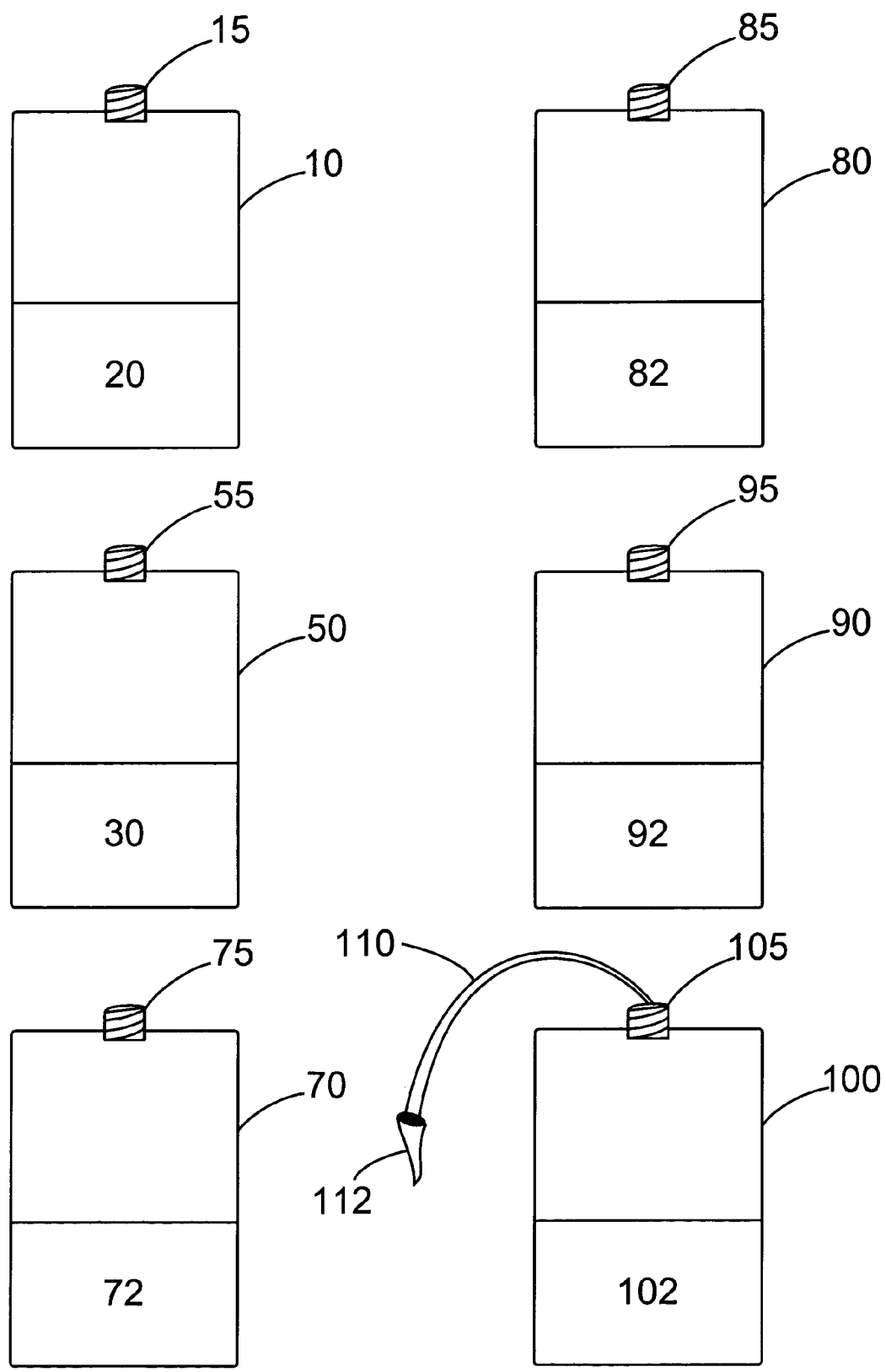
FIG. 3 incorporates the elements of FIG. 2 and further provides a fifth container 90 with a screw cap 95 containing a second extraction solvent 92 and a sixth container 100 for storing delipidated plasma 102 with reduced levels of residual first extraction solvent, with a tube 110 leading from an opening 105, the tube 110 being connected to a needle 112.
Figure 4:
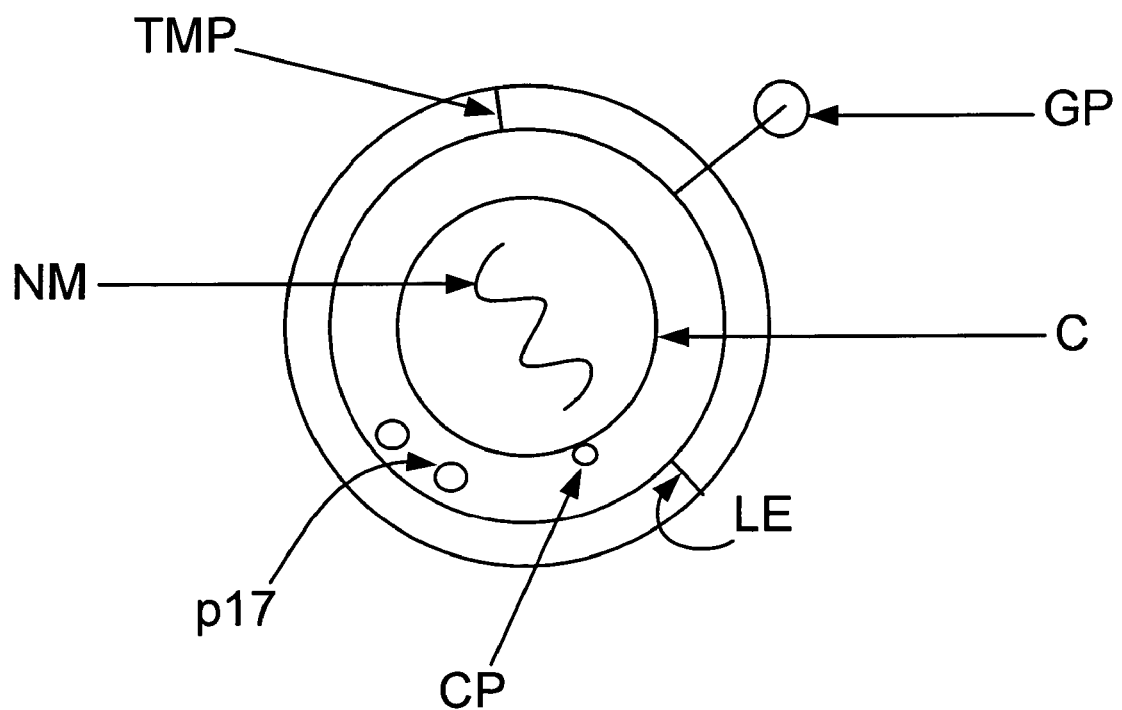
FIG. 4 is a schematic representation of an HIV viral particle showing the lipid containing envelope (LE) or bilayer derived from a host cell, the capsid (C), nuclear material (NM) such as RNA, surface glycoproteins (GP) such as gp120 and gp41, transmembrane proteins (TMP), p17 matrix protein, and capsid proteins (CP) such as p24.

The kits of the present invention generally comprise containers used for different purposes and are depicted in FIGS. 1-3. A first container 10 generally contains one or more first extraction solvents 20. This first container 10 contains means 15 for removing the first extraction solvent from the opening 70 of the container 10. Such means may be a component of the first container 10 or a separate component adapted to function with the first container 10. Such means include, but are not limited to, any type of cap 15, spout, funnel, penetrable seal, penetrable diaphragm, tube 60, pipette, or other means for removing the one or more first extraction solvents 20 or for introducing a fluid 30 containing lipid-containing virus into the first container 10.

A second container 50 contains the fluid 30 containing lipid-containing virus to be delipidated.

In one embodiment, a third container 70 is used for mixing the fluid 30 containing lipid-containing virus to be delipidated and the first extraction solvent 20. Mixing can occur through agitation, inversion, shaking, or other means to agitate the third container 70 to a degree sufficient to mix the fluid 30 and the first extraction solvent 20 to form a mixture 72. After the mixing step, the first extraction solvent containing the dissolved lipids from the fluid or from the viruses separates from the fluid. At this point, the delipidated fluid may be removed through any means 75 such as pouring, decanting, pipetting, applying a vacuum connected to a tube or pipette, or any other means known to one of ordinary skill in the art of removing separated fluids.

A fourth container 80 optionally receives the delipidated fluid and modified viral particles 82 originating from the third container 70. Alternatively, the delipidated fluid containing the modified viral particles is administered into the patient through a tube, catheter, an intravenous line, an intraarterial line or other means without introduction into a fourth container 80.

In one embodiment, the first container 10 containing the first extraction solvent 20, has sufficient additional volume within it to receive the fluid 30 containing lipid-containing virus to be delipidated. In this embodiment, mixing of the first extraction solvent 20 and the fluid containing lipid-containing virus 30 to be delipidated occurs within the first container 10. In this embodiment, a separate container for mixing the fluid 30 and the first extraction solvent 20, referred to as the third container 70, is not required. After mixing occurs, the first extraction solvent containing the dissolved lipids separates from the delipidated fluid and the modified viral particles. At this point, the delipidated fluid and the modified viral particles may be introduced into another container, analogous to the fourth container described above, for subsequent introduction into a patient or for optional additional extraction of the first extraction solvent with a second extraction solvent 92.

In another embodiment, when a second extraction solvent 92 is optionally employed to assist in removal of the first extraction solvent 20, a fifth container 90 is included which contains the second extraction solvent 92. This second extraction solvent 92 may be added to the mixture 72 described above in the third container 70, mixed and then permitted to separate from the delipidated fluid and modified viral particles. Alternatively, the second extraction solvent 92 may be added to the fourth container 80 described above, mixed and then permitted to separate from the delipidated fluid and modified viral particles if additional removal of residual first extraction solvent is desired. In yet another alternative embodiment, the second extraction solvent 92 may be added to the first container 10 described above containing the mixture of the fluid 30 containing the lipid containing virus and the first extraction solvent 20, mixed, and then permitted to separate from the delipidated fluid and modified viral particles if mixing of the fluid 30 containing the lipid containing virus and the first extraction solvent 20, separation and additional extraction of the first extraction solvent 20 using a second extraction solvent 92 are all performed in the first container 10.

The containers described above may be graduated for easy determination of volume within a container.

Optionally, means for removing or introducing a biological fluid from a patient comprising a venipuncture system may be included in a kit. Such systems are well known to those skilled in the art of removing or replacing fluids, for example vascular fluids, including without limitation a vac tube, hypodermic syringe connected to an intravascular needle 62, 112, tubing 60, 110 or an intravascular needle 62, 112, connected through tubing 60, 110 to a bag for collection of blood. Any of these devices may be optionally incorporated into the kit. A sensor may be added to the kit for determining the level of a first extraction solvent and optionally a second extraction solvent in the delipidated fluid.

Suitable materials for use in any of the apparatus components as described herein include materials that are biocompatible, approved for medical applications that involve contact with internal body fluids, and in compliance with U.S. PV1 or ISO 10993 standards. Further, the materials should not substantially degrade during at least a single use, from for instance, exposure to the solvents used in the present invention. The materials should typically be sterilizable, preferably by radiation or ethylene oxide (EtO) sterilization. Such suitable materials should be capable of being formed into objects using conventional processes, such as, but not limited to, extrusion, injection molding and others. Materials meeting these requirements include, but are not limited to, nylon, polypropylene, polycarbonate, acrylic, polysulphone, polyvinylidene fluoride (PVDF), fluoroelastomers such as VITON, available from DuPont Dow Elastomers L.L.C., thermoplastic elastomers such as SANTOPRENE, available from Monsanto, polyurethane, polyvinyl chloride (PVC), polytetrafluoroethylene (PTFE), polyphenylene ether (PFE), perfluoroalkoxy copolymer (PFA), which is available as TEFLON PFA from E.I. du Pont de Nemours and Company, and combinations thereof.

Through the use of the kits and methods of the present invention, levels of lipid in lipid-containing viruses in a fluid are reduced, and the fluid, for example, delipidated plasma containing the modified viral particles may be administered to the patient. Such fluid contains modified viral particles that are not infective. These modified viral particles induce an immune response in the recipient to epitopes on the modified viral particles. Alternatively the modified viral particles may be further isolated from the delipidated fluid and combined with a pharmaceutically acceptable carrier, and optionally an adjuvant and administered as a vaccine composition to a human or an animal to induce an immune response in the recipient.

Vaccine Production

The modified viral particle, which is at least partially or substantially delipidated and has immunogenic properties is combined with a pharmaceutically acceptable carrier to make a composition comprising a vaccine. This vaccine composition is optionally combined with an adjuvant or an immunostimulant and administered to an animal or a human. It is to be understood that vaccine compositions may contain more than one type of modified viral particle or component thereof, in order to provide protection against more than one disease after vaccination. Such combinations may be selected according to the desired immunity. For example, preferred combinations may be, but are not limited to HIV and hepatitis or influenza and hepatitis. More specifically, the vaccine can comprise a plurality of modified viral particles having patient-specific antigens and modified viral particles having non-patient specific antigens or stock viral particles that have undergone the delipidation process of the present invention.

The remaining particles of the organism are retained in the delipidated biological fluid, and when reintroduced into the animal or human, are presumably ingested by phagocytes. The number of viral particles isolated and modified by the delipidation treatment is determined by counting the particles before and after treatment.

Administration of Vaccine Produced with the Method of the Present Invention

When a delipidated infectious organism, for example one in the form of a modified viral particle with exposed antigenic determinants, is administered to an animal or a human, it is typically combined with a pharmaceutically acceptable carrier to produce a vaccine, and optionally combined with an adjuvant or an immunostimulant as known to one of ordinary skill in the art. The vaccine formulations may conveniently be presented in unit dosage form and may be prepared by conventional pharmaceutical techniques known to one of ordinary skill in the art. Such techniques include uniformly and intimately bringing into association the active ingredient and the liquid carriers (pharmaceutical carrier(s) or excipient(s)). Formulations suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers—for example, sealed ampules and vials—and may be stored in a freeze-dried (lyophilized) condition requiring only the addition of the sterile liquid carrier, for example, water for injections, immediately prior to use. The vaccine may be stored at temperatures of from about 4° C. to −100° C. The vaccine may also be stored in a lyophilized state at different temperatures including room temperature. Extemporaneous injection solutions and suspensions may be prepared from sterile powders, granules and tablets commonly used by one of ordinary skill in the art. The vaccine may be sterilized through conventional means known to one of ordinary skill in the art. Such means include, but are not limited to filtration, radiation and heat. The vaccine of the present invention may also be combined with bacteriostatic agents, such as thimerosal, to inhibit bacterial growth.

Preferred unit dosage formulations are those containing a dose or unit, or an appropriate fraction thereof, of the administered ingredient. It should be understood that in addition to the ingredients, particularly mentioned above, the formulations of the present invention may include other agents commonly used by one of ordinary skill in the art.

The vaccine may be administered through different routes, such as oral, including buccal and sublingual, rectal, parenteral, aerosol, nasal, intramuscular, subcutaneous, intradermal, intravenous, intraperitoneal, and topical.

The vaccine of the present invention may be administered in different forms, including but not limited to solutions, emulsions and suspensions, microspheres, particles, microparticles, nanoparticles, and liposomes. It is expected that from about 1 to 5 dosages may be required per immunization regimen. One of ordinary skill in the medical or veterinary arts of administering vaccines will be familiar with the amount of vaccine to be administered in an initial injection and in booster injections, if required, taking into consideration, for example, the age and size of an a patient.

Vaccination Schedule

The vaccines of the present invention may be administered before, during or after an infection. The vaccine of the present invention may be administered to either humans or animals. In one embodiment, the viral load (one or more viruses) of a human or an animal may be reduced by delipidation treatment of the plasma. The same individual may receive a vaccine directed to the one or more viruses, thereby stimulating the immune system to combat against the virus that remains in the individual. The optimal time for administration of the vaccine is about one to three months before the initial infection. However, the vaccine may also be administered after initial infection to ameliorate disease progression or to treat the disease.

Adjuvants

A variety of adjuvants known to one of ordinary skill in the art may be administered in conjunction with the modified viral particles in the vaccine composition. Such adjuvants include, but are not limited to the following: polymers, co-polymers such as polyoxyethylene-polyoxypropylene co-polymers, including block co-polymers; polymer P1005; monotide ISA72; Freund's complete adjuvant (for animals); Freund's incomplete adjuvant; sorbitan monooleate; squalene; CRL-8300 adjuvant; alum; QS 21, muramyl dipeptide; trehalose; bacterial extracts, including mycobacterial extracts; detoxified endotoxins; membrane lipids; water-in-oil mixtures, water-in-oil-in-water mixtures or combinations thereof.

Suspending Fluids and Carriers

A variety of suspending fluids or carriers known to one of ordinary skill in the art may be employed to suspend the vaccine composition. Such fluids include without limitation: sterile water, saline, buffer, or complex fluids derived from growth medium or other biological fluids. Preservatives, stabilizers and antibiotics known to one of ordinary skill in the art may be employed in the vaccine composition.

The following experimental examples are illustrative in showing that a delipidation process of the viral particle occurred and in particular, that the viral particle was modified and noted to exhibit a positive immunogenic response in the species from which it was derived. It will be appreciated that other embodiments and uses will be apparent to those skilled in the art and that the invention is not limited to these specific illustrative examples or preferred embodiments.

EXAMPLE 1

A. Delipidation of Serum Produces Duck Hepatitis B Virus (DHBV) having Reduced Infectivity A standard duck serum pool (Camden) containing $10^6$ $ID_{50}$ doses of DHBV was used. $ID_{50}$ is known to one of ordinary skill in the art as the infective dosage (ID) effective to infect 50% of animals treated with the dose. Twenty-one ducklings were obtained from a DHBV negative flock on day of hatch. These ducklings were tested at purchase and shown to be DHBV DNA negative by dot-blot hybridization.

The organic solvent system was mixed in the ratio of 40% butanol to 60% diisopropyl ether. The mixed organic solvent system (4 ml) was mixed with the standard serum pool (2 ml) and gently rotated for 1 hour at room temperature. The mixture was centrifuged at 400×g for 10 minutes and the lower aqueous phase (containing the plasma) removed at room temperature. The aqueous phase was then mixed with an equal volume of diethyl ether and centrifuged as before to remove any remaining lipid/solvent mixture. The aqueous phase was again removed and mixed with an equal volume of diethyl ether and re-centrifuged. The aqueous phase was removed and any residual diethyl ether was removed by airing in a fume cabinet at room temperature for about 1 hour. The delipidated plasma, with or without viral particles was stored at −20° C.

The positive and negative control duck sera were diluted in phosphate buffered saline (PBS). Positive controls: 2 ml of pooled serum containing $10^6$$ID_{50}$ doses of DHBV was mixed with 4 ml of PBS. Negative controls: 2 ml of pooled DHBV negative serum was mixed with 4 ml of PBS. Residual infectivity was tested by inoculation of 100 µl of either test sample (n=7), negative (n=7) or positive (n=7) controls into the peritoneal cavities of day-old ducks. Controls were run with DHBV negative serum treated with organic solvents and subsequently mixed with PBS and injected into recipient ducks.

One of the positive control ducks died between 4 and 6 days of age and was excluded from further analysis. A further 3 positive control ducks died between 9 and 10 days of age, and two treatment and one negative control died on day 11. It was decided to terminate the experiment. The remaining ducklings were euthanized on day 12 with sodium pentibarbitone, i.v., and their livers removed for DHBV DNA analysis as described by Deva et al (*J. Hospital Infection* 33:119-130, 1996). All seven negative control ducks remained DHBV negative. Livers of all six positive control ducks were DHBV positive. All seven test ducks remained negative for DHBV DNA in their liver.

Delipidation of serum using the above solvent system resulted in DHBV having reduced infectivity. None of the ducklings receiving treated serum became infected. Although the experiment had to be terminated on day 12 instead of day 14, the remaining positive control ducks were positive for DHBV (3/3 were DHBV positive by day 10). This suggests that sufficient time had elapsed for the treated ducks to become DHBV positive in the liver and that the premature ending of the experiment had no bearing on the results.

B. Delipidated DHBV Positive Serum as a Vaccine to Prevent DHBV Infection

The efficacy of the delipidation procedure to provide a patient specific "autologous" vaccine against Duck Hepatitis B Virus (DHBV) was examined. Approximately 16 Pekin cross ducklings were obtained from a DHBV negative flock of ducklings on the day of hatch. The ducklings were tested and determined to be DHBV negative by analysis of DHBV DNA using dot-blot hybridization. The ducks were divided into the following three groups:

TABLE 1

| | # of Ducks | Vaccine Administered | Results |
|---|---|---|---|
| GROUP 1 | 6 | Test Vaccine | 5/6 ducks remained DHBV negative following challenge |
| GROUP 2 | 4 | Sham Vaccine [Glutaraldehyde-inactivated DHBV (chemical kill)] | 4/4 ducks became DHBV positive following challenge. |
| GROUP 3 (Control) | 6 | Mock Vaccine [Phosphate Buffered Saline (PBS)] | 6/6 ducks became DHBV positive following challenge. |

1. Glutaraldehyde Inactivation

Glutaraldehyde inactivation was achieved as known by those of ordinary skill in the art by fixation with a dilute solution of glutaraldehyde at about 1:250. Glutaraldehyde is a well known cross linking agent.

2. Delipidation Procedure

An organic solvent system was employed to perform delipidation of serum. The solvent system consisted of a ratio of 40% butanol (analytical reagent grade) and 60% diisopropyl ether and was mixed with the serum in a 2:1 ratio. Accordingly, 4 ml of the organic solvent was mixed with 2 ml of the serum and rotated for 1 hour. This mixture was centrifuged at approximately 400×g for 10 minutes followed by removal of the aqueous phase. The aqueous phase was then mixed with an equal volume of diethyl ether and centrifuged at 400×g for 10 minutes. Next, the aqueous phase was removed and mixed with an equal volume of diethyl ether and rotated end-over-end at 30 rpm for about 1 hour, and centrifuged at 400×g for 10 minutes. The aqueous phase was removed and the residual diethyl ether was removed through evaporation in a fume cabinet for approximately 10 to 30 minutes. The treated serum remained following removal of diethyl ether and was used to produce the vaccine. The delipidation procedure control involved subjecting the DHBV negative serum to the same delipidation procedure as the DHBV positive serum.

TABLE 2

| 3. Vaccine Production | | | |
|---|---|---|---|
| Vaccine Type | First Dose (injected with 200 μl of respective vaccine into peritoneal cavity on Day 8 post-hatch) | Second Dose (injected with 300 μl of respective vaccine intramuscularly on Day 16 post-hatch) | Third Dose (injected with 300 μl of respective vaccine intramuscularly on Day 22 post-hatch) |

TABLE 2-continued 3. Vaccine Production

| | | | |
|---|---|---|---|
| TEST | A 40 µl aliquot of the delipidated serum was mixed with 1960 µl of phosphate buffered saline (PBS) | A 40 µl aliquot of the delipidated serum was mixed with 1960 µl of PBS and then emulsified in 1000 µl of Freund's Incomplete Adjuvant. | A 200 µl aliquot of the delipidated serum was mixed with 1800 µl of PBS and then emulsified in 1000 µl of Freund's Incomplete Adjuvant. |
| SHAM (DHBV SERUM CONTROL) | A 200 µl aliquot of DHBV positive serum pool #4 (20.4.99) was mixed with 300 µl of PBS and 100 µl of a 2% glutaraldehyde solution (Aidal Plus from Whiteley Chemicals) and incubated for 10 minutes to inactivate the DHBV. A 40 µl aliquot of the inactivated serum/PBS mixture was added to 1960 µl PBS. | A 200 µl aliquot of DHBV positive serum pool #4 (20.4.99) was mixed with 300 µl of PBS and 100 µl Aidal Plus (Whiteley Chemicals) and incubated for 10 minutes to inactivate the DHBV. A 40 µl aliquot of the inactivated serum/PBS mixture was added to 1960 µl PBS and emulsified in 1000 µl Freunds Incomplete Adjuvant. | A 200 µl aliquot of DHBV positive serum pool #4 (20.4.99) was mixed with 300 µl of PBS and 100 µl Aidal Plus (Whiteley Chemicals) and incubated for 10 minutes to inactivate the DHBV. A 40 µl aliquot of the inactivated serum/PBS mixture was added to 1960 µl PBS and emulsified in 1000 µl Freunds Incomplete Adjuvant. |
| MOCK (DHBV NEGATIVE CONTROL) | PBS | A 2000 µl aliquot of PBS was emulsified in 1000 µl Freunds Incomplete Adjuvant. | A 2000 µl aliquot of PBS was emulsified in 1000 µl Freunds Incomplete Adjuvant. |

4. Experimental Procedure

Ducks were challenged with 1000 µl of DHBV positive serum (serum pool 20.1.97) on day 29, post-hatch. Serum pool 20.1.97 was shown to have $1.8 \times 10^{10}$ genome equivalent (gev)/ml by dot-blot hybridization. One genome equivalent (gev) is approximately one viral particle. Ducks were bled prior to full vaccination on days 1 and 10, prior to challenge on days 17 and 23, and post challenge on days 37, 43 and 52. Their serum was tested for DHBV DNA by dot-blot hybridization as described by Deva et al. (1995). Ducks were euthanized on day 58 and their livers removed, the DNA extracted and tested for the presence of DHBV by dot-blot hybridization as described by Deva et al. (1995).

5. Analysis of Results
   a. Test ducks
      i. Five of the 6 test ducks vaccinated with the test vaccine remained negative for DHBV DNA in the serum and liver following challenge. One test duck became positive for DHBV following challenge.
   b. Sham vaccinated ducks
      i. All 4 of the ducks vaccinated with glutaraldehyde inactivated serum became DHBV positive following challenge with DHBV.
   c. Mock vaccinated ducks
      i. Five of the 6 mock-vaccinated negative control ducks became DHBV positive following challenge.

The Chi-square analysis was used to compare differences between treatments. Significantly more control ducks (mock vaccinated) became DHBV positive following challenge than the ducks vaccinated with delipidated serum (p<0.05).

Vaccination of ducklings with delipidated DHBV positive serum using the above protocol resulted in prevention of DHBV infection following challenge with DHBV positive serum in 5 of 6 ducklings. This suggests that the delipidated serum vaccine is capable of inducing a positive immunogenic response in vaccinated ducks. It is further believed that the delipidation process exposed patient-specific antigens that were previously unexposed and/or caused a structural change in the viral particle structure to enable the positive immunogenic response. In comparison 5 of 6 mock vaccinated and 4 of 4 sham-vaccinated ducks became DHBV positive following vaccination suggesting no induction of immunity in these ducks due to lack of immune response.

EXAMPLE 2

A. Delipidation of Cattle Pestivirus (bovine viral diarrhea virus, BVDV), as a Model for Hepatitis C A standard cattle pestivirus isolate (BVDV) was used in these experiments. This isolate, "Numerella" BVD virus, was isolated in 1987 from a diagnostic specimen submitted from a typical case of 'Mucosal Disease' on a farm in the Bega district of New South Wales (NSW), Australia. This virus is non-cytopathogenic, and reacts with all 12 of a panel of monoclonal antibodies raised at the Elizabeth Macarthur Agricultural Institute (EMAI), NSW, Australia, as typing reagents. Therefore, this virus represents a 'standard strain' of Australian BVD viruses.

The Numerella virus was grown in bovine MDBK cells tested free of adventitious viral agents, including BVDV. The medium used for viral growth contained 10% adult bovine serum derived from EMAI cattle, all of which tested free of BVDV virus and BVDV antibodies. This serum supplement has been employed for years to exclude the possibility of adventitious BVDV contamination of test systems, a common failing in laboratories worldwide that do not take precautions to ensure the test virus is the only one in the culture system. Using these tested culture systems ensured high-level replication of the virus and a high yield of infectious virus. Titration of the final viral yield after 5 days growth in MDBK cells showed a titer of $10^{6.8}$ infectious viral particles per ml of clarified (centrifuged) culture medium.

1. Treating Infectious BVDV 100 ml of tissue-culture supernatant, containing 1068 viral particles/ml, was harvested from a 150 cm² tissue-culture flask. The supernatant was clarified by centrifugation (cell debris pelleted at 3000 rpm, 10 min, 4° C.) and 10 ml set aside as a positive control for animal inoculation (non-treated virus). The remaining 90 ml, containing $10^{7.75}$ infectious virus, was treated using the following protocol: 180 ml of a solvent mixture butanol:diisopropyl ether (DIPE) (2:1) was added to a 500 ml conical flask and mixed by swirling. The mixture was then shaken for 60 min at 30 rpm at room temperature on an orbital shaker. It was then centrifuged for 10 min at 400×g at 4° C., after which the organic solvent phase was removed and discarded. In subsequent steps, the bottom layer (aqueous phase) was removed from beneath the organic phase, improving yields considerably.

The aqueous phase, after the butanol:DIPE treatment, was washed four times with an equal volume of fresh diethyl ether (DEE) to remove all contaminating traces of butanol. After each washing, the contents of the flask was swirled to ensure even mixing of both aqueous and solvent phases before centrifugation as above (400×g, 10 min, 4° C.). After four washes, the aqueous phase was placed in a sterile beaker covered with a sterile tissue fixed to the top of the beaker with a rubber band to prevent contamination and placed in a fume hood running continuously overnight (16 hr) to remove all remaining volatile ether residue from the inactivated viral preparation. Subsequent culture of the treated material demonstrated no contamination. The treated viral preparation was then stored at 4° C. under sterile conditions until inoculation into tissue culture or animals to test for any remaining infectious virus.

2. Testing of Treated BVDV preparation a. Tissue-culture Inoculation 2 ml of the solvent-treated virus preparation, expected to contain about $10^{7.1}$ viral equivalents, was mixed with 8 ml tissue-culture medium Minimal Eagles Medium (MEM) containing 10% tested-free adult bovine serum and adsorbed for 60 min onto a monolayer of MDBK cells in a 25 cm² tissue-culture flask. As a positive control, 2 ml of non-treated or substantially lipid-containing infectious virus (also containing about $10^{7.1}$ viral equivalents) was similarly adsorbed on MDBK cells in a 25 cm² tissue-culture flask. After 60 min, the supernatant was removed from both flasks and replaced with normal growth medium (+10% ABS). The cells were then grown for 5 days under standard conditions before the MDBK cells were fixed and stained using a standard immunoperoxidase protocol with a mixture of 6 BVDV-specific monoclonal antibodies (EMAI panel, reactive with 2 different BVD viral proteins).

There were no infected cells in the monolayer of MDBK cells that was inoculated with the organic solvent treated virus. In contrast, approximately 90% of the cells in the control flask (that was inoculated with non-inactivated BVDV) were positive for virus as shown by heavy, specific, immunoperoxidase staining. These results showed that, under in vitro testing conditions, no infectious virus remained in the treated, at least partially delipidated BVDV preparation.

b. Animal Inoculation

An even more sensitive in vivo test is to inoculate naïve (antibody negative) cattle with the at least partially delipidated virus preparation. As little as one infectious viral particle injected subcutaneously in such animals is considered to be an infectious cow dose, given that entry into cells and replication of the virus is extremely efficient for BVDV. A group of 10 antibody-negative steers (10-12 months of age) were randomly allocated to 3 groups.

The first group of 6 steers was used to test whether BVDV had reduced infectivity. The same at least partially delipidated preparation of BVDV described above was used in this example. Two steers were inoculated with a vaccine having at least partially delipidated viral particles to act as a positive control for the vaccine group. These two positive control animals were run under separate, quarantined conditions to prevent them from infecting other animals when they developed a transient viraemia after infection (normally at 4-7 days after receiving live BVDV virus). The two remaining steers acted as negative "sentinel" animals to ensure there was no naturally-occurring pestivirus transmission within the vaccinated group of animals. Antibody levels were measured in all 10 animals using a validated, competitive ELISA developed at EMAI. This test has been independently validated by CSL Ltd and is marketed by IDEXX Scandinavia in Europe.

The six animals in the first group each received a subcutaneous injection of 4.5 ml of the at least partially delipidated BVDV preparation, incorporated in a commercial adjuvant. Since each ml of the at least partially delipidated preparation contained $10^{6.8}$ viral equivalents, the total viral load before the delipidation process was $10^{7.4}$ tissue culture infectious doses $(TCID)_{50}$. The positive-control animals received 5 ml each of the non-delipidated preparation, that is, $10^{7.5}$ $TCID_{50}$ injected subcutaneously in the same way as for the first group. The remaining two 'sentinel' animals were not given any viral antigens, having been grazed with the first group of animals throughout the trial to ensure there was no natural pestivirus activity occurring in the group while the trial took place.

There was no antibody development in any of the vaccinated steers receiving the at least partially delipidated BVD virus preparation until a second dose of vaccine was given. Thus, at 2 and 4 weeks after a single dose, none of the 6 steers seroconverted showing that there was no infectious virus left in a total volume of 27 ml of the at least partially delipidated virus preparation. This is the equivalent of a total inactivation of $10^{8.2}$ $TCID_{50}$. In contrast, there were high levels of both anti-E2 antibodies (neutralizing antibodies) and anti-NS3 antibodies at both 2 and 4 weeks after inoculation in the two steers receiving 5 ml each of the viral preparation prior to delipidation. This confirmed the infectious nature of the virus prior to delipidation. These in vivo results confirm the findings of the in vitro tissue-culture test. The two 'sentinel' animals remained seronegative throughout, showing the herd remained free of natural pestivirus infections.

The panel of monoclonal antibodies used detected host antibodies directed against the major envelope glycoprotein (E2), which is a glycoprotein incorporated in the lipid envelope of the intact virus. The test systems also detected antibodies directed against the non-structural protein, NS3 that is made within cells infected by the virus. This protein has major regulatory roles in viral replication and is not present within the infectious virus. There was no evidence in the vaccinated cattle that infectious virus was present, indicating all infectious viral particles had been destroyed. All pestiviruses are RNA viruses. Therefore, there was no viral DNA present in the delipidated preparation. These results demonstrate the efficacy of the present method to at least partially delipidate virus such that substantially no infectious virus is found in animals receiving the delipidated virus.

B. Delipidated BVDV Preparation as a Vaccine in Steers

All six steers that had received an initial dose of 4.5 ml of the at least partially delipidated BVDV preparation described in above in Section A were again injected subcutaneously with a similar dose at 4 weeks after the first priming dose. At this time there were no antibody responses after the initial dose. It is normal for an animal to react after the second dose. Strong secondary immune responses for anti-E2 antibody levels (equivalent to serum neutralizing antibodies SNT) were observed in 3 of the 6 steers at 2 weeks after the second dose of the at least partially delipidated virus. This response was more than 70% inhibition in a competitive ELISA. The remaining 3 animals showed weak antibody responses (23-31% inhibition).

In contrast to the anti-E2 antibody responses, only one animal developed a strong anti-NS3 antibody response (93% inhibition) at 2 weeks after the second dose of at least partially delipidated BVDV. A second animal had a weak anti-NS3 response (29% inhibition) and four animals showed no antibody following administration of 2 doses. This was not unexpected since similar responses following administration of at least partially delipidated BVDV vaccines have been observed previously. The antibody levels in steers following 2 doses of the at least partially delipidated BVDV preparation demonstrate its potential as a vaccine since antiE2 antibody levels were measurable in all 6 vaccinated steers at 2 weeks after the second dose.

EXAMPLE 3

Use of Delipidated SIV to Induce or Augment SIV Specific Humoral and CD4+ T Cell Memory Responses in Mice—a Model for a New Auto-vaccination Strategy Against Lentiviral Infection The following studies focused on the simian equivalent of human HIV, termed SIV. The purpose was to utilize delipidated SIVmac251 (an uncloned highly pathogenic isolate of SIV) to carry out studies to determine the relative immunogenicity of the delipidated virus in mice. The complete nucleotide sequence of an infectious clone of simian immunodeficiency virus of macaques, SIVmac239, has been determined. Virus produced from this molecular clone causes AIDS in rhesus monkeys in a time frame suitable for laboratory investigation. The proviral genome including both long terminal repeats is 10,279 base pairs in length and contains open reading frames for gag, pol, vif, vpr, vpx, tat, rev, and env. The nef gene contains an in-frame premature stop after the 92nd codon. At the nucleotide level, SIVmac239 is closely related to SIVmac251 (98%) and SIVmac142 (96%). (Regier D A, Desrosiers Annual Review Immunology. 1990;8:557-78.)

Experiments were performed to determine the minimal dose of delipidated simian immunodeficiency virus (SIV) that would produce a readily recognizable boosting of the virus specific humoral and/or cellular immune response in previously primed Balb/c mice. All experiments were carried out in a BSL3 facility.

The immunogenicity of the delipidated virus preparation was compared with an aliquot of the same virus in its native form. The quality (titer of antibody, the conformational and linear epitope specificity of the antibody, the isotype content of the antibody and the function of the antibody) and quantity of antibody induced by immunization of mice with equivalent protein amounts of the non-delipidated and delipidated virus preparation were ascertained as described below. Total protein from an aliquot of wild type virus and total protein recovered following delipidation of the same aliquot of virus were determined using standard quantitative protein assay (Biorad, BCA kit assay, Rockford, Ill.). The total protein profile was determined using SDS-PAGE analysis of the wild type virus and the delipidated virus preparation and the relative epitope preservation was ascertained by Western Blot comparison of wild type with delipidated virus.

Equivalent protein amounts of the chemically treated wild type and the delipidated virus were analyzed for their ability to boost virus specific immune response in groups of mice. The sera from these immunized mice were assayed by ELISA and Western Blot analysis for reactivity against native wild type and for comparison the delipidated virus preparation. Spleen cells were assayed for their CD4 and CD8 SIV virus env and gag specific immune response enhancing capacity as outlined below. Standard statistical analyses were performed for the analysis of the data.

Four to six week old healthy female Balb/c mice from the Jackson labs, Bar Harbor, Me were purchased and housed in the BSL2/3 mouse housing facility at Emory University. Twenty Balb/c mice were each immunized subcutaneously with 25 ug of protein of 2-2 dithiopyridine-inactivated SIVmac251 incorporated in an equal volume of Freunds incomplete adjuvant.

A sufficient quantity of SIVmac251 was delipidated to provide the amount needed for boosting these mice per schedule. Delipidation consisted of incubating SIVmac251 with 10% DIPE in phosphate buffered saline (PBS). 1.0 ml of a 10% DIPE solution in PBS was prepared and mixed on a vortexer until it appeared cloudy.

The virus preparation: A 1 ml tube from Advanced Biotechnologies SIVmac251 was used as seed stock (Sucrose Gradient Purified Virus 1 mg/ml). The supplier reported a titer of $10^{6.7}$ with total protein of 1.074 mg/mL (Pierce BCA protein method) and virus particle count of $6.95^{10}$/ml (EM). It was confirmed that the virus had a titer of $10^{70}$ using CEMx174, the first time as a rapid assay, and the second time in quadruplicate cultures/dilution. A measurement of p27 in this preparation revealed a value of 106 ug/ml. Next, 25 µl of the undiluted viral stock was introduced into 0.6 ml clear snap-cap polypropylene Eppendorf tube. 1 Then, 2.5 µl of 10% DIPE solution was added into the Eppendorf tube containing virus and vortexed for 15 seconds. The tube was spun (using an Eppendorf 5810R centrifuge) at room temp at 1000×g for 2 minutes. No bulk solvent was removed. The solvent was removed by vacuum centrifugation (Speedvac Concentrator Model SVC200H) at 2000 rpm with no heat for 30 minutes. The volume in the tube was adjusted to 25 µl with PBS. Total protein recovery was measured using a Pierce BCA protocol. Gels (12% SDS-PAGE) were employed for specific protein recoveries (env protein, pol protein, gp41, p27 and gag protein) and stained with Coomasie Blue and provided semi-quantitative results using OD. Western blots were run using serum from SIV-infected monkeys to measure envelope protein, gp66, gp41, p27, gag, and p6 gag. The viral infectivity of the preparation was determined using a luciferase assay and CEM-174 cells. The virus titer was $10^{4.5}$, a 2.5 log reduction from that measured in undelipidated stock. This delipidated SIV preparation appears to retain greater than 90% of the major protein constituents of SIVmac251 such as the gag and env proteins.

Next, the immunogenicity of the modified viral preparation was determined in the twenty adult female Balb/c mice described above that were each immunized subcutaneously with 25 ug of protein of 2-2 dithiopyridine-inactivated SIVmac251. On day 14, groups 3-6 were boosted with 10 ug to 0.01 ug (based on total protein of stock) of delipidated virus in 0.5 ml normal saline. The estimated actual virus protein content was equal to 1/10 that of total protein based on the ratio of total protein/p27 protein in stock. The mice were injected with the delipidated vaccine composition as follows:

TABLE 3

| Groups (containing 4 mice each) | Initial Immunization s.c. 2-2 dithiopyridine-inactivated SIV mac251 | Day 14 - Booster Injections i.v. |
| --- | --- | --- |
| GROUP 1 - Control | Non-immunized | Administered-saline without delipidated virus |
| GROUP 2 | Immunized | Not administered |
| GROUP 3 | Immunized | 0.5 ml saline + 10 ug of delipidated virus |
| GROUP 4 | Immunized | 0.5 ml saline + 1.0 ug of delipidated virus |
| GROUP 5 | Immunized | 0.5 ml saline + 0.1 ug of delipidated virus |
| GROUP 6 | Immunized | 0.5 ml saline + 0.01 ug of delipidated virus |

Four days after the booster injection, the mice were anesthetized and blood was collected via retro-orbital puncture and intra-cardiac puncture. About 0.5 ml of blood was collected from each mouse, primarily from intra-cardiac puncture. The blood was permitted to clot at room temperature. The spleen of each mouse was aseptically removed and transported to the lab under double bag containment. The clotted blood from each mouse was centrifuged at about 450×g at room temperature, and serum was collected from tube, transferred to a sterile tube, and stored at −70° C. until use. ELISA was performed to determine antibody titers against SIV for each serum sample.

SIV ELISA Protocol

Stocks of positive and negative serum and fluids to be tested were frozen in aliquots to be used on every plate to standardize each run.

Coated Corning Easy-Plates were washed with 100 ul per well of poly-1-lysine at a concentration of 10 ug per ml of PBS, pH 7.2-7.4. Plates were covered and incubated overnight at 4° C. Several plates were coated at one time and stored for subsequent use. Next, excess polylysine was removed and the plate dried for a few minutes. About 100 ul of 2% Triton-X was added to 100 ul of the stock ABI SIV-mac251 the samples sat for 5 minutes. Next, 50 ul of coating buffer of pH 9.6 was added. Next, 100 ul of the viral antigen was added to each well of 5 plates, which were covered and incubated at 4° C. overnight.

After the overnight incubation, wells were washed 3 times with PBS-T. The wells then received 200 ul per well of 2% nonfat dry milk in PBS for one hour at room temperature to block non-specific binding. Excess fluid was removed. About 100 ul of test or control serum diluted at 1/100 in 10% RPMI 1640 or PBS with 10% calf serum was added to duplicate wells and incubated for 2 hours at 37° C. Wells were washed 4 times with PBS-T. Next 100 ul of Southern Biotech (from Fisher) alkaline phosphatase anti Mouse IgG (diluted 1/800 in media or PBS with 10% calf serum) was added and incubated 1 hour at 37° C. Wells were washed 4 times with PBS-T.

The BIORAD Alkaline Phosphatase Substrate kit was used to develop a reaction product. One substrate tablet was added for each 5 ml of 1× buffer and mixed. Next 100 ul was added per well and evaluated at about 5, 10, 15, 30 and then at 1 hour intervals for color development.

Blank readings were obtained from the media controls when the positive control was above 1.500 and the negative control was 0.100 to 0.200 for the serum. The results were then recorded and the means and the standard deviations of the negative control, positive control and the experimental samples were calculated. The negative cutoff value was the mean of the negative control plus 0.150.

Immunogenicity Results

The immunogenicity of the delipidated SIV virus preparation in mice was examined with an ELISA assay. The mean optical density (O.D.) was examined at 405 nm at various dilutions of serum. Table 4 provides the results of the ELISA test on serum samples.

TABLE 4

| Serum dil. | No boost | 10 ug boost | 1 ug boost | 0.1 ug boost | 0.01 ug boost |
| --- | --- | --- | --- | --- | --- |
| 1/100 | 2.541 | 3.663 | 3.289 | 2.846 | 2.627 |
| 1/500 | 1.035 | 2.86 | 2.055 | 1.458 | 1.257 |
| 1/2500 | 0.449 | 1.239 | 0.855 | 0.601 | 0.445 |
| 1/12500 | 0.194 | 0.463 | 0.304 | 0.229 | 0.181 |
| 1/62500 | 0.127 | 0.151 | 0.153 | 0.129 | 0.123 |
| 1/312500 | 0.11 | 0.116 | 0.108 | 0.108 | 0.107 |

Analysis of Responses of Dissociated Spleen Cells Obtained from Immunized Mice

A single cell suspension of spleen cells was prepared from each individual mouse by gently teasing the splenic capsule and passing the cells through a 25 gauge needle. Spleen cells were dissociated into a single cell suspension in medium (RPMI 1640 supplemented with 100 ug/ml penicillin, 100 ug/ml streptomycin, 2 mM L-glutamine), washed twice in medium and subsequently adjusted to 10 million cells/ml. 0.1 ml of this cell suspension from each mouse was dispensed into each well of a 96 well round bottom microtiter plate containing medium. Remaining cells were cryopreserved. These spleen cell cultures were then assessed for the ability of CD4+ and CD8+ T cells to synthesize IFN-gamma by standard intracellular cytokine staining (ICC) and flow cytometry.

Two individual wells containing the duplicate cell cultures from an individual mouse received either a) 0.1 ml of medium containing 2 ug/ml of each of a pool of 9 SIV envelope (SE) peptides (n=14 pools), or b) 0.1 ml of medium containing a pool of 7 SIV gag (SG) peptides (n=17 pools). Each pool contained 2 ug/ml of 7 peptides each for SIV env and SIV gag. Controls consisted of spleen cell cultures that received media alone (background control) or a previously determined optimum concentration of phorbol myristic acetate (PMA 1 ug/ml)+ionomycin (0.25 ug/ml) for maximal IFN-gamma staining (positive control). The SIVenv peptides (n=49 individual peptides) were mixed in a grid fashion of a 7×7 matrix and the SIV gag peptides (n=72 peptides) were mixed in a grid fashion of a 9×8 matrix which permitted identification of individual peptide specific immune responses. The SIV env and gag peptides were synthetic 20 mer peptides that overlapped each other by 12 amino acids and encompassed the entire SIV env and gag sequence. Peptide pools were made to contain 2.0 ug/ml of each peptide. For each spleen cell preparation there were 36 wells of culture. The components of the 9 pools and 7 pools of env and gag overlapping peptides are described below. Shown are the peptides that compose the pools with their respective position within SIVmac239gag (SG) and env (SE).

TABLE 5

Pool arrangement of individual SIVmac239 env peptides.

7 SG Peptide pools

| | 1 | 2 | 3 | 4 | 5 | 6 | 7 |
|---|---|---|---|---|---|---|---|
| SG18 | 1 | 2 | 3 | 4 | 5 | 6 | 7 |
| SG19 | 8 | 9 | 10 | 11 | 12 | 13 | 14 |
| SG20 | 15 | 16 | 17 | G-6* | G-5* | 20 | 21 |
| SG21 | 22 | 23 | 24 | 25 | 26 | 27 | 28 |
| SG22 | 29 | 30 | 31 | 32 | 33 | 34 | 35 |
| SG23 | 36 | 37 | 38 | 39 | 40 | 41 | 42 |
| SG24 | 43 | 44 | 45 | 46 | 47 | 48 | 49 |

TABLE 6

Pool arrangement of individual SIVmac239 env peptides.

9 SE Peptide pools

| | 1 | 2 | 3 | 4 | 5 | 6 | 7 | 8 |
|---|---|---|---|---|---|---|---|---|
| SE9 | 1 | 2 | 3 | 4 | 5 | 6 | 7 | 8 |
| SE10 | 9 | 10 | 11 | 12 | 13 | 14 | 15 | 16 |
| SE11 | 17 | 18 | 19 | 20 | 21 | 22 | 23 | 24 |
| SE12 | 25 | 26 | 27 | 28 | 29 | 30 | 31 | 32 |
| SE13 | 33 | 34 | 35 | 36 | 37 | 38 | 39 | 40 |
| SE14 | 41 | 42 | 43 | 44 | 45 | 46 | 47 | 48 |
| SE15 | 49 | 50 | 51 | 52 | 53 | 54 | 55 | 56 |
| SE16 | 57 | 58 | 59 | 60 | 61 | 62 | 63 | 64 |
| SE17 | 65 | 66 | 67 | 68 | 69 | 70 | 71 | 72 |

TABLE 7

SIVmac239 gag overlapping peptides for epitope mapping

| | | | |
|---|---|---|---|
| SEQ ID NO: 1 | MGVRNSVLSGKKADELEKIRLR | SG1 | 1-22 |
| SEQ ID NO: 2 | KKADELEKIRLRPNGKKKYMLK | SG2 | 11-32 |
| SEQ ID NO: 3 | LRPNGKKKYMLKHVVWAANELD | SG3 | 21-42 |
| SEQ ID NO: 4 | LKHVVWAANELDRFGLAESLLE | SG4 | 31-52 |
| SEQ ID NO: 5 | LDRFGLAESLLENKEGCQKILS | SG5 | 41-62 |
| SEQ ID NO: 6 | LENKEGCQKILSVLAPLVPTGS | SG6 | 51-72 |
| SEQ ID NO: 7 | LSVLAPLVPTGSENLKSLYNTV | SG7 | 61-82 |
| SEQ ID NO: 8 | GSENLKSLYNTVCVIWCIHAEE | SG8 | 71-92 |
| SEQ ID NO: 9 | TVCVIWCIHAEEKVKHTEEAKQ | SG9 | 81-102 |
| SEQ ID NO: 10 | EEKVKHTEEAKQIVQRHLVVET | SG10 | 91-112 |
| SEQ ID NO: 11 | KQIVQRHLVVETGTTETMPKTS | SG11 | 101-122 |
| SEQ ID NO: 12 | ETGTTETMPKTSRPTAPSSGRG | SG12 | 111-132 |
| SEQ ID NO: 13 | TSRPTAPSSGRGGNYPVQQIGG | SG13 | 121-142 |
| SEQ ID NO: 14 | RGGNYPVQQIGGNYVHLPLSPR | SG14 | 131-152 |
| SEQ ID NO: 15 | GGNYVHLPLSPRTLNAWVKLIE | SG15 | 141-162 |
| SEQ ID NO: 16 | PRTLNAWVKLIEEKKFGAEVVP | SG16 | 151-172 |
| SEQ ID NO: 17 | IEEKKFGAEVVPGFQALSEGCT | SG17 | 161-182 |
| SEQ ID NO: 18 | VPGFQALSEGCTPYDINQMLNCVGD | G-6 | 171-195* |
| SEQ ID NO: 19 | GCTPYDINQMLNCVGDHQAA | G-5 | 180-199* |
| SEQ ID NO: 20 | NCVGDHQAAMQIIRDIINEEAAD | SG20 | 191-213 |
| SEQ ID NO: 21 | IIRDIINEEAADWDLQHPQPAP | SG21 | 202-223 |
| SEQ ID NO: 22 | ADWDLQHPQPAPQQGQLREPSG | SG22 | 212-233 |
| SEQ ID NO: 23 | APQQGQLREPSGSDIAGTTSSV | SG23 | 222-243 |
| SEQ ID NO: 24 | SGSDIAGTTSSVDEQIQWMYRQ | SG24 | 232-253 |
| SEQ ID NO: 25 | SVDEQIQWMYRQQNPIPVGNIY | SG25 | 242-263*(*) |
| SEQ ID NO: 26 | RQQNPIPVGNIYRRWIQLGLQK | SG26 | 252-273(*) |
| SEQ ID NO: 27 | IYRRWIQLGLQKCVRMYNPTNIL | SG27 | 262-284(*) |
| SEQ ID NO: 28 | KCVRMYNPTNILDVKQGPKEPF | SG28 | 273-294 |
| SEQ ID NO: 29 | ILDVKQGPKEPFQSYVDRFYKS | SG29 | 283-304 |

TABLE 7-continued

SIVmac239 gag overlapping peptides for epitope mapping

| SEQ ID NO: | Sequence | | Position |
|---|---|---|---|
| SEQ ID NO: 30 | PFQSYVDRFYKSLRAEQTDAAV | SG30 | 293-314 |
| SEQ ID NO: 31 | KSLRAEQTDAAVKNWMTQTLLI | SG31 | 303-324 |
| SEQ ID NO: 32 | AVKNWMTQTLLIQNANPDCKLV | SG32 | 313-334 |
| SEQ ID NO: 33 | LIQNANPDCKLVLKGLGVNPTL | SG33 | 323-344 |
| SEQ ID NO: 34 | LVLKGLGVNPTLEEMLTACQGV | SG34 | 333-354 |
| SEQ ID NO: 35 | TLEEMLTACQGVGGPGQKARLM | SG35 | 343-364 |
| SEQ ID NO: 36 | GVGGPGQKARLMAEALKEALAP | SG36 | 353-374 |
| SEQ ID NO: 37 | LMAEALKEALAPVPIPFAAAQQ | SG37 | 363-384 |
| SEQ ID NO: 38 | APVPIPFAAAQQRGPRKPIKCW | SG38 | 373-394 |
| SEQ ID NO: 39 | AQQRGPRKPIKCWNCGKEGHSA | SG39 | 382-403 |
| SEQ ID NO: 40 | KCWNCGKEGHSARQCRAPRRQG | SG40 | 392-413 |
| SEQ ID NO: 41 | SARQCRAPRRQGCWKCGKMDHV | SG41 | 402-423 |
| SEQ ID NO: 42 | RQGCWKCGKMDHVMAKCPDRQAG | SG42 | 411-433 |
| SEQ ID NO: 43 | HVMAKCPDRQAGFLGLGPWGKK | SG43 | 422-443 |
| SEQ ID NO: 44 | AGFLGLGPWGKKPRNFPMAQVH | SG44 | 432-453 |
| SEQ ID NO: 45 | KKPRNFPMAQVHQGLMPTAPPE | SG45 | 442-463 |
| SEQ ID NO: 46 | VHQGLMPTAPPEDPAVDLLKNY | SG46 | 452-473 |
| SEQ ID NO: 47 | PEDPAVDLLKNYMQLGKQQREK | SG47 | 462-483 |
| SEQ ID NO: 48 | NYMQLGKQQREKQRESREKPYK | SG48 | 472-493 |
| SEQ ID NO: 49 | EKQRESREKPYKEVTEDLLHLN | SG49 | 482-503 |
| SEQ ID NO: 50 | YKEVTEDLLHLNSLFGGDQ | SG50 | 492-510 |

*denotes peptides containing defined or (*)semi defined gag epitopes (156-158)

TABLE 8

Overlapping peptides in Env of SIVmac239 (25-mer with 13-mer overlapping)

| SEQ ID NO: | Sequence | | Position |
|---|---|---|---|
| SEQ ID NO: 51 | MGCLGNQLLIAILLLSVYGIYCTLY | SE1 | 1-25 |
| SEQ ID NO: 52 | LLLSVYGIYCTLYVTVFYGVPAWRN | SE2 | 13-37 |
| SEQ ID NO: 53 | YVTVFYGVPAWRNATIPLFCATKNR | SE3 | 25-49 |
| SEQ ID NO: 54 | NATIPLFCATKNRDTWGTITQCLPDN | SE4 | 37-61 |
| SEQ ID NO: 55 | RDTWGTTQCLPDNGDYSEVALNVTE | SE5 | 49-73 |
| SEQ ID NO: 56 | NGDYSEVALNVTESFDAWNNTVTEQ | SE6 | 61-85 |
| SEQ ID NO: 57 | ESFDAWNNTVTEQAIEDVWQLFETS | SE7 | 73-97 |
| SEQ ID NO: 58 | QAIEDVWQLFETSIKPCVKLSPLCI | SE8 | 85-109 |
| SEQ ID NO: 59 | SIKPCVKLSPLCITMRCNKSETDRW | SE9 | 97-121 |
| SEQ ID NO: 60 | TMRCNKSETDRWGLTKSITTTAST | SE10 | 109-133 |
| SEQ ID NO: 61 | WGLTKSITTTASTTSTTASAKVDMV | SE11 | 121-145 |
| SEQ ID NO: 62 | TTSTTASAKVDMVNETSSCIAQDNC | SE12 | 133-157 |
| SEQ ID NO: 63 | VTNETSSCIAQDNCTGLEQEQMISCK | SE13 | 145-169 |
| SEQ ID NO: 64 | CTGLEQEQMISCKFNMTGLKRDKKK | SE14 | 157-181 |

TABLE 8-continued

Overlapping peptides in Env of SIVmac239
(25-mer with 13-mer overlapping)

| SEQ ID NO: | Sequence | Label | Range |
|---|---|---|---|
| 65 | KFNMTGLKRDKKKEYNETWYSADLV | SE15 | 169-193 |
| 66 | KEYNETWYSADLVCEQGNNTGNESR | SE16 | 181-205 |
| 67 | VCEQGNNTGNESRCYMNHCNTSVIQ | SE17 | 193-217 |
| 68 | RCYMNHCNTSVIQESCDKHYWDAIR | SE18 | 205-229 |
| 69 | QESCDKHYWDAIRFRYCAPPGYALL | SE19 | 217-241 |
| 70 | RFRYCAPPGYALLRCNDTNYSGFMP | SE20 | 229-253 |
| 71 | LRCNDTNYSGFMPKCSKVVVSSCTR | SE21 | 241-265 |
| 72 | PKCSKVVVSSCTRMMETQTSTWFGF | SE22 | 253-277 |
| 73 | RMMETQTSTWFGFNGTRAENRTYIY | SE23 | 265-289 |
| 74 | FNGTRAENRTYIYWHGRDNRTIISL | SE24 | 277-301 |
| 75 | YWHGRDNRTIISLNKYYNLTMKCRR | SE25 | 289-313 |
| 76 | LNKYYNLTMKCRRPGNKTVLPVTIM | SE26 | 301-325 |
| 77 | RPGNKTVLPVTIMSGLVFHSQPIND | SE27 | 313-337 |
| 78 | MSGLVFHSQPINDRPKQAWCWFGGK | SE28 | 325-349 |
| 79 | DRPKQAWCWFGGKWKDAIKEVQTI | SE29 | 337-361 |
| 80 | KWKDAIKEVQTIVKHPRYTGTNNT | SE30 | 349-373 |
| 81 | IVKHPRYTGTNNTDKINLTAPGGGD | SE31 | 361-385 |
| 82 | TDKINLTAPGGGDPEVTFMWTNCRG | SE32 | 373-397 |
| 83 | DPEVTFMWTNCRGEFLYCKMNWFLN | SE33 | 385-409 |
| 84 | GEFLYCKMNWFLNWVEDRNTANQKP | SE34 | 397-421 |
| 85 | NWVEDRNTANQKPKEQHKRNYVPCH | SE35 | 409-433 |
| 86 | PKEQHKRNYVPCHIRQIINTWHKVG | SE36 | 421-445 |
| 87 | HIRQIINTWHKVGKNVYLPPREGDL | SE37 | 433-457 |
| 88 | GKNVYLPPREGDLTCNSTVTSLIAN | SE38 | 445-469 |
| 89 | LTCNSTVTSLIANIDWIDGNQTNIT | SE39 | 457-481 |
| 90 | NIDWIDGNQTNITMSAEVAELYRLE | SE40 | 469-493 |
| 91 | TMSAEVAELYRLELGDYKLVEITPI | SE41 | 481-505 |
| 92 | ELGDYKLVEITPIGLAPTDVKRYTT | SE42 | 493-517 |
| 93 | IGLAPTDVKRYTTGGTSRNKRGVFV | SE43 | 505-529 |
| 94 | TGGTSRNKRGVFVLGFLGFLATAGS | SE44 | 517-541 |
| 95 | VLGFLGFLATAGSAMGAASLTLTAQ | SE45 | 529-553 |
| 96 | SAMGAASLTLTAQSRTLLAGIVQQQ | SE46 | 541-565 |
| 97 | QSRTLLAGIVQQQQLLDVVKRQQE | SE47 | 553-577 |
| 98 | QQQLLDVVKRQQELLRLTVWGTKNL | SE48 | 565-589 |
| 99 | ELLRLTVWGTKNLQTRVTAIEKYLK | SE49 | 577-601 |
| 100 | LQTRVTAIEKYLKDQAQLNAWGCAF | SE50 | 589-613 |
| 101 | KDQAQLNAWGCAFRQVCHTTVPWPN | SE51 | 601-625 |
| 102 | FRQVCHTTVPWPNASLTPKWNNETW | SE52 | 613-637 |

TABLE 8-continued

Overlapping peptides in Env of SIVmac239
(25-mer with 13-mer overlapping)

| SEQ ID NO: | Sequence | Label | Range |
|---|---|---|---|
| 103 | NASLTPKWNNETWQEWERKVDFLEE | SE53 | 625-649 |
| 104 | WQEWERKVDFLEENITALLEEAQIQ | SE54 | 637-661 |
| 105 | ENITALLEEAQIQQEKNMYELQKLN | SE55 | 649-673 |
| 106 | QQEKNMYELQKLNSWDVFGNWFDLA | SE56 | 661-685 |
| 107 | NSWDVFGNWFDLASWIKYIQYGVYI | SE57 | 673-697 |
| 108 | ASWIKYIQYGVYIVVGVILLRIVIY | SE58 | 685-709 |
| 109 | IVVGVILLRIVIYIVQMLAKLRQGY | SE59 | 697-721 |
| 110 | YIVQMLAKLRQGYRPVFSSPPSYFQ | SE60 | 709-733 |
| 111 | YRPVFSSPPSYFQQTHIQQDPALPT | SE61 | 721-745 |
| 112 | QQTHIQQDPALPTREGKERDGGEGG | SE62 | 733-757 |
| 113 | TREGKERDGGEGGGNSSWPWQIEYI | SE63 | 745-769 |
| 114 | GGNSSWPWQIEYIHFLIRQLIRLLT | SE64 | 757-781 |
| 115 | IHFLIRQLIRLLTWLFSNCRTLLSR | SE65 | 769-793 |
| 116 | TWLFSNCRTLLSRVYQILQPILQRL | SE66 | 781-805 |
| 117 | RVYQILQPILQRLSATLQRIREVLR | SE67 | 793-817 |
| 118 | LSATLQRIREVLRTELTYLQYGWSY | SE68 | 805-829 |
| 119 | RTELTYLQYGWSYFHEAVQAVWRSA | SE69 | 817-841 |
| 120 | YFHEAVQAVWRSATETLAGAWGDLW | SE70 | 829-853 |
| 121 | ATETLAGAWGDLWETLRRGGRWILA | SE71 | 841-865 |
| 122 | WETLRRGGRWILAIPRRIRQGLELTLL | SE72 | 853-877 |

The cultures were incubated overnight at 37° C. in a 7% $CO_2$ humidified atmosphere. Cells from each well were gently removed, transferred to 5.0 ml FACS test tubes and washed. One set of cells was stained with anti-CD3+ anti-CD4+. The other duplicate set was stained with anti-CD3+ anti-CD8+ (see below). These cell surface stained cells were then permeabilized and stained for intracellular content of IFN-gamma using an anti-IFN-gamma staining antibody using standard intracellular staining protocols. Each stained cell population (about 10,000 cells from each tube) was then analyzed using a FACS flow cytometer and the frequency of CD3+ CD4+ and CD3+ CD8+ T cells synthesizing IFN-gamma was determined. The negative and positive controls were utilized for background control and for positive control references. About 1000 analyses were performed in this manner during this experiment.

The frequency of CD4+ T cells (y axis) that expressed IFN-gamma by spleen cells from the six groups of mice in response to pools of SIV env peptide (9 pools) and SIV gag peptides (7 pools) were determined. Also determined was the frequency of CD8+ T cells (y axis) that express IFN-gamma by spleen cells from the same six groups of mice in response to pools of SIV env peptide (9 pools) and SIV gag peptides (7 pools). Data were the mean value from 4 mice/group. Results of these initial studies indicated that delipidated SIVmac251 at a dose of 10 ug or 1.0 ug led to marked augmentation of the SIV specific humoral responses in previously primed BALB/c mice. Even a dose of 0.1 ug ($5\times10^6$ viral particles) led to detectable enhancement of the SIV specific humoral responses in these mice. A dose of 1.0 ug, but not 10 ug, led to markedly broad breadth of SIV env and SIV gag peptide specific CD4+ T cell responses as measured by IFN-g synthesis in previously primed BALB/c mice.

EXAMPLE 4

Charcoal Removal of Solvents After Plasma Delipidation

A charcoal column was generated by loading 2 ml of PBS-washed Hemasorba charcoal into 3-ml BD LuerLock syringe containing a Whatman filter frit. The column was washed with 5% glucose/PBS (5 to 10 column volumes). The column was incubated in 5% glucose/PBS for 30 min. This column was used to remove solvents from treated plasma.

About 2 ml of freshly isolated human plasma (ACD) was mixed with 1 ml of one the following solvents: 1% DIPE; 10% DIPE; or butanol/DIPE (25:75). The mixture was vortexed for 15 seconds and then centrifuged 5 min at 3000 rpm (~1000×g). The solvent layer was aspirated. The plasma was passed through the charcoal column described in the preceding paragraph. About 0.5 ml of PBS was used to wash the column. Washing may occur several times as needed. The results are shown in Table 9. Total cholesterol (TC), triglycerides (TG), phospholipid (PL), apolipoprotein A1 (ApoA1), apolipoprotein B (ApoB) and HDL were measured. The results show good recoveries of ApoA1, ApoB and HDL compared to controls

TABLE 9

Analysis of Plasma Delipidated and Passed Through Charcoal Syringe Columns

| Sample | TC | TG | PL | ApoA1 | ApoB | HDL |
|---|---|---|---|---|---|---|
| Assay CSI | 132.8 | 83.5 | 154.2 | 106.0 | 60.5 | 17.3 |
| Assay CSII | 197.4 | 164.7 | 224.0 | 87.2 | 107.7 | 21.3 |
| Control 1 | 66.2 | 76.0 | 57.4 | 47.8 | 31.5 | 10.5 |
| Control 2 | 103.6 | 113.2 | 98.7 | 79.6 | 48.8 | 15.6 |
| 1% DIPE (1 pass) | 48.1 | 59.2 | 38.6 | 39.4 | 15.6 | 10.1 |
| 1% DIPE (2 pass) | 40.1 | 46.5 | 29.3 | 26.0 | 15.7 | 6.8 |
| 10% DIPE (1 pass) | 56.9 | 60.3 | 45.0 | 37.0 | 20.1 | 8.9 |
| 10% DIPE (2 pass) | 58.9 | 61.7 | 52.4 | 42.2 | 25.5 | 8.5 |
| But/DIPE (1 pass) | 57.4 | 65.0 | 54.1 | 47.7 | 24.8 | 9.1 |
| But/DIPE (2 pass) | 81.7 | 84.4 | 73.8 | 53.8 | 34.2 | 9.2 |

Plasma Virus Recovery After Passage Through Charcoal Column

Freshly isolated human plasma (ACD) was combined with HIV-1 to 1 ug/ml p24. HIV was added to the plasma such that the final concentration or particle content was 1 ug/ml of virus p24 antigen. Next, 1 ml of this plasma was passed through the column followed by 1 ml of PBS wash. The flow through and wash were combined. This procedure was repeated twice on fresh columns using 1 ml of the plasma. The flow through and wash from each of these three runs were analyzed separately. The results showed excellent recovery of p24 from the columns. P24 was measured by a standard capture ELISA protocol with a monoclonal antibody coated plate (for capture) and a polyclonal antibody for detection. Standard curves with known amounts of p24 are used to determined the p24 content of unknowns.

Direct Delipidation of HIV-1 and Removal of Solvents with Charcoal Column and Retention of HIV Proteins About 25 ul of 1000× HIV-1 IIIB was mixed with 1) nothing; 2) 12.5 ul butanol/DIPE (25:75); 3) 2.5 ul 100% DIPE; or 4) 12.5 ul 1% DIPE in PBS and the samples were vortexed for 15 seconds. Charcoal columns (0.5-ml) were prepared as described above. The virus-solvent mixtures were loaded individually onto separate columns. The columns were eluted with 1 ml of PBS. The elution volumes were measured and samples assayed for p24 by ELISA, protein, and subjected to Western blotting.

The samples treated with 1% DIPE showed excellent p24 recovery compared to controls. The samples treated with 10% DIPE or butanol/DIPE showed slightly less p24 recovery. The total protein recovery was similar in terms of percentage relative to control, to the p24 results obtained 1% DIPE, 10% DIPE or butanol/DIPE.

Western blot analysis, performed in a similar manner to the protocol provided below in this example, revealed numerous immunoreactive bands when probed with human anti-HIV IgG with butanol/DIPE, 10% DIPE or 1% DIPE solvent treatments. Western blot analysis also revealed positive immunoreactive bands corresponding to p24 with butanol/DIPE, 10% DIPE or 1% DIPE. Positive immunoreactive bands were observed for gp41 using 10% DIPE or 1% DIPE. Additional positive immunoreactive bands were observed for gp120 with butanol/DIPE, 10% DIPE or I%DIPE, although the intensity of staining was higher with 10% DIPE or 1% DIPE.

SIV and HIV Western Blot Analysis

Reagents for comparison included delipidated SIV-mac251, heat inactivated SIV mac251 and a rabbit polyclonal antibody against whole SIV (available through the AIDS reagent repository, Rockville, Md.). About 1 ug of protein was required to visualize most of the SIV bands in the Western blot. SDS-polyacrylamide gel electrophoresis (SDS-PAGE) was performed on the viral lysates (lysate buffer:50 mM Tris-HCl, pH 7.4; 1% NP-40; 0.25% sodium deoxycholate; 150 mM NaCl; 1 mM EGTA; 1 mM PMSF; 1 ug/ml each of aprotinin, leupeptin and pepstatin; 1 mM sodium vanadate; 1 mM NaF).

A silver stain was used to visualize the bands which reveal the various viral proteins present following delipidation with respect to molecular weight standards. The heat inactivated SIVmac251 proteins were compared with the delipidated SIVmac251 proteins on the gels. A similar SDS-PAGE was run and the proteins are transferred to nitrocellulose. The blotted nitrocellulose was washed twice with water. A minimum of three blots each for the delipidated SIVmac251 and the heat inactivated SIVmac251 were run.

The blotted nitrocellulose was blocked in freshly prepared PBS containing 3% nonfat dry milk (MLK) for 20 min at 20-25° C. with constant agitation. The nitrocellulose strips were incubated with a freshly prepared predetermined optimum concentration of the rabbit polyclonal anti-SIV antiserum (about 5 ml of a 1:1000 dilution of the antiserum in PBS-MLK) overnight with agitation. The nitrocellulose strips were washed twice with water. The strips were incubated with horseradish peroxidases (HRP)-conjugated goat anti-rabbit IgG 1:3000 dilution in PBS-MLK for 90 min at room temperature with agitation. The nitrocellulose was washed with water twice and then with PBS-0.05% Tween 20 for 3-5 min. The nitrocellulose strips were washed with 4-5 changes of water. Detection of the developed bands was achieved via detection of the developed bands. The bands developed using the heat inactivated SIV with the delipidated SIV were compared.

A similar approach was used for Western blot analysis of solvent treated HIV-1 passed through charcoal columns and probed for p24, gp41, gp120, and also for HIV antigens using an human anti-HIV IgG. Western blotting was performed on SDS-PAGE separated virus samples transferred onto nitrocellulose membranes. The membranes are probed with polyclonal and monoclonal antibodies to viral proteins and developed with secondary antibodies conjugated with peroxidase and enhanced chemiluminescence reagents.

EXAMPLE 5

Use of a Kit for Delipidation of a Plasma Sample Containing HIV and Production of Delipidated HIV Viral Particles A 200 ml plasma sample, stored in a plasma bag with a tube connected to an opening in the bag, is obtained from blood drawn from a 22 year old patient afflicted with the human immunodeficiency virus (HIV) and showing symptoms of acquired immunodeficiency syndrome (AIDS). The patient requires a reduction in the viral load in the blood. The plasma sample is exposed to a first extraction solvent to remove lipid from the viral envelope of the HIV virus.

A first container with a 500 ml capacity is removed from the kit. The first container, which is graduated, contains a known volume (about 200 ml) of a first extraction solvent. The entire plasma sample is added to the first container through a removable screw cap. The first container is agitated through repeated inversion, thereby mixing the first extraction solvent and the plasma sample sufficiently to create a mixture. The first container is placed on a counter and the mixture settles into two phases.

The delipidated plasma phase is removed with a manual pipette or a pipette connected to a vacuum, and placed in a second container from the kit. The volatile components of the first extraction solvent evaporate. Mild heating may be employed at this step. A tube, obtained from the kit, is inserted into the second container. The tube serves as, or is connected to, an intravascular line leading to a needle introduced into the antecubital vein of the patient. The delipidated fluid containing delipidated plasma and delipidated HIV viral particles with reduced infectivity is introduced into the vascular system through the force of gravity by elevating the second container above the patient. The needle is optionally obtained from the kit. Administration of the delipidated HIV viral particles into the vascular system induces an immune response in the patient to epitopes on the delipidated HIV viral particles.

EXAMPLE 6

Use of a Kit for Delipidation of a Plasma Sample Containing HIV and Production of Delipidated HIV Viral Particles A 200 ml plasma sample, stored in a plasma bag with a tube connected to an opening in the bag, is obtained from blood drawn from a 22 year old patient afflicted with the human immunodeficiency virus (HIV) and showing symptoms of AIDS. The patient requires a reduction in the viral load in the blood. The plasma sample is exposed to a first extraction solvent to remove lipid from the viral envelope of the HIV virus.

A first container with a 500 ml capacity is removed from the kit. The first container, which is graduated, contains a known volume (about 200 ml) of a first extraction solvent. The entire plasma sample is added to a second container through a removable screw cap. The contents of the first container and the second container are added to a third container obtained from the kit. The third container is agitated through repeated inversion, thereby mixing the first extraction solvent and the plasma sample sufficiently to create a mixture. The third container is placed on a counter and the mixture settles into two phases.

The delipidated plasma phase is removed with a manual pipette or a pipette connected to a vacuum, and placed in a fourth container from the kit. The volatile components of the first extraction solvent evaporate. Mild heating may be employed at this step. A tube, obtained from the kit, is inserted into the fourth container. The tube serves as, or is connected to, an intravascular line leading to a needle introduced into the antecubital vein of the patient. The delipidated fluid containing delipidated plasma and delipidated HIV viral particles with reduced infectivity is introduced into the vascular system through the force of gravity by elevating the fourth container above the patient. The needle is optionally obtained from the kit. Administration of the delipidated HIV viral particles into the vascular system induces an immune response in the patient to epitopes on the delipidated HIV viral particles.

EXAMPLE 7

Use of a Kit for Delipidation of a Plasma Sample Containing HIV and Production of Delipidated HIV Viral Particles A 200 ml plasma sample, stored in a plasma bag with a tube connected to an opening in the bag, is obtained from blood drawn from a 22 year old patient afflicted with the human immunodeficiency virus (HIV) and showing symptoms of AIDS. The patient requires a reduction in the viral load in the blood. The plasma sample is exposed to a first extraction solvent to remove lipid from the viral envelope of the HIV virus.

A first container with a 500 ml capacity is removed from the kit. The first container, which is graduated, contains a known volume (about 200 ml) of a first extraction solvent. The entire plasma sample is added to a second container through a removable screw cap. The contents of the first container and the second container are added to a third container obtained from the kit. The third container is agitated through repeated inversion, thereby mixing the first extraction solvent and the plasma sample sufficiently to create a mixture. The third container is placed on a counter and the mixture settles into two phases.

The delipidated plasma phase is removed with a manual pipette or a pipette connected to a vacuum, and placed in a fourth container from the kit. The volatile components of the first extraction solvent evaporate. Mild heating may be employed at this step. A second extraction solvent, contained in a graduated fifth container, is poured into the fourth container in order to remove residual first extraction solvent. The fourth container is agitated through repeated inversion, thereby mixing residual first extraction solvent, the partially delipidated plasma sample and the second extraction solvent sufficiently to create a mixture. The fourth container is allowed to sit and the mixture separates into a delipidated plasma layer and a solvent layer containing the second extraction solvent and residual first extraction solvent. The delipidated plasma layer is removed and placed in a sixth container obtained from the kit. A tube, obtained from the kit, is inserted into the sixth container. The tube serves as or is connected to an intravascular line leading to a needle introduced into the antecubital vein of the patient. The delipidated fluid containing delipidated plasma and delipidated HIV viral particles with reduced infectivity is introduced into the vascular system through the force of gravity by elevating the sixth container above the patient. The needle is optionally obtained from the kit. Administration of the delipidated HIV viral particles into the vascular system induces an immune response in the patient to epitopes on the delipidated HIV viral particles.

All patents, publications and abstracts cited above are incorporated herein by reference in their entirety. It should be understood, of course, that the foregoing relates only to preferred embodiments of the present invention and that numerous modifications or alterations may be made therein without departing from the spirit and the scope of the invention as set forth in the appended claims.

We claim:

1. A modified viral particle comprising at least a partially delipidated viral particle, wherein the partially delipidated viral particle is immunodeficiency virus and the partially delipidated viral particle:

initiates a positive immune response in an animal or human;

comprises at least one exposed epitope not usually presented to an immune system of the animal or the human by a non-delipidated viral particle; and wherein the partially delipidated viral particle is obtained by a process consisting essentially of treating a lipid-containing viral particle with an organic solvent that is not a detergent or a surfactant.

2. The modified viral particle of claim 1, wherein the immunodeficiency virus is SIV or FIV.

3. The modified viral particle of claim 1, wherein the immunodeficiency virus is HIV.

4. The modified viral particle of claim 3, wherein the HIV is HIV-1 or HIV-2.

5. The modified viral particle of claim 1, wherein the at least one exposed epitope is a gag, p6 gag, gp66, gp41, p27, or env epitope.

6. The modified viral particle of claim 1, wherein the modified viral particle has a lower lipid content in a viral envelope as compared to the non-delipidated particle.

7. The modified viral particle of claim 1, wherein one or more protein on, in, or near the surface of the partially delipidated viral particle is conformationally changed as compared to one or more proteins on, in, or near the surface of the non-delipidated viral particle.

8. The modified viral particle of claim 1, wherein an antigenic core of the modified viral particle remains intact as compared to the non-delipidated viral particle.

9. The modified viral particle of claim 2, wherein the immunodeficiency virus is SIV and the modified viral particle retains over 90% of major protein constituents compared to the non-delipidated viral particle.

10. The modified viral particle of claim 9, wherein the major protein constituents of the modified viral particle comprise gag or env proteins.

11. The modified viral particle of claim 1, wherein the modified viral particle retains at least one immunoreactive protein.

12. The modified viral particle of claim 11, wherein the at least one immunoreactive protein is selected from the group consisting of p24, gp41 and gp120.

13. The modified viral particle of claim 12, wherein the modified viral particle comprises at least one exposed patient specific antigen that was not exposed in the non-delipidated viral particle.

14. The modified viral particle of claim 1, wherein the treating of a lipid-containing viral particle with an organic solvent that is not a detergent or a surfactant comprises:

contacting the lipid-containing viral particle in a fluid with a solvent consisting essentially of the organic solvent that is not the detergent or the surfactant and is capable of extracting lipid from the lipid-containing viral particle;

mixing the fluid and the organic solvent for a time sufficient to extract lipid from the lipid-containing viral particle;

permitting organic and aqueous phases to separate; and, collecting the aqueous phase containing the modified viral particle with reduced lipid content wherein the modified viral particle with reduced lipid content is capable of provoking a positive immune response when administered to the animal or the human.

15. The modified viral particle of claim 14, wherein the treating of a lipid-containing viral particle with an organic solvent that is not a detergent or a surfactant further comprises:

contacting the aqueous phase with a de-emulsifying agent capable of removing the organic solvent; and, separating the de-emulsifying agent and the removed organic solvent from the contacted aqueous phase.

16. The modified viral particle of claim 14, wherein the organic solvent is an alcohol, an ether, an amine, a hydrocarbon, an ester, or a combination thereof.

17. The modified viral particle of claim 16, wherein the ether is C4 to C8 ether and the alcohol is a C1 to C8 alcohol.

18. The modified viral particle of claim 15, wherein the de-emulsifying agent is an ether.

19. The modified viral particle of claim 1, further comprising a pharmaceutically acceptable carrier.

20. The modified viral particle of claim 1, wherein the at least one exposed epitope is an envelope protein epitope.

21. The modified viral particle of claim 1, wherein the modified viral particle has a lower lipid content in a viral envelope than the lipid content in an envelope of the non-delipidated viral particle.

22. The modified viral particle of claim 1, wherein the partially delipidated viral particle has an infectivity reduced by no more than 2.5 log units as compared to the non-delipidated viral particle.

23. A modified viral particle comprising at least a partially delipidated viral particle, wherein the partially delipidated viral particle is immunodeficiency virus and the partially delipidated viral particle:

initiates a positive immune response in an animal or a human;

comprises at least one exposed epitope not usually presented to an immune system of the animal or the human by a non-delipidated viral particle, wherein the modified viral particle comprises at least one immunoreactive protein selected from a group consisting of p24, gp41 and gp120; and is obtained by a process consisting essentially of treating a lipid-containing viral particle with an organic solvent that is not a detergent or a surfactant.

24. A modified viral particle comprising at least a partially delipidated viral particle, wherein the partially delipidated viral particle is immunodeficiency virus and the partially delipidated viral particle:

initiates a positive immune response in an animal or a human;

comprises an envelope, wherein the envelope comprises no extrinsic detergent or surfactant molecules; and, comprises at least one exposed epitope not usually presented to an immune system of the animal or the human by a non-delipidated viral particle, wherein the modified viral particle is SIV and retains over 90% of major protein constituents compared to the non-delipidated viral particle and the major protein constituents of the modified viral particle comprise gag or env proteins;

wherein the partially delipidated viral particle is obtained by a process consisting essentially of treating a lipid-containing viral particle with an organic solvent that is not a detergent or a surfactant.

* * * * *